(12) United States Patent
Ghobrial et al.

(10) Patent No.: US 9,944,991 B2
(45) Date of Patent: Apr. 17, 2018

(54) COMPOSITIONS AND METHODS FOR DIAGNOSIS, PROGNOSIS AND TREATMENT OF HEMATOLOGICAL MALIGNANCIES

(71) Applicant: Dana-Farber Cancer Institute, Inc., Boston, MA (US)

(72) Inventors: Irene Ghobrial, Wellesley, MA (US); Aldo M. Roccaro, Boston, MA (US); Salomon Manier, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/438,715

(22) PCT Filed: Nov. 1, 2013

(86) PCT No.: PCT/US2013/068093
§ 371 (c)(1),
(2) Date: Apr. 27, 2015

(87) PCT Pub. No.: WO2014/071205
PCT Pub. Date: May 8, 2014

(65) Prior Publication Data
US 2015/0322529 A1    Nov. 12, 2015

Related U.S. Application Data

(60) Provisional application No. 61/796,126, filed on Nov. 2, 2012.

(51) Int. Cl.
| | |
|---|---|
| *C12Q 1/68* | (2018.01) |
| *A61K 39/395* | (2006.01) |
| *C12N 15/113* | (2010.01) |
| *A61K 35/14* | (2015.01) |
| *A61K 45/06* | (2006.01) |
| *A61K 31/436* | (2006.01) |
| *A61K 31/69* | (2006.01) |
| *A61K 31/7088* | (2006.01) |
| *A61K 31/713* | (2006.01) |
| *C07K 16/28* | (2006.01) |
| *A61K 39/00* | (2006.01) |

(52) U.S. Cl.
CPC .......... *C12Q 1/6886* (2013.01); *A61K 31/436* (2013.01); *A61K 31/69* (2013.01); *A61K 31/7088* (2013.01); *A61K 31/713* (2013.01); *A61K 35/14* (2013.01); *A61K 39/3955* (2013.01); *A61K 39/39558* (2013.01); *A61K 45/06* (2013.01); *C07K 16/2887* (2013.01); *C12N 15/113* (2013.01); *A61K 2039/505* (2013.01); *C12N 2310/141* (2013.01); *C12Q 2600/106* (2013.01); *C12Q 2600/16* (2013.01); *C12Q 2600/178* (2013.01)

(58) Field of Classification Search
CPC ..................................................... C12Q 1/68
See application file for complete search history.

(56) References Cited

U.S. PATENT DOCUMENTS

| | | | |
|---|---|---|---|
| 2009/0143326 A1 | 6/2009 | Obad | |
| 2011/0152357 A1 | 6/2011 | Croce | |
| 2011/0313025 A1 | 12/2011 | Brown | |
| 2012/0252871 A1* | 10/2012 | Galas | ............... C12Q 1/6886 514/44 A |

FOREIGN PATENT DOCUMENTS

WO    WO2011068546 A3    10/2011

OTHER PUBLICATIONS

Garzon et al. (Annu. Rev. Med. 2009. 60: 167-79).*
Wright et al. (Clin Cancer Res 16(16) Aug. 15, 2010).*
Azab A.K., et al., RhoA and Rac1 GTPases play major and differential roles in stromal cell-derived factor-1-induced cell adhesion and chemotaxis in multiple myeloma, Blood, 114(3):619-29 (2009).
Azab A.K. et al., Hypoxia promotes dissemination of multiple myeloma through acquisition of epithelial to mesenchymal transition-like features, Blood, 119(24):5782-94 (2012).
Aziz A. et al., MafB/c-Maf deficiency enables self-renewal of differentiated functional macrophages, Science, 326(5954):867-871(2009).
Blanchard N. et al., TCR activation of human T cells induces the production of exosomes bearing the TCR/CD3/zeta complex, J. Immunol., 168(7):3235-41 (2002).
Dimopoulos M. et al., International myeloma working group consensus statement and guidelines regarding the current role of imaging techniques in the diagnosis and monitoring of multiple Myeloma, Leukemia, 23(9):1545-56 (2009).
Dominici et al., Minimal criteria for defining multipotent mesenchymal stromal cells. The International Society for Cellular Therapy position statement, Cytotherapy, 8(4):315-317 (2006).
Durie B.G. et al., International uniform response criteria for multiple myeloma, Leukemia, 20(9):1467-73 (2006).
Eychene A. et al., A new MAFia in cancer, Nat. Rev. Cancer, 8(9):683-693 (2008).
Fingar D.C. et al., mTOR controls cell cycle progression through its cell growth effectors S6K1 and 4E-BP1/eukaryotic translation initiation factor 4E, Mol. Cell. Biol., 24(1):200-16 (2004).
Fonti R. et al., 18F-FDG PET/CT, 99mTc-MIBI, and MRI in evaluation of patients with multiple myeloma, J. Nucl. Med., 49(2):195-200 (2008).

(Continued)

Primary Examiner — Kimberly Chong
(74) Attorney, Agent, or Firm — Fish & Richardson P.C.

(57) ABSTRACT

This invention is based, at least in part, on the finding that certain microRNAs (miRNAs) are expressed at higher or lower levels in circulating exosomes or peripheral blood of subjects with hematological malignancies compared to the level of expression in subjects who do not have the hematological malignancy. In addition, this invention is based, at least in part, on the finding that certain miRNAs are differentially expressed at different stages of a hematological malignancy permitting identification of the stage of the hematological malignancy in a subject. The differential expression of miRNAs at different stages of a hematological malignancy also permits determination of the effectiveness of treatments administered to a subject at the particular stage of the hematological malignancy.

10 Claims, 46 Drawing Sheets

(56) References Cited

OTHER PUBLICATIONS

Garayoa M. et al., Mesenchymal stem cells from multiple myeloma patients display distinct genomic profile as compared with those from normal donors, Leukemia, 23(8):1515-1527 (2009).
Ghobrial I.M. et al., Proteomic analysis of mantle-cell lymphoma by protein microarray, Blood, 105(9):3722-3730 (2005).
Ghobrial I.M. et al., Phase II trial of the oral mammalian target of rapamycin inhibitor everolimus in relapsed or refractory Waldenstrom macroglobulinemia, J. Clin. Oncol., 28(8):1408-14 (2010).
Giri P.K. et al., Exosomes derived from M. Bovis BCG infected macrophages activate antigen-specific CD4+ and CD8+ T cells in vitro and in vivo, PloS One 3(6):e2461 (2008).
Goldstein R.H. et al., Human bone marrow-derived MSCs can home to orthotopic breast cancer tumors and promote bone metastasis, Cancer Res., 70(24):10044-10050 (2010).
Greipp P.R. et al., International staging system for multiple myeloma, J. Clin. Oncol., 23(15):3412-20 (2005).
Hideshima T. et al., Advances in biology of multiple myeloma: clinical applications, Blood, 104(3):607-618 (2004).
Higgins, Fast and sensitive multiple sequence alignments on a microcomputer Comput Appl Biosci, 5(2): 151-153 (1989).
Hsieh A.C. et al., The translational landscape of mTOR signalling steers cancer initiation and metastasis, Nature, 485(7396):55-60 (2012).
Hurt E.M. et al., Overexpression of c-maf is a frequent oncogenic event in multiple myeloma that promotes proliferation and pathological interactions with bone marrow stroma, Cancer Cell, 5(2):191-199 (2004).
International Myeloma Working Group, Criteria for the classification of monoclonal gammopathies, multiple myeloma and related disorders: a report of the International Myeloma Working Group, Br. J. Haematol., 121(5):749-57 (2003).
Karolina D.S. et al., MicroRNA 144 impairs insulin signaling by inhibiting the expression of insulin receptor substrate 1 in type 2 diabetes mellitus, PLoS One, 6(8): e22839 (2011).
Khan S. et al., Survivin is released from cancer cells via exosomes, Apoptosis, 16(1):1-12 (2011).
Kroh E.M. et al., Analysis of circulating microRNA biomarkers in plasma and serum using quantitative reverse transcription-PCR (qRT-PCR), Methods, 50(4):298-301 (2010).
Kyle R.A. et al., Multiple myeloma, Blood, 111(6):2962-72 (2008).
Kyle R.A. et al., Criteria for diagnosis, staging, risk stratification and response assessment of multiple myeloma, Leukemia, 23(1):3-9 (2009).
Landgren O. et al., Monoclonal gammopathy of undetermined significance (MGUS) consistently precedes multiple myeloma: a prospective study, Blood, 113(22):5412-7 (2009).
Leleu X., et al., The Akt pathway regulates survival and homing in Waldenstrom macroglobulinemia, Blood,110(13):4417-4426 (2007).
Leleu X. et al., Waldenstrom macroglobulinemia, Cancer Lett., 270(1):95-107 (2008).
Leleu X. et al., Targeting NF-kappaB in Waldenstrom macroglobulinemia, Blood, 111(10):5068-77 (2008).
Livak K.J. et al., Analysis of relative gene expression data using real-time quantitative PCR and the 2(-Delta Delta C(T)) Method, Methods, 25(4):402-408 (2001).
Mestdagh P. et al., A novel and universal method for microRNA RT-qPCR data normalization, Genome Biol., 10(6):R64 (2009).
Mitchell et al. Circulating microRNAs as stable blood-based markers for cancer detection, Proc. Natl. Acad. Sci. USA, 105(30): 10513-10518 (2008).
Montecalvo A. et al., Exosomes as a short-range mechanism to spread alloantigen between dendritic cells during T cell allorecognition, J. Immunol.,180(5):3081-3090 (2008).
Morel P. et al., International prognostic scoring system for Waldenstrom macroglobulinemia, Blood, 113(18):4163-70(2009).
Morito N. et al., Overexpression of c-Maf contributes to T-cell lymphoma in both mice and human, Cancer Res., 66(2):812-819 (2006).
Needleman, A general method applicable to the search for similarities in the amino acid sequence of two proteins, J. Mol. Biol., 48(3); 443-453 (1970).
Obad S., Silencing of microRNA families by seed-targeting tiny LNAs, Nat. Genet., 43(4):371-378 (2011).
Pedersen I.M. et al., Onco-miR-155 targets SHIP1 to promote TNFalpha-dependent growth of B cell lymphomas, EMBO Mol. Med., 1(5):288-95 (2009).
Peinado H. et al., Melanoma exosomes educate bone marrow progenitor cells toward a pro-metastatic phenotype through MET, Nat. Med., 18(6):883-91 (2012).
Piehler A.P. et al., Quantitation of serum free light chains in combination with protein electrophoresis and clinical information for diagnosing multiple myeloma in a general hospital population, Clin. Chem., 54(11):1823-30 (2008).
Pouponnot C. et al., Cell context reveals a dual role for Maf in oncogenesis, Oncogene, 25(9):1299-1310 (2006).
Raaijmakers M.H. et al., Bone progenitor dysfunction induces myelodysplasia and secondary leukaemia, Nature, 464(7290):852-857 (2010).
Rajkumar S.V., Presence of monoclonal free light chains in the serum predicts risk of progression in monoclonal gammopathy of undetermined significance, Br. J. Haematol., 127(3):308-10 (2004).
Rajkumar S.V., Monoclonal gammopathy of undetermined significance and smoldering multiple myeloma, Blood Rev., 21(5):255-65, (2007).
Raposo G. et al., B lymphocytes secrete antigen presenting vesicles, J. Exp. Med., 183(3):1161-72, (1996).
Raposo G. et al., Accumulation of major histocompatibility complex class II molecules in mast cell secretory granules and their release upon degranulation, Mol. Biol. Cell, 8(12):2631-45 (1997).
Ritchie M.E. et al., A comparison of background correction methods for two-colour microarrays, Bioinformatics, 23(20):2700-2707 (2007).
Roccaro A.M. et al., Bortezomib mediates antiangiogenesis in multiple myeloma via direct and indirect effects on endothelial cells, Cancer Res., 66(1):184-91 (2006).
Roccaro A.M. et al., Dual targeting of the proteasome regulates survival and homing in Waldenstrom macroglobulinemia, Blood, 111(9):4752-63 (2008).
Roccaro A.M. et al., microRNA expression in the biology, prognosis, and therapy of Waldenström macroglobulinemia, Blood, 113(18):4391-402 (2009).
Roccaro A.M. et al., MicroRNAs 15a and 16 regulate tumor proliferation in multiple myeloma, Blood, 113(26):6669-80 (2009).
Sacco A. et al., Carfilzomib-dependent selective inhibition of the chymotrypsin-like activity of the proteasome leads to antitumor activity in Waldenstrom's Macroglobulinemia, Clin Cancer Res., 17(7):1753-64 (2011).
Sipkins D.A. et al., In vivo imaging of specialized bone marrow endothelial microdomains for tumor engraftment, Nature, 435(7044):969-973 (2005).
Skog J. et al., Glioblastoma microvesicles transport RNA and proteins that promote tumour growth and provide diagnostic biomarkers, Nat. Cell. Biol., 10(12):1470-1476 (2008).
Smith, Comparison of biosequences, Adv. Appl. Math., 2:482-489 (1981).
Smyth G.K., Normalization of cDNA microarray data, Methods, 31(4): 265-273 (2003).
Smyth, G. K. Limma: linear models for microarray data. In: Bioinformatics and Computational Biology Solutions using R and Bioconductor, R. Gentleman, V. Carey, S. Dudoit, R. Irizarry, W. 2005. Huber, eds. (Springer, New York), pp. 397-420.
Thery C. et al., Molecular characterization of dendritic cell-derived exosomes. Selective accumulation of the heat shock protein hsc73, J. Cell Biol., 147(3):599-610 (1999).
Vacca et al., Bone marrow angiogenesis in multiple myeloma, Leukemia, 20(2):193-9 (2006)).

(56) References Cited

OTHER PUBLICATIONS van Niel G. et al., Intestinal epithelial cells secrete exosome-like vesicles, Gastroenterol., 121(2):337-49 (2001).
van Niel G. et al., Exosomes: a common pathway for a specialized function, J. Biochem., 140(1):13-21, (2006).
Yu S. et al., Tumor exosomes inhibit differentiation of bone marrow dendritic cells, J. Immunol.,178(11):6867-6875 (2007).
Ghobrial et al., "Targeting the bone marrow in Waldenstrom macroglobulinemia." Clin Lymphoma Myeloma Leuk. (Jun. 2011, published online Apr. 30, 2011) Suppl 1, pp. S65-S69.
Notification of Transmittal of the International Search Report and the Written Opinion of the International Searching Authority for PCT/US2013/068093 dated Jan. 29, 2014, 19 pages.
Feng et al., Progressive sequence alignment as a prerequisite to correct phylogenetic trees, J. Mol. Evolution, 25(4):351-360 (1987).
Kyle R.A. et al., Multiple myeloma, N. Engl. J. Med., 351:1860-73 (2004).
Kyle R.A. et al., Monoclonal gammopathy of undetermined significance, Clin. Lymphoma Myeloma, 6(2):102-14 (2005).
Kyrtsonis M.C. et al., Staging systems and prognostic factors as a guide to therapeutic decisions in multiple myeloma, Semin. Hematol., 46(2):110-7 (2009).
Mears R. et al., Proteomic analysis of melanoma-derived exosomes by two-dimensional polyacrylamide gel electrophoresis and mass spectrometry, Proteomics, 4(12):4019-31 (2004).
Mitsiades C.S. et al., The role of the bone microenvironment in the pathophysiology and therapeutic management of multiple myeloma: interplay of growth factors, their receptors and stromal interactions, Eur. J. Cancer., 42(11):1564-73 (2006).
Ostrowski M. et al., Rab27a and Rab27b control different steps of the exosome secretion pathway, Nat. Cell Biol., 12(1):19-30 (2010).
Pan B.T. et al., Fate of the transferrin receptor during maturation of sheep reticulocytes in vitro: selective externalization of the receptor, Cell, 33(3):967-78 (1983).
Thery C. et al., Membrane vesicles as conveyors of immune responses, Nat. Rev. Immunol., 9(8):581-93, (2009).
Valadi et al., Exosome-mediated transfer of mRNAs and microRNAs is a novel mechanism of genetic exchange between cells, Nat. Cell. Biol., 9(6):654-659 (2007).

* cited by examiner

Distribution of FAM-labeled antimiR-155 in mice.

A

Week 1

Week 2

B

D

E

B

C

C

D

A

B

C

D

E

F

SEQUENCE LISTING

```
<160> NUMBER OF SEQ ID NOS: 11

<210> SEQ ID NO 1
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 1
aaauacaaaa aaucugcauu aaa                                             23

<210> SEQ ID NO 2
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 2
aaauacaaaa aaucucguaa uaa                                             23
```

```
<210> SEQ ID NO 3
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 3
ggaaauuuca cacuggcauu aac                                              23

<210> SEQ ID NO 4
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 4
ggaaauuagu gacugcguaa uac                                              23

<210> SEQ ID NO 5
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 5
guuauugaac aagcaagcau uau                                              23

<210> SEQ ID NO 6
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 6
guuauugaac aagcaucgua auu                                              23

<210> SEQ ID NO 7
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 7
aucaugagau gaaugagcau uac                                              23

<210> SEQ ID NO 8
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 8
aucaugagau gaaugucgua auc                                              23

<210> SEQ ID NO 9
<211> LENGTH: 8
<212> TYPE: DNA
<213> ORGANISM: Artificial Sequence
<220> FEATURE:
<223> OTHER INFORMATION: synthetic oligonucleotide
```

```
<400> SEQUENCE: 9 attacgat                                                                 8

<210> SEQ ID NO 10
<211> LENGTH: 23
<212> TYPE: RNA
<213> ORGANISM: Mus musculus

<400> SEQUENCE: 10
uuaaugcuaa ucgugauagg ggu                                               23

<210> SEQ ID NO 11
<211> LENGTH: 23
<212> TYPE: RNA
<213> ORGANISM: Homo sapiens

<400> SEQUENCE: 11
uuaaugcuaa ucgugauagg ggu                                               23
```

COMPOSITIONS AND METHODS FOR DIAGNOSIS, PROGNOSIS AND TREATMENT OF HEMATOLOGICAL MALIGNANCIES

CROSS-REFERENCE TO RELATED APPLICATIONS

This application is a national stage application under 35 U.S.C. § 371 of International Patent Application No. PCT/US2013/068093, filed on Nov. 1, 2013, which claims priority to U.S. Provisional Application No. 61/796,126 filed Nov. 2, 2013, the entire contents of both of which are incorporated herein by reference in their entirety.

TECHNICAL FIELD

This invention relates generally to biomarkers for hematological malignancies, and more particularly to, methods of diagnosing hematological malignancies, selecting suitable therapies, and prognosis based on the expression levels of the biomarkers, as well as compositions and methods for treating hematological malignancies.

BACKGROUND

Hematological malignancies are types of cancers that affect the blood, the bone marrow, and the lymph nodes. They derive from either of the two major blood cell lineages namely, the myeloid and lymphoid lineages. The myeloid lineage normally produces granulocytes, erythrocytes, thrombocytes, macrophages and mast cells; whereas, the lymphoid lineage produces B, T, Natural Killer (NK), and plasma cells. Acute and chronic myelogenous leukemia, myelodysplastic syndromes and myeloproliferative diseases are examples of hematological malignancies of myeloid origin, while lymphomas, lymphocytic leukemias, and myeloma are examples of hematological malignancies of the lymphoid lineage.

Multiple myeloma is a form of cancer that affects a type of white blood cell called the plasma cell. Multiple myeloma appears in the bone marrow, which is the soft tissue inside the bones that makes stem cells. In multiple myeloma, plasma cells, which mature from stem cells and typically produce antibodies to fight germs and other harmful substances, become abnormal. These abnormal cells are called myeloma cells. In 2009, an estimated 20,580 cases of multiple myeloma were diagnosed in the United States. As the most common type of plasma cell cancer, effective treatment requires an accurate diagnosis and precise treatment.

Waldenström macroglobulinemia (WM) is a rare, slow-growing, non-Hodgkin lymphoma (i.e., a cancer that begins in the cells of the immune system). WM is also called lymphoplasmacytic lymphoma. Lymphoplasmacytic cells are cells that are in the process of maturing from B cells to plasma cells. In WM, abnormal lymphoplasmacytic cells multiply out of control, producing large amounts of a protein called monoclonal immunoglobulin M (IgM or "macroglobulin") antibody. High levels of IgM in the blood cause hyperviscosity (thickness or gumminess), which leads to many of the symptoms of WM. WM is a rare cancer; about 1,500 new cases occur annually in the United States.

B-cell chronic lymphocytic leukemia (B-CLL), also known as chronic lymphoid leukemia (CLL), is the most common type of leukemia. It is a blood and bone marrow disease that usually gets worse slowly. It often occurs during or after middle age; it rarely occurs in children.

Small lymphocytic lymphoma (SLL) is a type of non-Hodgkin lymphoma characterized by an excess of white blood cells in the lymph nodes. SLL accounts for about 4-5% of non-Hodgkin's lymphoma. In SLL the patients are elderly (median age 60 years) and usually present with diffuse lymphadenopathy and some degree of marrow and peripheral blood involvement. Men and women appear to develop the disease equally.

While there are existing methods to diagnose, predict, and treat hematological malignancies, improved methods are urgently needed.

SUMMARY

This invention is based, at least in part, on the finding that certain microRNAs (miRNAs) are expressed at higher or lower levels in circulating exosomes or peripheral blood of subjects with hematological malignancies compared to the level of expression in subjects who do not have the hematological malignancy. In addition, this invention is based, at least in part, on the finding that certain miRNAs are differentially expressed at different stages of a hematological malignancy permitting identification of the stage of the hematological malignancy in a subject. The differential expression of miRNAs at different stages of a hematological malignancy also permits determination of the effectiveness of treatments administered to a subject at the particular stage of the hematological malignancy. In addition, this disclosure provides methods of treating a subject at risk of developing, or presenting with a hematological malignancy. Furthermore, compositions that are useful, e.g., in treating a hematological malignancy are also disclosed herein.

In one aspect, the disclosure features a method of determining the likelihood of a subject having a hematological malignancy. The method involves identifying a subject who is suspected of having a hematological malignancy, obtaining a biological sample from the subject, and determining from the biological sample that: (i) the subject has an altered level of one or more micro RNAs (miRs) compared to a control level, or (ii) the subject does not have an altered level of expression of the miRs compared to the control level. The one or more miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. If the subject is determined as having an altered level of one or more miRs compared to the control level the subject is identified as likely to have the hematological malignancy. On the other hand, if the subject is determined as not having an altered level of one or more miRs compared to the control level the subject is identified as not likely to have the hematological malignancy.

In some embodiments of this aspect, an increased expression relative to the control level of at least one, at least two, at least three, at least four, at least five, at least six, at least seven, at least eight, at least nine, at least ten, at least eleven, or one, two, three, four, five, six, seven, eight, nine, ten, or eleven, or twelve of miR-450a, miR-30e, miR-125a, miR-300, miR-30d, miR-144, miR-451a, miR-107, miR-125b, miR-143, miR-720, and miR-155 is indicative that the subject has a hematological malignancy. In some embodiments of this aspect, a decreased expression relative to the control level of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or one, two, three, four, five, six, seven, eight, nine, ten, or eleven, twelve, thirteen, fourteen, fifteen, sixteen, seventeen, eighteen, nineteen, or twenty of miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c is indicative that the subject has a hematological malignancy (e.g., multiple myeloma or a stage thereof). In some embodiments of this aspect, an increased expression relative to the control level of at least one, at least two, at least three, at least four, at least five, at least six, at least seven, at least eight, at least nine, at least ten, or one, two, three, four, five, six, seven, eight, nine, ten, or eleven of miR-450a, miR-30e, miR-125a, miR-300, miR-30d, miR-144, miR-451a, miR-107, miR-125b, miR-143, and miR-720 is indicative that the subject has or is likely to develop multiple myeloma. In some embodiments of this aspect, an increased expression relative to the control level of miR-155 is indicative that the subject has or is likely to develop CLL or WM.

In another aspect, the disclosure features a method of determining if a subject has or is likely to develop multiple myeloma. The method involves identifying a subject who is suspected of having multiple myeloma, obtaining a biological sample from the subject, and determining from the biological sample that: (i) the subject has an altered level of one or more micro RNAs (miRs) compared to a control level, or (ii) the subject does not have an altered level of expression of the miRs compared to the control level. The one or more miRs are selected from the group consisting of miR-105-5p, miR-1909-3p, miR-378h, miR-520h, miR-613, miR-107, miR-190a, miR-380-3p, miR-525-3p, miR-614, miR-1179, miR-1911-5p, miR-381, miR-525-5p, miR-621, miR-1180, miR-193a-3p, miR-382-5p, miR-545-3p, miR-626, miR-1183, miR-193b-3p, miR-3934, miR-548a-3p, miR-627, miR-1185-5p, miR-194-5p, miR-409-3p, miR-548ad, miR-630, miR-1193, miR-195-5p, miR-411-5p, miR-548ag, miR-641, miR-1202, miR-1973, miR-422a, miR-548ah-5p, miR-642a-5p, miR-1205, miR-200a-3p, miR-431-5p, miR-548ai, miR-644a, miR-1208, miR-2053, miR-432-5p, miR-548aj-3p, miR-646, miR-1225-5p, miR-208a, miR-433, miR-548al, miR-647, miR-1228-3p, miR-208b, miR-4421, miR-548g-3p, miR-651, miR-1243, miR-2114-5p, miR-4443, miR-548i, miR-656, miR-1244, miR-211-5p, miR-4448, miR-548n, miR-658, miR-1245a, miR-2117, miR-4454, miR-548s, miR-662, miR-1245b-5p, miR-212-3p, miR-4458, miR-548t-5p, miR-663a, miR-1252, miR-215, miR-4461, miR-548u, miR-663b, miR-1253, miR-218-5p, miR-448, miR-548x-3p, miR-670, miR-125b-5p, miR-23c, miR-4488, miR-548z, miR-675-5p, miR-1264, miR-2682-5p, miR-449a, miR-549, miR-744-5p, miR-1265, miR-300, miR-449b-5p, miR-550a-5p, miR-759, miR-1268a, miR-301b, miR-450b-5p, miR-551a, miR-760, miR-1269a, miR-302a-3p, miR-451a, miR-553, miR-761, miR-1273d, miR-302b-3p, miR-4521, miR-556-5p, miR-764, miR-1275, miR-302f, miR-4532, miR-558, miR-766-3p, miR-1277-3p, miR-30e-5p, miR-4647, miR-564, miR-769-3p, miR-1279, miR-3131, miR-4741, miR-566, miR-769-5p, miR-1281, miR-31-5p, miR-4792, miR-567, miR-770-5p, miR-1286, miR-3164, miR-483-3p, miR-569, miR-874, miR-1290, miR-3168, miR-484, miR-570-3p, miR-876-3p, miR-1294, miR-3180, miR-487a, miR-572, miR-885-3p, miR-1295a, miR-3180-3p, miR-490-5p, miR-573, miR-890, miR-1297, miR-3184-5p, miR-491-3p, miR-574-3p, miR-891a, miR-130b-3p, miR-3185, miR-494, miR-575, miR-892a, miR-1321, miR-3196, miR-495, miR-577, miR-922, miR-1323, miR-3200-3p, miR-498, miR-578, miR-924, miR-133b, miR-330-3p, miR-499a-5p, miR-579, miR-935, miR-135a-5p, miR-330-5p, miR-499b-5p, miR-581, miR-938, miR-139-3p, miR-331-5p, miR-510, miR-585, miR-939, miR-141-3p, miR-3614-5p, miR-511, miR-586, miR-941, miR-143-3p, miR-363-3p, miR-514a-3p, miR-588, miR-95, miR-144-3p, miR-3690, miR-514b-5p, miR-590-3p, miR-99b-5p, miR-1470, miR-372, miR-517c-3p, miR-596, miR-375, miR-518b, miR-598, miR-151b, miR-376b, miR-519b-3p, miR-603miR-152, miR-376c, miR-519b-5p, miR-604, miR-1539, miR-378f, miR-520b, miR-605, let-7a-5p, let-7b-5p, let-7f-5p, let-7g-5p, let-7i-5p, miR-106a-5p, miR-17-5p, miR-106b-5p, miR-1246, miR-126-3p, miR-1285-3p, miR-130a-3p, miR-142-3p, miR-148b-3p, miR-150-5p, miR-15a-5p, miR-15b-5p, miR-181a-5p, miR-185-5p, miR-188-5p, miR-191-5p, miR-199a-3p, miR-199b-3p, miR-199a-5p, miR-19b-3p, miR-20a-5p, miR-20b-5p, miR-21-5p, miR-221-3p, miR-223-3p, miR-23a-3p, miR-24-3p, miR-26a-5p, miR-27b-3p, miR-297, miR-29b-3p, miR-30b-5p, miR-340-5p, miR-361-3p, miR-371a-3p, miR-374a-5p, miR-374b-5p, miR-548c-5p, miR-548p, miR-888-5p, miR-92a-3p, and miR-93-5p. An increased expression relative to the control level of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or one, two, three, four, five, six, seven, eight, nine, ten, or eleven, twelve, thirteen, fourteen, fifteen, sixteen, seventeen, eighteen, nineteen, or twenty of miR-105-5p, miR-1909-3p, miR-378h, miR-520h, miR-613, miR-107, miR-190a, miR-380-3p, miR-525-3p, miR-614, miR-1179, miR-1911-5p, miR-381, miR-525-5p, miR-621, miR-1180, miR-193a-3p, miR-382-5p, miR-545-3p, miR-626, miR-1183, miR-193b-3p, miR-3934, miR-548a-3p, miR-627, miR-1185-5p, miR-194-5p, miR-409-3p, miR-548ad, miR-630, miR-1193, miR-195-5p, miR-411-5p, miR-548ag, miR-641, miR-1202, miR-1973, miR-422a, miR-548ah-5p, miR-642a-5p, miR-1205, miR-200a-3p, miR-431-5p, miR-548ai, miR-644a, miR-1208, miR-2053, miR-432-5p, miR-548aj-3p, miR-646, miR-1225-5p, miR-208a, miR-433, miR-548al, miR-647, miR-1228-3p, miR-208b, miR-4421, miR-548g-3p, miR-651, miR-1243, miR-2114-5p, miR-4443, miR-548i, miR-656, miR-1244, miR-211-5p, miR-4448, miR-548n, miR-658, miR-1245a, miR-2117, miR-4454, miR-548s, miR-662, miR-1245b-5p, miR-212-3p, miR-4458, miR-548t-5p, miR-663a, miR-1252, miR-215, miR-4461, miR-548u, miR-663b, miR-1253, miR-218-5p, miR-448, miR-548x-3p, miR-670, miR-125b-5p, miR-23c, miR-4488, miR-548z, miR-675-5p, miR-1264, miR-2682-5p, miR-449a, miR-549, miR-744-5p, miR-1265, miR-300, miR-449b-5p, miR-550a-5p, miR-759, miR-1268a, miR-301b, miR-450b-5p, miR-551a, miR-760, miR-1269a, miR-302a-3p, miR-451a, miR-553, miR-761, miR-1273d, miR-302b-3p, miR-4521, miR-556-5p, miR-764, miR-1275, miR-302f, miR-4532, miR-558, miR-766-3p, miR-1277-3p, miR-30e-5p, miR-4647, miR-564, miR-769-3p, miR-1279, miR-3131, miR-4741, miR-566, miR-769-5p, miR-1281, miR-31-5p, miR-4792, miR-567, miR-770-5p, miR-1286, miR-3164, miR-483-3p, miR-569, miR-874, miR-1290, miR-3168, miR-484, miR-570-3p, miR-876-3p, miR-1294, miR-3180, miR-487a, miR-572, miR-885-3p, miR-1295a, miR-3180-3p, miR-490-5p, miR-573, miR-890, miR-1297, miR-3184-5p, miR-491-3p, miR-574-3p, miR-891a, miR-130b-3p, miR-3185, miR-494, miR- 575, miR-892a, miR-1321, miR-3196, miR-495, miR-577, miR-922, miR-1323, miR-3200-3p, miR-498, miR-578, miR-924, miR-133b, miR-330-3p, miR-499a-5p, miR-579, miR-935, miR-135a-5p, miR-330-5p, miR-499b-5p, miR-581, miR-938, miR-139-3p, miR-331-5p, miR-510, miR-585, miR-939, miR-141-3p, miR-3614-5p, miR-511, miR-586, miR-941, miR-143-3p, miR-363-3p, miR-514a-3p, miR-588, miR-95, miR-144-3p, miR-3690, miR-514b-5p, miR-590-3p, miR-99b-5p, miR-1470, miR-372, miR-517c-3p, miR-596, miR-375, miR-518b, miR-598, miR-151b, miR-376b, miR-519b-3p, miR-603miR-152, miR-376c, miR-519b-5p, miR-604, miR-1539, miR-378f, miR-520b, and miR-605; and/or a decreased expression relative to the control level of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or one, two, three, four, five, six, seven, eight, nine, ten, or eleven, twelve, thirteen, fourteen, fifteen, sixteen, seventeen, eighteen, nineteen, or twenty of let-7a-5p, let-7b-5p, let-7f-5p, let-7g-5p, let-7i-5p, miR-106a-5p, miR-17-5p, miR-106b-5p, miR-1246, miR-126-3p, miR-1285-3p, miR-130a-3p, miR-142-3p, miR-148b-3p, miR-150-5p, miR-15a-5p, miR-15b-5p, miR-181a-5p, miR-185-5p, miR-188-5p, miR-191-5p, miR-199a-3p, miR-199b-3p, miR-199a-5p, miR-19b-3p, miR-20a-5p, miR-20b-5p, miR-21-5p, miR-221-3p, miR-223-3p, miR-23a-3p, miR-24-3p, miR-26a-5p, miR-27b-3p, miR-297, miR-29b-3p, miR-30b-5p, miR-340-5p, miR-361-3p, miR-371a-3p, miR-374a-5p, miR-374b-5p, miR-548c-5p, miR-548p, miR-888-5p, miR-92a-3p, and miR-93-5p, is indicative that the subject has or is likely to develop multiple myeloma.

In another aspect, the disclosure features a method of determining the stage of a hematological malignancy. The method involves identifying a subject who has a hematological malignancy, obtaining a biological sample from the subject, and determining from the biological sample that: (i) the subject has an altered level of one or more micro RNAs (miRs) compared to the level in a control subject having an identified stage of the hematological malignancy, or (ii) the subject does not have an altered level of expression of the miRs compared to the control level. The one or more miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. If the subject has an altered level of one or more micro RNAs (miRs) compared to the control level, the subject is identified as likely to have a stage of hematological malignancy other than that of the control subject. If, however, the subject does not have an altered level of expression of the miRs compared to the control level, the subject is identified as likely to have the same stage of the hematological malignancy as the control subject. It is noted the comparison of the subject's level of one or more miRNAs can be to the level which is a mean of a population of control subjects having an identified stage of the hematological malignancy.

In some embodiments of this aspect, an increased level compared to the control level of one or more, two or more, three or more, or one, two, three or four of miR-450a, miR-30e, miR-125a, and miR-300, and/or a decreased level compared to the control subject of one or more, two or more, or one, two, or three of miR-185, miR-150, and miR-98 is indicative that the subject is in the MGUS stage of MM. In certain embodiments of this aspect, an increased level compared to the control subject of miR-107, or a decreased level compared to the control subject of one or more, two or more, three or more, four or more, five or more, six or more, seven or more, eight or more, nine or more, or one, two, three, four, five, six, seven, eight, nine, or ten of miR-92a, miR-28, miR-32, miR-548a, miR-939, miR-99a, miR-345, miR-125a, miR-587, and miR-323b is indicative that the subject has progressed to the SMM stage of MM. In some embodiments of this aspect, an increased level compared to the control level of one or more, two or more, or one, two, or three of miR-125b, miR-143, or miR-720, or a decreased level compared to the control subject of one or more, two or more, three or more, four or more, five or more, six or more, seven or more, or one, two, three, four, five, six, seven, or eight of miR-let-7g, miR-223, miR-150, miR-15a, miR-19b, miR-21, miR-let-7b, or miR-let-7c is indicative that the subject has progressed to symptomatic MM. In certain embodiments, an increased level compared to the control subject of miR-155 is indicative that the subject has one or more of: Waldenstrom's macroglobulinemia (WM), chronic lymphocytic leukemia (CLL), small lymphocytic lymphoma (SLL), or follicular lymphoma.

In certain embodiments of the above three aspects, the method further involves administering the subject with a treatment that ameliorates the hematological malignancy if the subject is identified as likely to have a hematological malignancy. The treatment will depend upon the nature and severity of the hematological malignancy. Thus, for example, if an miRNA is found expressed at a higher level than the control, anti-miRs (e.g. tiny locked nucleic acids (LNAs)) that target that miRNA can be administered to the subject. Conversely, for example, if an miRNA is found to be expressed at a lower level than the control, pri-miRs or pre-miRs of that miRNA can be administered to the subject.

In another aspect, the disclosure features a method of selecting a treatment regimen for a subject. The method involves identifying a subject who is suspected of having, or who has, a hematological malignancy or a stage of a hematological malignancy; obtaining a biological sample from the subject; and determining from the biological sample that: (i) the subject has an altered level of one or more miRs compared to the level in a control subject who does not have the hematological malignancy, or (ii) the subject does not have an altered level of the miRs compared to the control level. The one or more miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. If the subject is determined as having an altered level of one or more miRs compared to the level in a control subject who does not have the hematological malignancy, the method involves selecting and administering a treatment regimen for the subject that ameliorates the hematological malignancy or the stage of the hematological malignancy. If, however, the subject is determined as having an altered level of one or more miRs compared to the level, the method involves not selecting and administering a treatment regimen for the subject that ameliorates the hematological malignancy or the stage of the hematological malignancy. It is noted the comparison of the subject's level of one or more miRs can be to the level which is a mean of a population of control subjects having an identified stage of the hematological malignancy.

In some embodiments of this aspect, a subject with an increased level of miR-155 compared to the control subject is administered a treatment regimen comprising everolimus and an anti-CD20 antibody (e.g., rituximab). In some embodiments of this aspect, a subject with an increased level of miR-155 compared to the control subject is administered a treatment regimen comprising everolimus and a proteasome inhibitor (e.g., bortezomib). In both of these embodiments, the subject may further be administered with anti-miR-155 (e.g., a tiny LNA). In some embodiments, a subject with an increased level of an miR compared to the control level is administered an anti-miR (e.g., a tiny LNA) that targets the miR that is expressed at an increased level. In some embodiments, a subject with a decreased level of an miR compared to the control level is administered a pri-miR or a pre-miR that increases the expression of the miR that is expressed at decreased level. In some embodiments, the method involves determining the expression level of the one or more miRs after completion of the treatment regimen. In these methods, an altered expression of the one or more miRs compared to the control subject is indicative that the subject has or will have early relapse, and lack of an altered expression of the one or more miRs compared to the control subject is indicative that the treatment regimen was effective.

The following embodiments apply to all of the above aspects and embodiments thereof. In some embodiments, the biological sample is collected and/or stored in tubes with EDTA. In certain embodiments, the biological sample is plasma. In some embodiments, the biological sample is exosome-enriched plasma. In certain embodiments, the method involves isolating circulating exosomes from the subject (e.g., from the biological sample of the subject) and obtaining miRNA from the circulating exosomes. In certain embodiments the method involves normalizing the level of miRs using an internally spiked control. In some embodiments, the hematological malignancy is a low grade B cell malignancy selected from the group consisting of multiple myeloma (MM), Waldenstrom's macroglobulinemia (WM), Chronic lymphocytic leukemia (CLL), small lymphocytic lymphoma (SLL), and follicular lymphoma. In some embodiments, the subject is a human. In some embodiments, the determining step is performed by quantitative RT-PCR. In some embodiments, the determining step is performed by the nCounter miRNA expression assay. In certain embodiments, the determining step is performed by Taqman miRNA profiling.

In yet another aspect, the disclosure features a method of treating a subject having or likely to have a hematological malignancy or a stage of a hematological malignancy. The method involves administering to the subject an effective amount of one or more, two or more, three or more, four or more, five or more, six or more, seven or more, eight or more, nine or more, ten or more, or one, two, three, four, five, six, seven, eight, nine, ten, eleven, or twelve anti-miRs (e.g., tiny LNAs) of the following miRs: miR-450a, miR-30e, miR-125a, miR-300, miR-30d, miR-144, miR-451a, miR-107, miR-125b, miR-143, miR-720, and miR-155, and/or administering to the subject an effective amount of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or one, two, three, four, five, six, seven, eight, nine, ten, eleven, twelve, thirteen, fourteen, fifteen, sixteen, seventeen, eighteen, nineteen, or twenty pre-miRs of the following miRs: miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c.

In certain embodiments of this aspect, the method involves administering to a subject having or likely to have WM or CLL an effective amount of an anti-miR to miR-155. In some embodiments of this aspect, the method involves administering a subject having or likely to have MM or a stage of MM an effective amount of one or more, two or more, three or more, four or more, five or more, six or more, seven or more, eight or more, nine or more, ten or more, or one, two, three, four, five, six, seven, eight, nine, ten, or eleven anti-miRs (e.g., tiny LNAs) of the following miRs: miR-450a, miR-30e, miR-125a, miR-300, miR-30d, miR-144, miR-451a, miR-107, miR-125b, miR-143, and miR-720, and/or administering to the subject an effective amount of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or one, two, three, four, five, six, seven, eight, nine, ten, eleven, twelve, thirteen, fourteen, fifteen, sixteen, seventeen, eighteen, nineteen, or twenty pre-miRs of the following miRs: miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. In some embodiments of this aspect, the method involves administering to the subject exosomes from a different subject who does not have a hematological malignancy. In a specific embodiment, the exosomes are from an HLA-matched individual. In some embodiments, the treated subject is a human subject.

In another aspect, the disclosure provides a method that involves identifying a subject who is suspected of having a hematological malignancy; obtaining a biological sample from the subject; and determining from the biological sample that: (i) the subject has an altered level of one or more, two or more, three or more, four or more, five or more, six or more, seven or more, eight or more, nine or more, ten or more, or one, two, three, four, five, six, seven, eight, nine, or ten micro RNAs (miRs) compared to a control level, or (ii) the subject does not have an altered level of expression of the miRs compared to the control level. The one or more, two or more, three or more, four or more, five or more, six or more, seven or more, eight or more, nine or more, ten or more, or one, two, three, four, five, six, seven, eight, nine, or ten miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. The method involves treating the subject with an antimiR that targets the miR (i.e., to reduce or abolish the miRs function) that is expressed at a higher level than the control level, or a pre-miR of the miR that is expressed at a lower level than the control level, or not treating the subject if the subject does not have an altered level of expression of the miRs compared to the control level.

In a further aspect, the disclosure features a method of treating a subject having or likely to have WM or CLL, the method comprising administering the subject with everolimus in combination with an anti-CD20 antibody and/or a proteasome inhibitor.

In certain embodiments of this aspect, the anti-CD20 antibody is rituximab, ofatumumab, veltuzumumab, ocrelizumab, AME-133v, PRO131921, or GA-101. In a specific embodiment, the anti-CD20 antibody is rituximab. In another embodiment, the subject is administered TRU-015 with everolimus. In some embodiments, the proteasome inhibitor is bortezomib, disulfiram, epigallocatechin-3-gallate, salinosporamide A, carfilzomib, ONX 0912, CEP-18770, and MLN9708. In a particular embodiment, the proteasome inhibitor is bortezomib. In all of these embodiments, the subject can also be further administered anti-miR-155. In all of these embodiments, the subject can also be further administered with one or more of: any other inhibitor that targets the PI3K pathway (e.g., perifosine, CAL101, PX-866, BEZ235, SF1126, INK1117, IPI-145, GDC-0941, BKM120, XL147, XL765, Palomid 529, GSK1059615, ZSTK474, PWT33597, IC87114, TG100-115, CAL263, P1-103, GNE-477, CUDC-907, AEZS-136), agents that target the MYD88 mutation, and/or BTK inhibitors (e.g., ibrutinib, AVL-292, PCI-32765, PCYC-04753, Imidazo[1,5-a]quinoxalines). In all of these embodiments, the subject can be a human subject.

In all aspects relating to treatment of a subject, the treatment may also include administration of an agent that blocks or reduces the activity of one or more, two or more, three or more, or one, two, three or four of the following proteins: IL-6, CCL2./MCP1, fibronectin, and junction plakoglobin. In one embodiment, the agent that blocks or reduces activity is an antibody. In one embodiment, the antibody is an anti-IL-6 antibody.

In another aspect, the disclosure features a composition comprising a mixture of two or more of the following four anti-miRs: anti-miR-450a, anti-miR-30e, anti-miR-125a, and anti-miR-300.

In another aspect, the disclosure features a composition comprising a mixture of two or more of the following five anti-miRs: anti-mir-30d, anti-anti-miR-30e, anti-miR-144, anti-miR-451a, and anti-miR-107.

In a further aspect, the disclosure features a composition comprising a mixture of two or more of the following three anti-miRs: anti-mir-125b, anti-anti-miR-143, and anti-miR-720.

In another aspect, the disclosure features a composition comprising a mixture of two or more of the following three pre-miRs: miR-185, miR-150, and miR-98.

In another aspect, the disclosure features a composition comprising a mixture of two or more of the following ten pre-miRs: miR-92a, miR-28, miR-32, miR-548a, miR-939, miR-99a, miR-345, miR-125a, miR-587, and miR-323b.

In yet another aspect, the disclosure features a composition comprising a mixture of two or more of the following eight pre-miRs: miR-let-7g, miR-223, miR-150, miR-15a, miR-19b, miR-21, miR-let-7b, or miR-let-7c.

In a further aspect, the disclosure features a composition comprising anti-miR-155 and everolimus. In some embodiments of this aspect, the composition also includes an anti-CD20 antibody. In a particular embodiment, the anti-CD20 antibody is rituximab. In some embodiments of this aspect, the composition further includes a proteasome inhibitor. In a particular embodiment, the proteasome inhibitor is bortezomib.

In all aspects drawn to compositions or their use, the compositions can include a pharmaceutically acceptable carrier. In addition, the anti-miRs, pri-miRs, or pre-miRs can be modified to increase half-life, stability and in vivo delivery. In certain embodiments, the anti-miRs, pri-miRs, or pre-miRs are 2'-O-Me modified, 2'-O-methoxyethyl modified, 2'F-fluoro modified or locked nucleic acid (LNA) modified. In certain embodiments the backbones of the anti-miRs, pri-miRs, or pre-miRs have phosphorothioate (PS) linkages. In other embodiments, the anti-miRs, pri-miRs, or pre-miRs are LNA/DNA, 2'-F/MOE, or LNA/2'-O-Me mixmers with or without PS ends. In certain embodiments, the anti-miR is a tiny LNA.

By "a control level" is meant a level of an miRNA of interest from any one of: a control single subject without the disease/hematological malignancy; a predetermined mean of a population of control subjects; or a sample from a subject obtained before any symptoms appeared.

A subject "suspected of having a hematological malignancy" is one having one or more symptoms of the hematological malignancy.

As used herein, a subject "at risk of developing a hematological malignancy" is a subject that has a predisposition to develop the hematological malignancy (i.e., a genetic predisposition to develop the hematological malignancy).

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
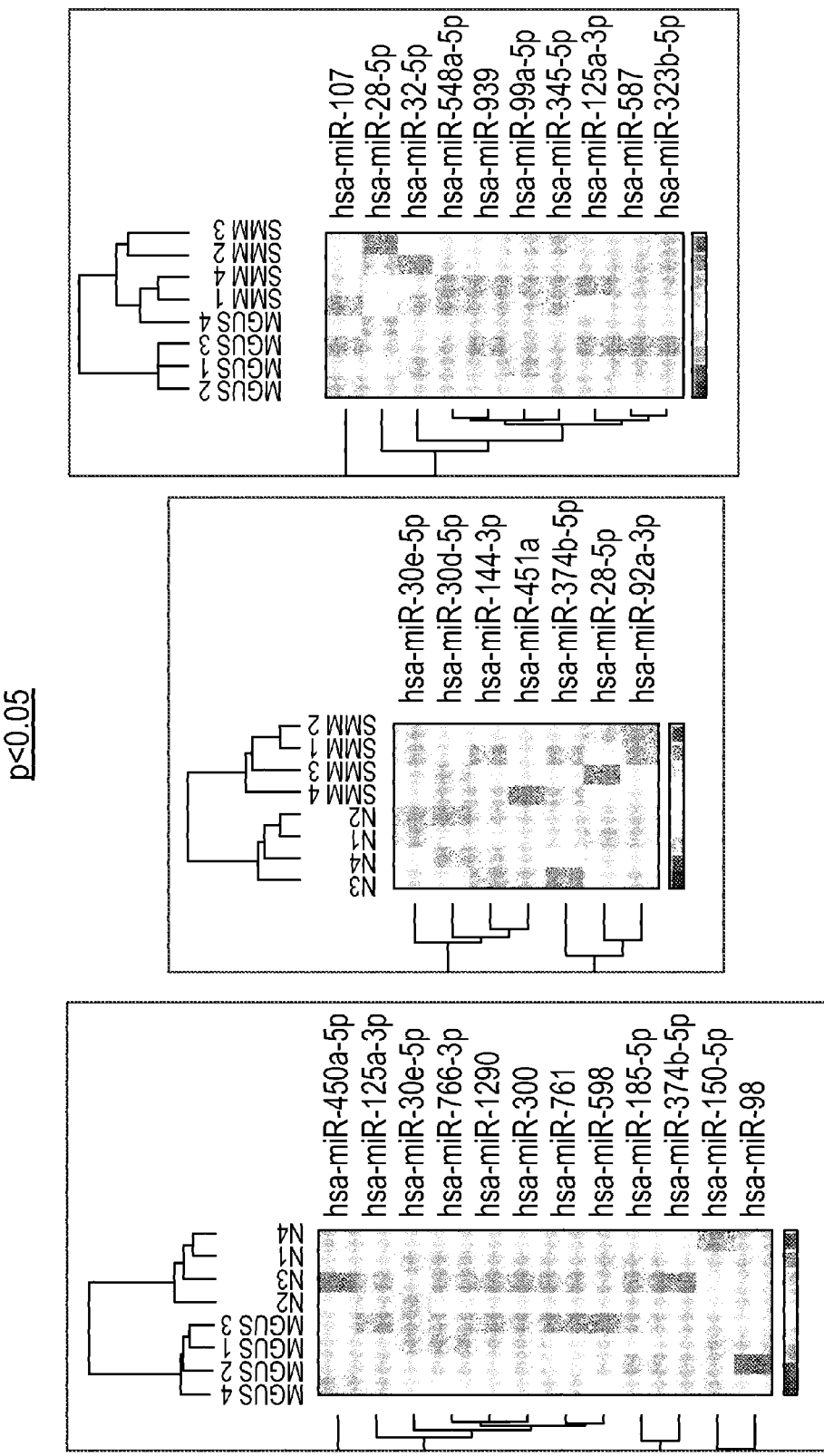
FIG. 1 is a heatmap depicting the most differentially expressed miRNAs present in exosomes obtained from MGUS versus normal control (N) (left panel), or normal control versus Smoldering MM (SMM) (middle panel) or Smoldering MM versus MGUS (right panel). The intensity of color in each cell correlates with the degree of increase or decrease in expression.
Figure 2:
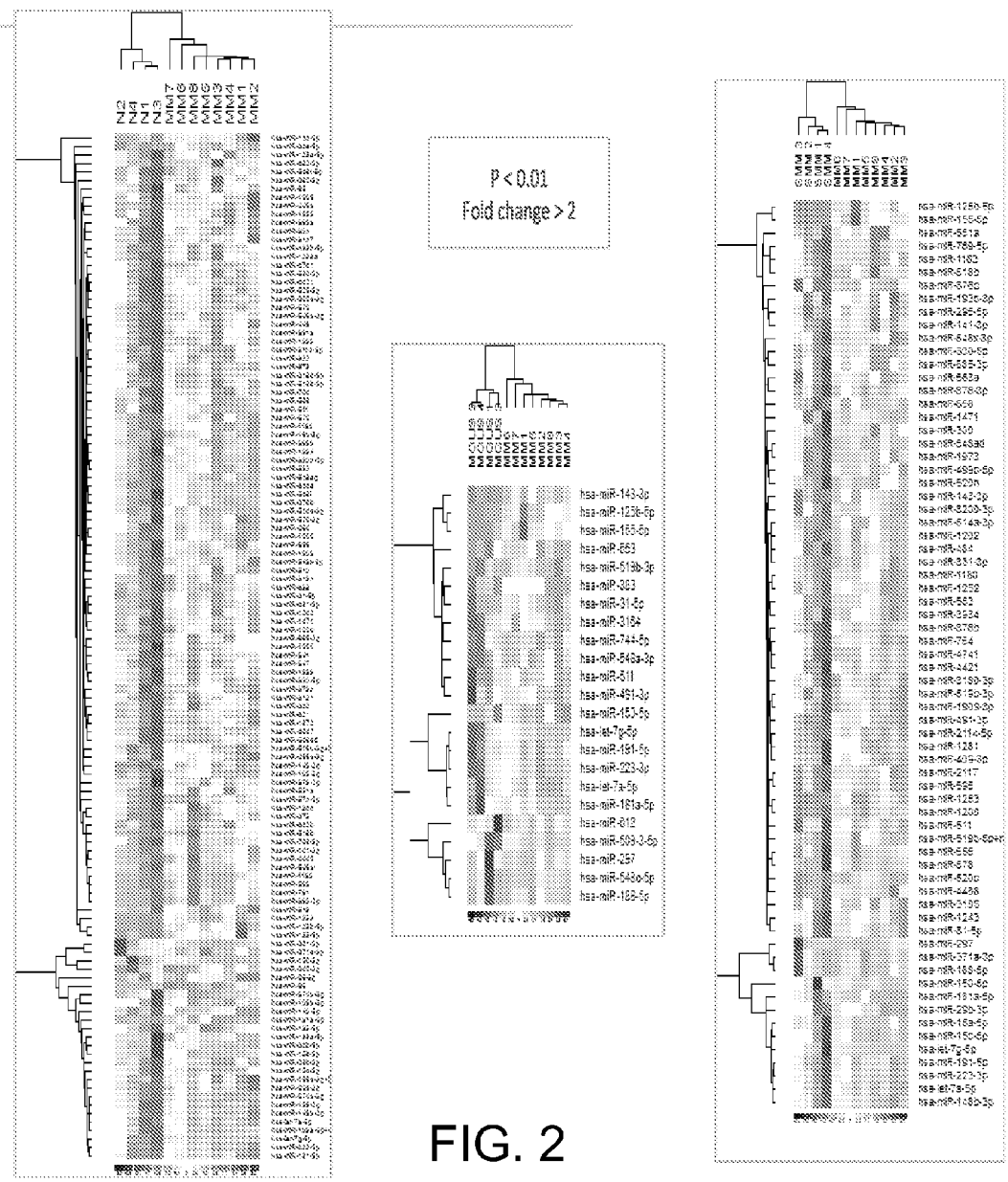
FIG. 2 is a heatmap depicting the miRNAs that are differentially expressed in exosomes from patients with myeloma compared to normal control (left panel), or MGUS (middle panel) or Smoldering MM (SMM) (right panel). The intensity of color in each cell correlates with the degree of increase or decrease in expression. The unsupervised clustering shows that these samples can be differentiated from each other based on the miRNA profiling sets. This is critical for MGUS and SMM to show that they have a different miRNA profile compared to more advances cases of symptomatic MM. An enlarged version of the left panel is provided as FIG. 21.

The present disclosure features, in part, compositions, methods of diagnosis, methods of staging, methods of prognosis, and methods of treatment for subjects having, suspected of having, or predisposed to developing hematological malignancies such as, but not limited to, plasma cell dyscrasias and low-grade lymphomas. Various aspects of the invention are described below.

Hematological Malignancies

1. Plasma Cell Dyscrasias

Plasma cell dyscrasias are cancers of the plasma cells. They are produced as a result of malignant proliferation of a monoclonal population of plasma cells that may or may not secrete detectable levels of a monoclonal immunoglobulin or paraprotein commonly referred to as M protein. Non-limiting examples of plasma cell dyscrasias include monoclonal gammopathy of undermined significance (MGUS), multiple myeloma (MM), Waldenström macroglobulinemia (WM), amyloidosis (AL), plasmacytoma syndrome (e.g., solitary plasmacytoma of bone, extramedullary plasmacytoma), polyneuropathy, organomegaly, endocrinopathy monoclonal gammopathy and skin changes syndrome (POEMS), light chain deposition disease, and heavy-chain disease. MGUS, smoldering MM, and symptomatic MM represent a spectrum of the same disease.

A. Myeloma a. Monoclonal Gammopathy of Undermined Significance (MGUS)

MGUS is characterized by a serum monoclonal protein, <30 g/L, <10% plasma cells in the bone marrow, and absence of end-organ damage (Kyle R. A. et al., *Leukemia*, 23:3-9 (2009)). Recent studies suggest that an asymptomatic MGUS stage consistently precedes multiple myeloma (MM) (Landgren O. et al., *Blood*, 113:5412-7 (2009)). MGUS is present in 3% of persons >50 years and in 5%>70 years of age. The risk of progression to MM or a related disorder is 1% per year (Kyle R. A. et al., *Clin. Lymphoma Myeloma*, 6:102-14 (2005)). Patients with risk factors consisting of an abnormal serum free light chain ratio, non-immunoglobulin G (IgG) MGUS, and an elevated serum M protein >/=15 g/l had a risk of progression at 20 years of 58%, compared with 37% among patients with two risk factors, 21% for those with one risk factor, and 5% for individuals with no risk factors (Rajkumar S. V., *Br J. Haematol.*, 127:308-10 (2004)). The cumulative probability of progression to active MM or amyloidosis was 51% at 5 years, 66% at 10 years and 73% at 15 years; the median time to progression was 4.8 years (Rajkumar S. V., *Blood Rev.*, 21:255-65, (2007)).

b. Smoldering Multiple Myeloma (SMM)

SMM also known as asymptomatic MM is characterized by having a serum immunoglobulin (Ig) G or IgA monoclonal protein of 30 g/L or higher and/or 10% or more plasma cells in the bone marrow but no evidence of end-organ damage. A study of the natural history of SMM suggests that there are 2 different types: evolving smoldering MM and non-evolving Smoldering MM (Dimopoulos M. et al., *Leukemia*, 23(9):1545-56 (2009)). Evolving SMM is characterized by a progressive increase in M protein and a shorter median time to progression (TTP) to active multiple myeloma of 1.3 years. Non-evolving SMM has a more stable M protein that may then change abruptly at the time of progression to active multiple myeloma, with a median TTP of 3.9 years.

c. Symptomatic or Active Multiple Myeloma (MM)

Symptomatic or active MM is characterized by any level of monoclonal protein and the presence of end-organ damage that consists of the CRAB criteria (hypercalcemia, renal insufficiency, anemia, or bone lesions) (Kyle R. A. et al., *Leukemia*, 23:3-9 (2009)). MM is a plasma cell malignancy that characteristically involves extensive infiltration of bone marrow (BM), with the formation of plasmacytomas, as clusters of malignant plasma cells inside or outside of the BM milieu (Kyle R. A. et al., *N Engl. J. Med.*, 351:1860-73 (2004)). Consequences of this disease are numerous and involve multiple organ systems. Disruption of BM and normal plasma cell function leads to anemia, leukopenia, hypogammaglobulinemia, and thrombocytopenia, which variously result in fatigue, increased susceptibility to infection, and, less commonly, increased tendency to bleed. Disease involvement in bone creates osteolytic lesions, produces bone pain, and may be associated with hypercalcemia (Kyle R. A. et al., *Blood*, 111:2962-72 (2008)).

d. Evaluation of Suspected or Documented Myeloma

The initial evaluation of a suspected monoclonal gammopathy includes both serum and urine protein electrophoresis with immunofixation to identify and quantify the M protein. The majority of patients are expected to have a detectable M protein, but approximately 1-3% can present with a non-secretory myeloma that does not produce light or heavy chains. True non-secretory myeloma is thus rare, not least because, with the availability of serum free light chain testing, it is recognized that M protein is present. The most common M protein is IgG, followed by IgA, and light-chain-only disease. IgD and IgE are relatively uncommon and can be more difficult to diagnose because their M spikes are often very small. Up to 20% of patients will produce only light chains, which may not be detectable in the serum because they pass through the glomeruli and are excreted in the urine.

The standard evaluation of a documented monoclonal gammopathy includes a complete blood count with differential, calcium, serum urea nitrogen, and creatinine. Serum free light chain testing is also a useful diagnostic test (Piehler A. P. et al., *Clin. Chem.*, 54:1823-30 (2008)). Bone disease is best assessed by skeletal survey. Bone scans are not a sensitive measure of myelomatous bone lesions because the radioisotope is poorly taken up by lytic lesions in MM, as a result of osteoblast inhibition. Magnetic resonance imaging (MRI) is useful for the evaluation of solitary plasmacytoma of bone and for the evaluation of paraspinal and epidural components. 18F-FDG Positron Emission Tomography (PET)/CT scans are more sensitive in the detection of active lesions in the whole body (Fonti R. et al., *J. Nucl. Med.*, 49:195-200 (2008)). A bone marrow aspiration and biopsy are helpful to quantify the plasma cell infiltrate and adds important prognostic information with cytogenetic evaluation, including fluorescent in situ hybridization (FISH). Additional prognostic information can be obtained with serum $\beta_2$-microglobulin ($\beta_2$M) and C-reactive protein (CRP).

e. Staging and Prognostic Factors for Myeloma

The criteria for the diagnosis of MM, SMM, and MGUS are detailed in Table 1. Distinction among these entities is important for making treatment decisions and prognostic recommendations.

TABLE 1

| Disorder | Disease definition |
| --- | --- |
| MGUS | Serum monoclonal protein level <3 g/dL, bone marrow plasma cells 10%, and absence of end-organ damage, such as lytic bone lesions, anemia, hypercalcemia, or renal failure, that can be attributed to a plasma cell proliferative disorder. |
| SMM | Serum monoclonal protein (IgG or IgA) level ≥3 g/dL and/or bone marrow plasma cells ≥10%, absence of end-organ damage, such as lytic bone lesions, anemia, hypercalcemia, or renal failure that can be attributed to a plasma cell proliferative disorder. |
| MM | Bone marrow plasma cells ≥10%, presence of serum and/or urinary monoclonal protein (except in patients with true nonsecretory multiple myeloma), plus evidence of lytic bone lesions, anemia, hypercalcemia, or renal failure that can be attributed to the underlying plasma cell proliferative disorder. |
| Solitary plasmacytoma | Biopsy-proven solitary lesion of bone or soft tissue with evidence of clonal plasma cells, normal skeletal survey, and MRI of spine and pelvis, and absence of end-organ damage, such as anemia, hypercalcemia, renal failure, or additional lytic bone lesions, that can be attributed to a plasma cell proliferative disorder |

Several staging systems exist. The most widely used myeloma staging system since 1975 has been the Durie-Salmon, in which the clinical stage of disease is based on several measurements including levels of M protein, serum hemoglobin value, serum calcium level, and the number of bone lesions. The International Staging System (ISS), developed by the International Myeloma Working Group is now also widely used (Greipp P. R. et al., *J. Clin. Oncol.*, 23:3412-20 (2005)). ISS is based on two prognostic factors: serum levels of $\beta2M$ and albumin, and is comprised of three stages: $\beta2M$ 3.5 mg/L and albumin 3.5 g/dL (median survival, 62 months; stage I); $\beta2M$<3.5 mg/L and albumin<3.5 g/dL or $\beta2M$ 3.5 to <5.5 mg/L (median survival, 44 months; stage II); and $\beta2M$ 5.5 mg/L (median survival, 29 months; stage III). With an increased understanding of the biology of myeloma, other factors have been shown to correlate well with clinical outcome and are now commonly used. For example, cytogenetic abnormalities as detected by FISH techniques have been shown to identify patient populations with very different outcomes. For instance, loss of the long arm of chromosome 13 is found in up to 50% of patients and, when detected by metaphase chromosome analysis, is associated with poor prognosis. In addition, a hypodiploid karyotype 13 t(4; 14), and—17p13.1 is typically associated with poor outcome, while the t(11; 14) and hypodiploidy are associated with improved survival (Kyrtsonis M. C. et al., *Semin. Hematol.*, 46:110-7, (2009)).

f. Current Treatment Strategies for MM

Frontline therapy for symptomatic MM includes either conventional chemotherapy or high-dose chemotherapy (HDT) supported by autologous or allogeneic stem cell transplantation (SCT), depending on patient characteristics such as performance status, age, availability of a sibling donor, comorbidities, and, in some cases, patient and physician preferences. Other treatments include: bortezomib, thalidomide, lenalidomide, dexamethasone, cyclophosphamide, melphalan, and stem cell transplant. For a patient under 70 years of age, autologous stem cell transplant is proposed after induction.

Response to therapy is commonly measured by a reduction in M protein levels in serum and/or urine and the reduction in size or disappearance of plasmacytomas. The international uniform response criteria for MM have expanded upon the European Group for Blood and Marrow Transplantation criteria to provide a more comprehensive evaluation system (Durie B. G. et al., *Leukemia*, 20:1467-73 (2006)). Importantly, achievement of response has been associated with improved survival in SCT trials with high-dose therapy. Similarly, TTP has been shown to be an important surrogate for improved survival. Despite high response rates to frontline therapy, virtually all patients eventually relapse. Thus, research efforts are needed on identifying better frontline therapies to enhance and prolong response, reduce the rate of relapse, and improve the efficacy of treatment at relapse. Table 2 shows the international uniform response criteria for MM.

TABLE 2

| Response Subcategory | Response Criteria |
|---|---|
| CR | Negative immunofixation on the serum and urine and disappearance of any soft tissue plasmacytomas and ≤5% plasma cells in bone marrow |
| sCR | CR as described above, plus: normal free light chain (FLC) ratio and absence of clonal cells in bone marrow by immunohistochemistry or immunofluorescence |
| VGPR | Serum and urine M-protein detectable by immunofluorescence but not on electrophoresis or 90% or greater reduction in serum M-protein plus urine M-protein level <100 mg per 24 hours |
| PR | ≥50% reduction of serum M-protein and reduction in 24-h urinary M-protein by ≥90% or to <200 mg per 24 h If the serum and urine M-protein are unmeasurable, a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required. |
| SD | Not meeting criteria for CR, VGPR, PR or progressive disease |

Abbreviations: CR, complete response; sCR, stringent complete response; VGPR, very good partial response; FLC, free light chain; PR, partial response; SD, stable disease.

B. Lymphoplasmacytic Lymphoma

Waldenstrom's macrogloubulinemia (WM), termed lymphoplasmacytic lymphoma in the World Health Organization classification, is an indolent lymphoid malignancy composed of mature plasmacytoid lymphocytes that produce monoclonal IgM (Leleu X. et al., *Cancer Leu.*, 270: 95-107 (2008)). The disease affects predominantly older patients, who present with anemia, lymphadenopathy, purpura, splenomegaly, elevated serum viscosity, neurologic signs and symptoms, or combinations of these findings. Lytic bone lesions are typically absent. The lymphoma cells may express a variety of markers, including CD5, CD19, CD20, CD38, and surface or cytoplasmic Ig. Symptoms may be due to tumor infiltration (marrow, spleen, or lymph nodes), circulating IgM macroglobulin (hyperviscosity, cryoglobulinemia, or cold agglutinin hemolytic anemia), and tissue deposition of IgM or other proteins (neuropathy, glomerular disease, and/or amyloid).

Asymptomatic patients should be observed. Patients with a disease-related hemoglobin level <10 g/L, platelet count<100×10(9)/L, bulky adenopathy or organomegaly, symptomatic hyperviscosity, peripheral neuropathy, AL, cryoglobulinemia, cold agglutinin disease, or evidence of disease transformation should be considered for therapy (Morel P. et al., *Blood*, 113(18):4163-70 (2009). Plasmapheresis should be evaluated for symptomatic hyperviscosity.

WM is divided into stages of the disease based on the International Prognostic Scoring System for Waldenstrom's (Morel et al., *Blood*, 113(18):4163-70(2009). The scoring system (points) considers factors such as age (more than 65); Hemoglobin level (less than 11.5); platelet count (100 or less); Beta-2-microglobulin (more than 3 mg/L); and Monoclonal IgM level (more than 7 g/dL). An individual is at low risk if his/her age is less than 65 and has no more than one point; an individual is at intermediate risk if his/her age is 65 or greater and has two points; an individual is at high risk if he/she has at least three points.

Options for therapy for newly diagnosed patients with WM include the use of rituximab as monotherapy or in combination with cyclophosphamide, dexamethasone, fludarabine, Chlorambucil, nucleoside analog, bortezomib, or thalidomide. In addition, WM patients can be provided an autologous stem cell transplant.

2. Low-Grade Lymphomas

The low grade lymphomas are a diverse group, the most common of which are small lymphocytic lymphoma (SLL) and chronic lymphocytic leukemia (CLL). Other examples of such lymphomas include lymphoplasmacytic lymphoma and various types of marginal zone lymphomas (e.g., lymphomas of mucosa-associated lymphoid tissue).

a. SLL and CLL

Small lymphocytic lymphoma (SLL) is almost identical both morphologically and clinically to chronic lymphocytic leukemia (CLL). When SLL presents primarily with blood and bone marrow involvement, it is called CLL.

In the lymph nodes of SLL patients sheets of small lymphoid cells are seen that tend to flood the lymph node and its sinuses without destroying them. These cells have scant cytoplasm, rounded nuclei, darkly clumped chromatin, and inconspicuous nuclei, and in isolation are almost indistinguishable from benign small lymphocytes. SLL cells aberrantly express T-cell antigens CD5 and CD43, in addition to another characteristic antigen, CD23. Some SLL subjects show trisomy 12. A variant of SLL called "atypical SLL" fails to express CD23, but expresses bright CD20 and surface light chain and FMC7. Often patients presenting with atypical SLL have trisomy 12. Atypical SLL may follow a slightly more aggressive course than SLL.

SLL patients are elderly (median age 60 years) and usually present with diffuse lymphadenopathy and some degree of marrow and peripheral blood involvement (Stage IV disease). Mild to moderate splenomegaly is common Constitutional ("B") symptoms are seen in 15%. Many patients have decreased normal antibodies (hypogammaglobulinemia) leading to infections. Patients may also have anemia or thrombocytopenia from marrow infiltration or more rarely from immune hemolysis. In addition, a monoclonal serum immunoglobulin (M-component) can be identified in almost half the cases.

SLL and CLL have at least two different systems for staging the disease. These are the Rai system (used more often in the United States) and the Binet system (used more widely in Europe). The Rai system divides CLL into 5 stages:

Rai stage 0: The blood lymphocyte count is too high, usually defined as over 10,000 lymphocytes/mm³ of blood (this is called lymphocytosis). Some doctors will diagnose CLL if the count is over 5,000/mm3 and the cells all have the same chemical pattern on special testing. The lymph nodes, spleen, and liver are not enlarged and the red blood cell and platelet counts are near normal.

Rai stage I: Lymphocytosis plus enlarged lymph nodes. The spleen and liver are not enlarged and the red blood cell and platelet counts are near normal.

Rai stage II: Lymphocytosis plus an enlarged spleen (and possibly an enlarged liver), with or without enlarged lymph nodes. The red blood cell and platelet counts are near normal.

Rai stage III: Lymphocytosis plus anemia (too few red blood cells), with or without enlarged lymph nodes, spleen, or liver. Platelet counts are near normal.

Rai stage IV: Lymphocytosis plus thrombocytopenia (too few blood platelets), with or without anemia, enlarged lymph nodes, spleen, or liver.

For practical purposes, doctors separate the Rai stages into low-, intermediate-, and high-risk groups when determining treatment options.

Stage 0 is considered low risk.

Stages I and II are considered intermediate risk.

Stages III and IV are considered high risk.

In the Binet staging system, CLL/SLL is classified by the number of affected lymphoid tissue groups (neck lymph nodes, groin lymph nodes, underarm lymph nodes, spleen, and liver) and by whether or not the patient has anemia (too few red blood cells) or thrombocytopenia (too few blood platelets).

Binet stage A: Fewer than 3 areas of lymphoid tissue are enlarged, with no anemia or thrombocytopenia.

Binet stage B: 3 or more areas of lymphoid tissue are enlarged, with no anemia or thrombocytopenia.

Binet stage C: Anemia and/or thrombocytopenia are present.

SLL and CLL are indolent but relentless, with median survivals of almost a decade. Although the slowly proliferating cells are sensitive to chemotherapeutic agents, chemotherapy is almost never curative and relapse inevitably follows. Therapy tends to be low-intensity: single alkylator therapy such as chlorambucil, fludarabine, bendamustine; or combination therapy with cyclophosphamide/vincristine/prednisone. CLL can also be treated with rituximab or alemtuzumab. Allogeneic stem cell transplant is recommended for young patients with p53 mutation or refractory/relapsed within 2 years of first line chemotherapy.

b. Marginal Zone Lymphomas

There are three types of marginal zone lymphomas: nodal, extra-nodal, and splenic. These lymphomas usually display a variety of cell types, including small lymphocytes, centrocyte-like cells, monocytoid B-cells, marginal zone cells, plasma cells, and infrequent larger cells. Occasionally a vaguely nodal pattern can be discerned, most often produced by residual benign germinal centers either surrounded or infiltrated by lymphoma cells. When the lymphomas occur near epithelium, they tend to invade it destructively to produce characteristic lympho-epithelial lesions.

Marginal zone lymphoma cells express monoclonal surface immunoglobulin and pan-B-cell antigens. They are usually negative for CD5, CD10, CD23, and CD43 and show no characteristic chromosomal translocations.

Taken as a whole, low grade lymphomas (diffuse and follicular, B-cell and T-cell) make up from 20-45% of lymphomas and have a median survival of 5 years or more. While combination chemotherapy usually secures a complete or partial response, the relapse rate is 10-15% per year thereafter.

microRNAs that are Differentially Expressed in Hematological Malignancies microRNAs (miRs) are single-stranded RNA molecules of about 21-24 nucleotides in length that regulate gene expression. miRs are transcribed from DNA, but the miRs are not translated into protein (i.e., they are non-coding RNAs). Instead, each primary transcript (a pri-miR) is processed into a short stem-loop structure called a pre-miRNA and finally into a linear functional miRNA (generally a 22 base pair piece of RNA). Mature miRNA molecules are either fully or partially complementary to regions (typically in the 3'-UTR, surrounding the stop codon, or within the 5'-UTR) of one or more messenger RNA (mRNA) molecules. They regulate post-transcriptional gene expression by e.g., blocking translation of target mRNAs, reducing stability of the target mRNA, or by accelerating their degradation. Generally, if an miR is fully complementary to a target region of an mRNA, the miR accelerates the targeted degradation of the mRNA. If, however, an miR is partially complementary to a target region of an mRNA, the miR simply blocks the translation of the mRNA. miRNAs regulate the gene expression by binding to the mRNA. The so-called "seed" sequence is essential for the binding of an miRNA to an mRNA. The region of the miRNA that is complementary to the mRNA and that generally encompasses the 5' bases 2-7 of the microRNA is the microRNA "seed region." Even though base pairing of miRNA and its target mRNA does not need to match perfectly, the "seed sequence" has to be perfectly complementary for the miRNA to regulate the mRNA. One miRNA can target many different sites on the same mRNA or on many different mRNAs. To date, more than 700 human miRs have been identified, regulating an estimated 30% of all human genes. miRs play important roles in several biological processes such as cell proliferation, apoptosis, developmental timing, and DNA repair.

miRs can be transported between cells and in the circulatory system by exosomes. Exosomes are small vesicles (50-100 nm) of endocytic origin, which are released into the extra-cellular milieu by several cell types (van Niel G. et al., *J. Biochem.*, 140:13-21, (2006); Pan B. T. et al., *Cell*, 33:967-78 (1983); Thery C. et al., *J. Cell Biol.*, 147:599-610 (1999); Raposo G. et al., *J. Exp. Med.*, 183:1161-72, (1996); Blanchard N. et al., *J. Immunol.*, 168:3235-41 (2002); van Niel G. et al., *Gastroenterol.*, 121:337-49 (2001); Mears R. et al., *Proteomics*, 4:4019-31 (2004); and Raposo G. et al., *Mol. Biol. Cell*, 8:2631-45 (1997)) under physiological and pathological conditions, including antigen presentation, transmission of infectious agents, and tumorigenesis (Thery C. et al., *Nat. Rev. Immunol.*, 9:581-93, (2009); and Giri P. K. et al., *PloS One* 3:e2461 (2008)). Cell-to-cell communication is partially mediated by exosomes. The role of exosomes has been shown in tumor progression, due to their ability to carry and transfer microRNAs (miRNAs) to the recipient cells. The role of exosomes in tumor progression is due to the ability of tumor cell-derived exosomes to modulate and mold the host microenvironment, thereby promoting tumor cell growth and disease progression.

In the present disclosure, exosomes and certain miRNAs are shown to have roles in the pathogenesis of hematologic malignancies. Some miRNAs are differentially expressed in tumor cells and/or exosomes and/or in the plasma of subjects having, or suspected of having, a hematological malignancy (e.g., MM, WM).

For example, some miRNAs are differentially expressed in circulating exosomes of MGUS patients compared to healthy individuals. Specifically, the following miRNAs are expressed at a higher level in MGUS patients compared to normal subjects: miR-450a, miR-30e, miR-125a, and miR-300; whereas, the following miRNAs are expressed at a lower level in MGUS patients compared to normal subjects: miR-185, miR-150, and miR-98.

Some miRNAs are differentially expressed in circulating exosomes of SMM patients compared to healthy individuals. Specifically, the following miRNAs are expressed at a higher level in SMM patients compared to normal subjects: miR-30e, miR-30d, miR-144, and miR-451a; whereas, the following miRNAs are expressed at a lower level in SMM patients compared to normal subjects: miR-374b, miR-28, miR-92a.

In addition, certain miRNAs are differentially expressed in circulating exosomes of SMM patients compared to MGUS patients. Specifically, the miR-107 is expressed at a higher level in SMM patients compared MGUS subjects, whereas, the following miRNAs are expressed at a lower level in SMM patients compared to MGUS subjects: miR-28, miR-92a, miR-32, miR-548a, miR-939, miR-99a, miR-345, miR-125a, miR-587, and miR-323b.

In addition, certain miRNAs are differentially expressed in circulating exosomes of MM patients compared to normal subjects. Specifically, the following miRNAs are expressed at a higher level in MM patients compared to normal subjects: miR-105-5p, miR-1909-3p, miR-378h, miR-520h, miR-613, miR-107, miR-190a, miR-380-3p, miR-525-3p, miR-614, miR-1179, miR-1911-5p, miR-381, miR-525-5p, miR-621, miR-1180, miR-193a-3p, miR-382-5p, miR-545-3p, miR-626, miR-1183, miR-193b-3p, miR-3934, miR-548a-3p, miR-627, miR-1185-5p, miR-194-5p, miR-409-3p, miR-548ad, miR-630, miR-1193, miR-195-5p, miR-411-5p, miR-548ag, miR-641, miR-1202, miR-1973, miR-422a, miR-548ah-5p, miR-642a-5p, miR-1205, miR-200a-3p, miR-431-5p, miR-548ai, miR-644a, miR-1208, miR-2053, miR-432-5p, miR-548aj-3p, miR-646, miR-1225-5p, miR-208a, miR-433, miR-548al, miR-647, miR-1228-3p, miR-208b, miR-4421, miR-548g-3p, miR-651, miR-1243, miR-2114-5p, miR-4443, miR-548i, miR-656, miR-1244, miR-211-5p, miR-4448, miR-548n, miR-658, miR-1245a, miR-2117, miR-4454, miR-548s, miR-662, miR-1245b-5p, miR-212-3p, miR-4458, miR-548t-5p, miR-663a, miR-1252, miR-215, miR-4461, miR-548u, miR-663b, miR-1253, miR-218-5p, miR-448, miR-548x-3p, miR-670, miR-125b-5p, miR-23c, miR-4488, miR-548z, miR-675-5p, miR-1264, miR-2682-5p, miR-449a, miR-549, miR-744-5p, miR-1265, miR-300, miR-449b-5p, miR-550a-5p, miR-759, miR-1268a, miR-301b, miR-450b-5p, miR-551a, miR-760, miR-1269a, miR-302a-3p, miR-451a, miR-553, miR-761, miR-1273d, miR-302b-3p, miR-4521, miR-556-5p, miR-764, miR-1275, miR-302f, miR-4532, miR-558, miR-766-3p, miR-1277-3p, miR-30e-5p, miR-4647, miR-564, miR-769-3p, miR-1279, miR-3131, miR-4741, miR-566, miR-769-5p, miR-1281, miR-31-5p, miR-4792, miR-567, miR-770-5p, miR-1286, miR-3164, miR-483-3p, miR-569, miR-874, miR-1290, miR-3168, miR-484, miR-570-3p, miR-876-3p, miR-1294, miR-3180, miR-487a, miR-572, miR-885-3p, miR-1295a, miR-3180-3p, miR-490-5p, miR-573, miR-890, miR-1297, miR-3184-5p, miR-491-3p, miR-574-3p, miR-891a, miR-130b-3p, miR-3185, miR-494, miR-575, miR-892a, miR-1321, miR-3196, miR-495, miR-577, miR-922, miR-1323, miR-3200-3p, miR-498, miR-578, miR-924, miR-133b, miR-330-3p, miR-499a-5p, miR-579, miR-935, miR-135a-5p, miR-330-5p, miR-499b-5p, miR-581, miR-938, miR-139-3p, miR-331-5p, miR-510, miR-585, miR-939, miR-141-3p, miR-3614-5p, miR-511, miR-586, miR-941, miR-143-3p, miR-363-3p, miR-514a-3p, miR-588, miR-95, miR-144-3p, miR-3690, miR-514b-5p, miR-590-3p, miR-99b-5p, miR-1470, miR-372, miR-517c-3p, miR-596, miR-375, miR-518b, miR-598, miR-151b, miR-376b, miR-519b-3p, miR-603miR-152, miR-376c, miR-519b-5p, miR-604, miR-1539, miR-378f, miR-520b, miR-605; whereas, the following miRNAs are expressed at a lower level in MM patients compared to normal subjects: let-7a-5p, let-7b-5p, let-7f-5p, let-7g-5p, let-7i-5p, miR-106a-5p, miR-17-5p, miR-106b-5p, miR-1246, miR-126-3p, miR-1285-3p, miR-130a-3p, miR-142-3p, miR-148b-3p, miR-150-5p, miR-15a-5p, miR-15b-5p, miR-181a-5p, miR-185-5p, miR-188-5p, miR-191-5p, miR-199a-3p, miR-199b-3p, miR-199a-5p, miR-19b-3p, miR-20a-5p, miR-20b-5p, miR-21-5p, miR-221-3p, miR-223-3p, miR-23a-3p, miR-24-3p, miR-26a-5p, miR-27b-3p, miR-297, miR-29b-3p, miR-30b-5p, miR-340-5p, miR-361-3p, miR-371a-3p, miR-374a-5p, miR-374b-5p, miR-548c-5p, miR-548p, miR-888-5p, miR-92a-3p, miR-93-5p.

Furthermore, some miRNAs are differentially expressed in plasma of MM patients compared to healthy individuals. Specifically, miR-720 is expressed at a higher level in plasma of MM patients compared to normal subjects; whereas, the following miRNAs are expressed at a lower level in plasma of MM patients compared to normal subjects: miR-15a, miR-19b, miR-21, miR-let-7b, and miR-let-7c.

The sequences (and annotations) for all of the above-recited miRNAs can be readily accessed from miRBase: the microRNA database (www.mirbase.org). Furthermore, the ordinary artisan can readily make anti-miRs (e.g., tiny LNAs) or pre-miRs of any of the above-recited miRs.

The above-noted differences in miRNA expression levels in circulating exosomes and peripheral blood are useful for diagnosis, for prognosis, and for developing specific treatment strategies for personalized therapy for patients with these diseases. Accordingly, it is useful to measure the expression levels of one or more of these miRNAs and compare it to a control level (either a previously determined expression level of a particular miRNA in a normal subject, or from a sample obtained from a healthy subject (i.e., someone without the relevant disease)).

Determining Levels of miRNA

The amount or level of expression of an miRNA or pre-miR can be measured by any method known in the art. Such methods include, without limitation, nCounter miRNA expression assay, Taqman miRNA profiling, quantitative or semi-quantitative RT-PCR methodologies employing appropriate miR-specific oligonucleotide primers, and hybridization assays using detectably labeled miR-specific DNA or RNA probes. Additional methods for quantitating miR in cell lysates include RNA protection assays and small Northern blots. Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes.

For example, the amount or level of an miRNA or a pre-miR thereof may be determined by using a probe oligonucleotide that specifically detects the miRNA or precursor molecule to be analyzed or an amplification product of said miRNA or said precursor. The determination of the amount of a miRNA or of a precursor molecule thereof, by specific probe oligonucleotides involves hybridizing a miRNA (or a precursor molecule thereof) or an amplification product thereof with a probe oligonucleotide that specifically binds to the transcript or the amplification product thereof. The probe oligonucleotide is a single-stranded nucleic acid molecule that is specific for said miRNA or a precursor molecule thereof or an amplification product thereof, and, preferably, comprises a stretch of nucleotides that specifically hybridizes with the target and, thus, is complementary to the target polynucleotide. The probe can be 85%, 90%, 95%, 96%, 97%, 98%, 99% or 100% identical to a sequence region comprised by the target polynucleotide. If the target molecule is an miRNA the probe oligonucleotide can be 85%, 90%, 95%, 96%, 97%, 98%, 99% or 100% identical to said miRNA. The degree of identity between two or more nucleic acid sequences is, preferably, determined by the algorithms of Needleman and Wunsch or Smith and Waterman. To carry out the sequence alignments, the program PileUp (*J. Mol. Evolution*, 25, 351-360 (1987), Higgins, CABIOS, 5: 151-153 (1989)) or the programs Gap and BestFit (Needleman, *J. Mol. Biol.*, 48; 443-453 (1970) and Smith, *Adv. Appl. Math.*, 2; 482-489 (1981)), which are part of the GCG software packet (Genetics Computer Group, 575 Science Drive, Madison, Wis., USA 53711, vers. 1991), can be used. The sequence identity values recited above in percent (%) can be determined using the program GAP over the entire sequence region with the following settings: Gap Weight: 50, Length Weight: 3, Average Match: 10.000 and Average Mismatch: 0.000. The probe oligonucleotide can be labelled or modified (e.g., linked to an enzyme) which allows a determination of the amount of a miRNA or precursor molecule thereof (or of an amplification product thereof). Labelling can be done by various techniques well known in the art.

The level or amount of an miRNA (or of the precursor molecule thereof) can be determined by amplifying an miRNA molecule (or of the precursor molecule thereof) in a sample and determining the amount of the generated amplification products. To determine the amount of an amplification product of an miRNA or precursor thereof in a sample, the miRNA can be amplified as described by Mitchell et al. (*Proc. Natl. Acad. Sci. USA*, 105(30): 10513-10518 (2008)): the miRNAs or pre-miRs can be ligated at the 3' and the 5' end to single-stranded oligonucleotides that contain universal sequences for reverse transcription and for PCR and reverse transcription of the ligation product is carried out. After reverse transcription, the resulting products can be amplified by PCR. By determining the amounts of said amplification products, the amount of the miRNA molecules (or of the precursor molecules thereof) can be assessed. The amounts of the amplifications products can be determined by using probe oligonucleotides as described above. In one embodiment, the PCR is a real-time PCR (RT-PCR) and the amount of a miRNA is determined by quantitative real-time PCR (qRT-PCR). When RT-PCR is carried out, a signal emitted from the PCR assay is monitored during the PCR reaction as an indicator of the amount of amplification product during each PCR amplification cycle, (as opposed to conventional PCR methods, in which is the amplification product is detected at the endpoint of the PCR reaction). Real-time PCR is generally based on the detection and quantification of a fluorescent reporter. The signal increases in proportion to the amount of PCR product in a reaction. When carrying out RT-PCR, the amount of an miRNA or a precursor molecule thereof may be determined by comparing the results to a standard curve produced by real-time PCR of serial dilutions (e.g., undiluted, 1:4, 1:16, 1:64, 1:128) of a pre-determined amount of said marker. Moreover, to accurately determine the amount, the measured amount may be divided by the amount of normalization RNA (or DNA) which allows normalizing for possible variation of the amount of RNA between different samples. A normalization RNA can be an RNA (or DNA) which is added to the sample (spike-in).

Determining the Likelihood of a Subject Having a Hematological Malignancy

The disclosure also features methods of determining the likelihood of a subject having or developing a hematological malignancy. The subject can be one who is suspected of having, or predisposed to developing, a hematological malignancy. Non-limiting examples of hematological malignancies are MM, WM, CLL, and SLL.

In such methods, a biological sample is obtained from the subject and the level of certain miRNA(s) are assessed and compared with a historical control level (i.e., a reference level for the tested miRNA(s) based on sample(s) previously obtained from subjects known to not have the hematological malignancy under study) or the level of the miRNA(s) in a subject who does not present with and/or who has no known predisposition for developing the hematological malignancy. The biological sample is preferably collected in tubes with EDTA. The biological sample can be e.g., a body fluid such as blood or plasma, or a sample from a suspected tumor of the subject. Plasma is the straw-colored/pale-yellow liquid component of blood and is prepared, e.g., by spinning a tube of fresh blood containing an anticoagulant in a centrifuge until the blood cells fall to the bottom of the tube and separating the supernatant from the precipitated blood cells. The miRNAs may need to be isolated from circulating exosomes that are found in the body fluid of the subject. The miRNA(s) whose expression levels are measured comprise at least one, at least two, at least three, at least four, at least five, at least six, at least seven, at least eight, at least nine, at least ten, at least eleven, at least twelve, or one, two, three, four, five, six, seven, eight, nine, ten, eleven, or twelve, of the following miRNAs: miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c.

An increased expression level of miR-155 compared to a historical control level or a control sample from a subject who does not present with and/or who has no known predisposition for developing WM or CLL is indicative that the subject is likely to develop or has WM or CLL. If the subject has the same or similar levels (±5%) of miR-155 compared to the control sample, the subject does not have or is not likely to develop WM or CLL.

An increased expression level compared to a historical control level or a control sample from a subject who does not present with and/or who has no known predisposition for developing a monoclonal gammopathy of at least one, at least two, at least three, at least four, at least five, at least six, at least seven, at least eight, at least nine, at least ten, or one, two, three, four, five, six, seven, eight, nine, ten, or eleven of the following miRNAs: miR-450a, miR-30e, miR-125a, miR-300, miR-30d, miR-144, miR-451a, miR-107, miR-125b, miR-143, and miR-720, is indicative that the subject is likely to develop or has a monoclonal gammopathy such as MGUS, SMM, or MM. If the subject has the same or similar levels (±5%) of the miRNA(s) being compared to the control sample, the subject does not have or is not likely to develop a monoclonal gammopathy such as MGUS, SMM, or MM.

A decreased expression level compared to a historical control level or a control sample from a subject who does not present with and/or who has no known predisposition for developing the hematological malignancy of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or one, two, three, four, five, six, seven, eight, nine, ten, eleven, twelve, thirteen, fourteen, fifteen, sixteen, seventeen, eighteen, nineteen, or twenty of the following miRNAs: miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c, is indicative that the subject is likely to develop or has a monoclonal gammopathy such as MGUS, SMM, or MM. If the subject has the same or similar levels (±5%) of the miRNA(s) being compared to the control sample, the subject does not have or is not likely to develop a monoclonal gammopathy such as MGUS, SMM, or MM.

When there are three or more miRNAs to be evaluated, the miRNAs of interest, or portions/fragments thereof may be attached or linked to a substrate (e.g., a chip, bead, plate) and the biological sample can be used to contact the substrate to determine the levels of the miRNAs of interest in the biological sample.

Identifying the Stage of the Hematological Malignancy

The disclosure also features methods of identifying the stage of a hematological malignancy in a subject. The subject can be asymptomatic, suspected of having, or diagnosed with a particular stage of, a hematological malignancy. If the subject has already been diagnosed as having a hematological malignancy, the subject can be undergoing treatment for the malignancy.

In these methods, a biological sample is obtained from the subject and used to measure the levels of certain miRNAs in that sample. The biological sample can be, e.g., a body fluid such as blood or plasma, or a sample from a tumor from the subject. The miRNAs may need to be isolated from circulating exosomes that are found in the body fluid of the subject.

The levels of the miRNA in the biological sample from the subject are compared to a historical control level (in this context, a reference level for the tested miRNA(s) based on sample(s) previously obtained from subject(s) at known stages of the hematological malignancy under study) or a control sample from a subject who is at a known stage of the hematological malignancy under study.

An increased level compared to a control of at least one, at least two, at least three, or one, two, three, or four of: miR-450a, miR-30e, miR-125a, and miR-300, and/or a decreased level compared to the control subject of at least one, at least two, or one, two, or three of miR-185, miR-150, and miR-98 is indicative that the subject is in the MGUS stage of MM. In certain embodiments, the biological sample used in this analysis comprises circulating exosomes.

An increased level compared to a control of at least one, at least two, at least three, or one, two, three, or four of: miR-30d, miR-30e, miR-144, and miR-451, and/or a decreased level compared to the control subject of at least one, at least two, or one, two, or three of miR-374b, miR-28, and miR-92a is indicative that the subject is in the SMM stage of MM. In certain embodiments, the biological sample used in this analysis comprises circulating exosomes.

An increased level compared to the control subject of miR-107, and/or a decreased level compared to a control of at least one, at least two, at least three, at least four, at least five, at least six, at least seven, at least eight, at least nine, or one, two, three, four, five, six, seven, eight, nine, or ten of: miR-92a, miR-28, miR-32, miR-548a, miR-939, miR-99a, miR-345, miR-125a, miR-587, and miR-323b is indicative that the subject has progressed from the MGUS stage to the SMM stage of MM. In certain embodiments, the biological sample used in this analysis comprises circulating exosomes.

An increased level compared to a control of at least one, at least two, or one, two, or three of miR-125b, miR-143, or miR-720, and/or a decreased level compared to a control of least one, at least two, at least three, at least four, at least five, at least six, at least seven, or one, two, three, four, five, six, seven, or eight of miR-let-7g, miR-223, miR-150, miR-15a, miR-19b, miR-21, miR-let-7b, or miR-let-7c is indicative that the subject has progressed to active or symptomatic MM. In certain embodiments, the biological sample used in this analysis is plasma.

Measuring the levels of the miRNAs listed above is also useful in determining whether a particular treatment is working for the subject. The levels of miRNAs may be measured at any point where a health care practitioner expects the treatment the subject has been receiving to have begun to be effective in controlling the malignancy (e.g., 1 week, 2 weeks, 3 weeks, 1 month, two months, three months, four months, five months, six months, between six months and 1 year, at 1 year). The expression level of the miRNAs that are found to be elevated or decreased in the MGUS, SMM, or symptomatic stage of MM are measured in the subject's biological sample obtained before and after treatment. If these miRNA levels are similar to the miRNA from an advanced stage of the malignancy or if the miRNA levels remain the same as the stage of the disease when the subject began treatment, the treatment is determined to have been ineffective and a new treatment is considered.

For example, consider a patient at the MGUS stage of MM who is receiving treatment for the malignancy. A biological sample is obtained before and after treatment from the patient. miRNA levels of one, two, three, four, five, six, seven, eight, nine, or ten of the miRNAS found elevated or decreased at the different stages of the malignancy are measured in both the pre- and post-treatment samples. If after treatment, the patient shows an miRNA signature that resembles the SMM or active MM stage of the disease, or if the miRNA signature remains unaltered (i.e., the MGUS signature) compared to pre-treatment, the treatment regimen that the patient was on is deemed ineffective and a new treatment is administered to the subject. If after treatment, the patient shows an miRNA signature that resembles a subject who does not have the hematological malignancy or if the miRNAs that are found increased in MGUS are lower than before treatment and/or the miRNAs that are found decreased in MGUS are higher than before treatment, the patient is continued on the treatment regimen that the patient was receiving.

Compositions and Methods for Treatment of Hematological Malignancies

The invention also features methods of treatment of hematological malignancies. In certain embodiments, the methods of treatment involve administering antisense oligonucleotides (anti-miRs) to downregulate expression of miRs that are expressed at higher levels than in a control (e.g., a subject who does not have the disease or a historical reference level based on sample(s) previously obtained from subjects that do not have the disease at issue), and/or administering primary transcripts of miRNAs (pri-miRNAs) or pre-miRNAs to upregulate expression of miRs that are expressed at lower levels than in a control. The methods can optionally be performed after one or more of the above-described diagnostic and/or staging methods.

Anti-miR is an anti-microRNA, which is a short, single-stranded nucleic acid sequence that competitively bind to target its miRNA; ultimately inhibiting its function. Anti-miRs sequester the mature miRNA in competition with cellular target mRNAs leading to functional inhibition of the miRNA and depression of the direct targets. The anti-miRs include molecules having 0, 1, 2, or 3 mismatches (lack of base pairing) with the underlying miR sequence. One of ordinary skill can readily prepare an anti-miR based on the miRNA sequence.

Pri-miRNAs are processed in the nucleus of the targeted cells to approximately 70 nt hairpin-structures, known as pre-miRNAs. Pre-miRNAs are exported to the cytoplasm and processed further to approximately 22 nt double-stranded miRNA duplexes. The miRNA duplexes are loaded into an Argonaute protein in the miRNA-induced silencing complex (miRISC) and rapidly unwound. During this process the mature miRNA is retained in the miRISC, whereas the complementary strand, known as the miRNA star (miR*), is released.

A subject suspected of having, at risk of developing, or presenting with a hematological malignancy can be administered anti-miRs of at least one, at least two, at least three, at least four, at least five, at least six, at least seven, at least eight, at least nine, at least ten, or one, two, three, four, five, six, seven, eight, nine, ten, or eleven of the following miRNAs: miR-450a, miR-30e, miR-125a, miR-300, miR-30d, miR-144, miR-451a, miR-107, miR-125b, miR-143, and miR-720 alone or in combination with pri-miRs or pre-miRs of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or one, two, three, four, five, six, seven, eight, nine, ten, eleven, twelve, thirteen, fourteen, fifteen, sixteen, seventeen, eighteen, nineteen, or twenty of the following miRNAs: miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-150, miR-15a, miR-19b, miR-21, miR-let-7b, and miR-let-7c. It is noted that the pri-miRs or pre-miRs referenced above may also be administered without the anti-miRs.

A subject who is suspected of being in, or diagnosed to be in, the MGUS stage of MM can be administered anti-miRs of at least one, at least two, at least three, or one, two, three, or four of the following miRNAs: miR-450a, miR-30e, miR-125a, and miR-300, alone or in combination with pri-miRs or pre-miRs of at least one, at least two, one, two, or three of the following miRNAs: miR-185, miR-150, and miR-98. The pri-miRs or pre-miRs referenced above may also be administered without the anti-miRs.

A subject who is suspected of being in, or diagnosed to be in, the SMM stage of MM can be administered anti-miRs of the miRNA, miR-107 (either alone or in combination with anti-miRs to one, two three, or four of the following miRs: miR-30d, miR-30e, miR-144, and) miR-451a alone or in combination with pri-miRs or pre-miRs of at least one, at least two, at least three, at least four, at least five, at least six, at least seven, at least eight, at least nine, or one, two, three, four, five, six, seven, eight, nine, or ten of the following miRs: miR-28, miR-92a, miR-32, miR-548a, miR-939, miR-99a, miR-345, miR-125a, miR-587, and miR-323b. The pri-miRs or pre-miRs referenced above may also be administered without the anti-miRs.

A subject who is suspected of being in, or diagnosed to be in, the active MM stage of MM can be administered anti-miRs of at least one, at least two, or one, two, or three of the following miRs: miR-125b, miR-143, and miR-720, alone or in combination with pri-miRs or pre-miRs of at least one, at least two, at least three, at least four, at least five, at least six, at least seven, or one, two, three, four, five, six, seven, or eight of the following miRs: miR-let-7g, miR-223, miR-150, miR-15a, miR-19b, miR-21, miR-let-7b, and miR-let-7c. The pri-miRs or pre-miRs referenced above may also be administered without the anti-miRs.

The methods of treating a subject with any stage of myeloma described above can also include administering agents that reduce the levels of one or more, two or more, three or more or all of the following proteins: IL-6, CCL2/MCP-1, junction plakoglobin, and fibronectin. Such agents include antibodies or biologically active fragments thereof or any other inhibitor that blocks or reduces the activity of these proteins. In one embodiment, the subject is administered an anti-IL-6 antibody. Non-limiting examples of IL-6 antibody include tocilizumab, CNTO 328, ALD518/BMS-945429, CNTO 136, CPSI-2364, CDP6038, VX30, RGX-109, FE301 and FM101. These treatments can also include the use of antisense oligonucleotides, interfering RNA and other anti-sense based agents that target the miRNA that is to be downregulated.

The oligonucleotides (e.g., anti-miRs, pre-miRs) for use in treatment can optionally be modified to optimize for increased binding affinity, improved nuclease resistance, increase serum stability, half-life, and/or permeability into cells when administered in vivo without negatively impacting its properties. This can be achieved using a variety of chemical modifications, including modifications of the sugar, the nucleobase, or the internucleotide linkages. Chemical modifications include, but are not limited to, the 2'-O-Me modification, the 2'-O-methoxyethyl (2'-MOE) modification, the 2'-fluoro (2'-F) modification, and the locked nucleic acid (LNA) modification. The 2'-O-Me, 2'-MOE and the 2'-F chemistries are modified at the 2' position of the sugar moiety, whereas LNA comprises a class of bicyclic RNA analogues in which the furanose ring in the sugar-phosphate backbone is chemically locked in a RNA mimicking N-type (C3'-endo) conformation by the introduction of a 2'-O,4'-C methylene bridge. All of the above modifications confer nuclease resistance and increase the binding affinity of anti-miR oligonucleotides to their cognate miRNAs. LNA possesses the highest affinity towards complementary RNA with an increase in duplex melting temperature (Tm) of +2 to 8° C. per introduced LNA monomer against complementary RNA compared with unmodified duplexes. Nuclease resistance can also be improved by backbone modification of the parent phosphodiester linkages into phosphorothioate (PS) linkages in which a sulfur atom replaces one of the non-bridging oxygen atoms in the phosphate group, or by using morpholino oligomers in which a six-membered morpholine ring replaces the sugar moiety. Morpholinos are uncharged, inherently resistant to degradation by nucleases, and generally exhibit a slight increase in binding affinity to miRNAs. Morpholino oligomers are sequence-specific, non-toxic, and potent inhibitors of both pri-miRNA and mature miRNA activity. In certain embodiments, the anti-miRs used for treatment are LNA/DNA, 2'-F/MOE, or LNA/2'-O-Me mixmers with PS ends. In certain embodiments, the anti-miRs used for treatment are LNA/2'-O-Me mixmers with a complete PS backbone. In certain embodiments, the anti-miRs used for treatment are tiny LNAs. Tiny LNAs are short "seed-targeting" (i.e., targeting the seed region of the miRNAs) LNA oligonucleotides. Tiny LNAs that can inhibit any of the miRNAs disclosed in this application can be readily made by the ordinary artisan.

The anti-miRs or pre-miRs can be chemically synthesized. Methods of synthesizing nucleic acids are well known in the art (e.g., using appropriately protected ribonucleoside phosphoramidites and a conventional DNA/RNA synthesizer). The anti-miRs or pre-miRs can also be produced by recombinant methods. These methods include the use of vectors (viral and non-viral), plasmids, cosmids, and any other vehicle for delivering a nucleic acid to a host cell to produce large quantities of the desired molecule. For example, the microRNAs and anti-miRs described herein can be expressed from recombinant circular or linear plasmids using any suitable promoter. Non-limiting examples of promoters for expressing RNA from a plasmid include the U6 or H1 RNA Pol III promoter sequences or the cytomegalovirus promoters. Selection of other suitable promoters is within the skill in the art. Recombinant vectors can also include inducible or regulatable promoters for expression of the microRNA and/or antimiRs in cancer cells. The expression vectors can also be used in the context of a cell free system so long as the reagents for generating and processing the microRNAs are present.

The microRNAs and anti-miRs described herein can also be expressed from recombinant viral vectors. Non-limiting examples of viral vectors that can be used to express the microRNAs and anti-miRs of the invention include: adenovirus, adeno-associated virus, retroviruses (e.g., lentiviruses, rhabdoviruses, murine leukemia virus), and herpes virus. The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art.

In methods of the invention a cell or other biological matter such as an organism (including human patients) can be provided a miRNA or anti-miR molecule corresponding to a particular miRNA or antagomir by administering to the cell or organism a nucleic acid molecule that functions as the corresponding miRNA or anti-miR once inside the cell. The form of the molecule provided to the cell may not be the form that acts a miRNA or anti-miR once inside the cell. Thus, it is contemplated that in some embodiments, a synthetic or a nonsynthetic miRNA is provided such that it becomes processed into a mature and active miR/anti-miR once it has access to the cell's miRNA processing machinery. In certain embodiments, it is specifically contemplated that the miRNA molecule provided is not a mature miRNA molecule but a nucleic acid molecule that can be processed into the mature miRNA once it is accessible to miRNA processing machinery.

The dosage of the anti-miRs, miRs, or pre-miRs will vary with the nature and location of the hematological malignancy to be targeted. In certain embodiments, the anti-miRs, miRs, or pre-miRs are administered at a dose of from about 1 mg/kg/dose to about 500 mg/kg/dose (e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 100 mg/kg, 150 mg/kg, 175 mg/kg, 200 mg/kg, 225 mg/kg, 250 mg/kg) where kg refers to the weight of the patient. In certain embodiments, the miRs and anti-miRs described herein can be administered to the subject in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1500, 2000, 2500, 3000 μg or mg, or any range between 0.5 μg or mg and 3000 μg or mg. The amount specified may be the amount administered as the average daily, average weekly, or average monthly dose. In other embodiments, the amount specified is any number discussed above but expressed as $mg/m^2$ (with respect to tumor size or patient surface area). A clinician can readily determine the effective amount of an anti-miR(s) or pre-miR(s) or miR to be used—i.e. the amount of these molecules needed to inhibit proliferation of a cancer cell, by taking into account factors, such as the size and weight of the subject; the extent of disease penetration; the age, health and sex of the subject; the route of administration; and whether the administration is regional or systemic. Multiple doses may be administered depending on the disease severity. The anti-miRs, miRs, or pre-miRs can be administered in a pharmaceutically acceptable carrier. Pharmaceutically acceptable carriers are well known in the art.

Methods of administering the molecules described herein as well as treatment regimens may vary and will depend on the tumor type, tumor location, immune condition of the subject, target site, disease progression, and health and age of the subject. The clinician will be best suited to make such decisions based on the known efficacy and toxicity (if any) of the therapeutic formulations. Non-limiting routes of administration include: intravenous, intradermal, subcutaneous, regional, parenteral, intramuscular, intranasal, systemic, and oral administration. Direct injection, intratumoral injection, or injection into tumor vasculature is contemplated for discrete, solid, accessible tumors, or other accessible target areas. Local, regional, or systemic administration also may be appropriate. The miRs or antimiRs described herein can be delivered via syringe or catherization. The compositions of the invention can also be administered in multiple injections to a tumor or a targeted site. Liposomes can also be used to deliver the microRNAs and antimiRs described herein (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes are well known in the art. The liposomes for use in the present methods can comprise a ligand molecule that targets the liposome to cancer cells, e.g., ligands that bind to receptors prevalent in cancer cells, such as monoclonal antibodies that bind to tumor cell antigens. The liposomes can also be modified so as to avoid clearance by the mononuclear macrophage system and reticuloendothelial system. Such modified liposomes have opsonization-inhibition moieties on the surface or incorporated into the liposome structure. In one embodiment, a liposome of the invention can comprise both an opsonization-inhibition moiety and a ligand. Opsonization-inhibiting moieties for use in preparing the liposomes of the invention are typically large hydrophilic polymers that are bound to the liposome membrane. These opsonization-inhibiting hydrophilic polymers form a protective surface layer that significantly decreases the uptake of the liposomes by the MMS and RES. Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include, but are not limited to polyethylene glycol (PEG) or polypropylene glycol (PPG) or derivatives thereof (e.g., methoxy PEG or PPG, and PEG or PPG stearate); synthetic polymers, such as polyacrylamide or poly N-vinyl pyrrolidone; linear, branched, or dendrimeric polyamidoamines; polyacrylic acids; polyalcohols (e.g., polyvinylalcohol and polyxylitol to which carboxylic or amino groups are chemically linked), as well as gangliosides, such as ganglioside GM1. Liposomes modified with opsonization-inhibition moieties remain in the circulation much longer than unmodified liposomes. Liposomes are known to accumulate in tissues fed by porous or "leaky" microvasculature. Thus, tissue characterized by such microvasculature defects, for example, solid tumors, will efficiently accumulate these liposomes. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miRs and anti-miRs described herein (or nucleic acids comprising sequences encoding them) to tumor cells.

This disclosure also features methods of treating hematological malignancies such as WM and CLL. In such methods, subjects are administered a combination of anti-miR-155 alone or in combination with everolimus and/or an anti-CD20 antibody or biologically active fragment thereof and/or a proteasome inhibitor. Examples of anti-CD20 antibodies include, but are not limited to, rituximab, ofatumumab, veltuzumab, ocrelizumab, AME-133v, PRO131921 and GA-101. Also useful in the present methods are substances such TRU-015, which is a small modular immunopharmaceutical (SMIP) derived from key domains of an anti-CD20 antibody. Non-limiting examples of proteasome inhibitors for use in the methods described herein are bortezomib, disulfiram, epigallocatechin-3-gallate, Salinosporamide A, carfilzomib, ONX 0912, CEP-18770, and MLN9708. These treatments can also include the use of antisense oligonucleotides, interfering RNA and other antisense based agents that target miR-155.

The treatments described above for any of the hematological malignancies can also include chemotherapy either before, substantially at the same time as, or after the indicated treatment. Non-limiting examples of chemotherapeutic agents include, but are not limited to, an alkylating agent (e.g. busulfan, chlorambucil, cisplatin, cyclophosphamide (cytoxan), dacarbazine, ifosfamide, mechlorethamine (mustargen), and melphalan), a topoisomerase inhibitor, an antimetabolite (e.g. 5-fluorouracil (5-FU), cytarabine (Ara-C), fludarabine, gemcitabine, and methotrexate), an anthracycline, an antitumor antibiotic (e.g. bleomycin, dactinomycin, daunorubicin, doxorubicin (Adriamycin), and idarubicin), an epipodophyllotoxin, nitrosureas (e.g. carmustine and lomustine), topotecan, irinotecan, doxorubicin, etoposide, mitoxantrone, bleomycin, busultan, mitomycin C, cisplatin, carboplatin, oxaliplatin and docetaxel.

The following examples are intended to illustrate, not limit, the invention.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Materials and Methods for Examples 2 and 3 a) Exosome Isolation by Ultracentrifugation:

Exosomes were purified by differential centrifugation as described previously (Kyle R. A. et al., Leukemia, 23:3-9 (2009)). Briefly, relatively large particulate material (e.g., cells) in human plasma was pelleted by centrifugation at 300g for 10 min. The supernatant was centrifuged at 2,000g for 10 min, the supernatant from the 2,000g centrifugation was centrifuged at 10,000g for 30 min, and exosomes were harvested by centrifugation of the supernatant from the 10,000g centrifugation was at 100,000g for 70 min. The exosome pellet was resuspended in 10 ml of PBS and collected as a pellet by ultracentrifugation at 100,000g for 70 min (Beckman Sw41Ti rotor).

miRNA profiling was performed either with the nCounter miRNA expression assay (Nanostring® Technologies, Seattle Wash.) according to the manufacturer's instructions or by using TaqMan human miRNA profiling.

There was no difference in the quantity or quality of exosomes and miRNA content in exosomes isolated from EDTA or heparin tubes, but there were lower levels of free circulating miRNA detected in tubes with heparin compared to tubes with EDTA.

b) Isolation of Exosomal RNA and miRNA Profiling:

RNA was isolated using RNeasy mini kit (Qiagen, Valencia, Calif.), according to the manufacturer's protocol and as previously described (Valadi et al., Nature Cell Biol., 9:654-659 (2007)). miRNA profiling was assessed by using TaqMan human miRNA profiling. C. elegans miRNA-39 was chosen as an internal spiked control because of a lack of sequence homology to human miRNAs and absence of empiric hybridization to human miRNA probes on miRNA microarrays, as previously described (Kroh E. M. et al., Methods, 50:298-301 (2010)). A Mean miRNA expression value was used for miRNA RT-qPCR data normalization, as described (Mestdagh P. et al., *Genome Biology*, 10:R64, (2009)). Comparison between normal and multiple myeloma bone marrow mesenchymal stromal cells-derived exosomes was performed by using dChip software.

c) Quantitative Reverse Transcription-PCR (qRT-PCR): qRT-PCR for miRNAs of interest (TaqMan microRNA Assays, Applied Biosystems, Foster City, Calif.) was performed on an Applied Biosystems AB7500 Real Time PCR system. All PCR reactions were run in triplicate and miRNA expression, relative to RNU6B or *C. Elegans* miRNA39, was calculated using the $2^{-\Delta\Delta C(T)}$ method (Livak K. J. et al., Methods, 25:402-8, (2001)).

Example 2: miRNA Expression in Circulating Exosomes in Normal, MGUS, Smoldering MM, and Active MM Exosomes were isolated using ultracentrifugation from peripheral blood obtained from healthy individuals (n=4), MGUS patients (n=4), SMM patients (n=4), and symptomatic MM (n=8) patients, and further studied by using electron microscopy and immunogold labeling for the detection of CD63 and CD81. miRNA profiling was performed using nCounter miRNA expression assay (Nanostring® Technologies, Seattle Wash.). Bioinformatic software tools (TargetScan, MIRDB) were used to predict the target genes of identified miRNA and define their function. Circulating exosomes were studied at the ultrastructural level showing positivity for CD81 and CD63 as demonstrated by immunogold labeling and electron microscopy.

Seven miRNAs were found to be differentially expressed in circulating exosomes obtained from MGUS patients as compared to healthy subjects (p<0.05): specifically, higher expression of miR-450a, miR-30e, miR-125a, and miR-300, and lower expression of miR-185, miR-150, and miR-98, were observed in miRNAs isolated from circulating exosomes of MGUS patients compared to circulating exosomes obtained from healthy individuals (FIG. 1). Interestingly, miR-30e and miR-150 are important for modulation of NK cell activity by targeting perforin and c-Myb, respectively.

Seven miRNAs were found to be differentially expressed in circulating exosomes obtained from SMM patients as compared to healthy subjects (p<0.05): specifically, higher expression of miR-30e, miR-30d, miR-144, and miR-451a, and lower expression of miR-374b, miR-28, and miR-92a, were observed in miRNAs isolated from circulating exosomes of SMM patients compared to circulating exosomes obtained from healthy individuals. The miRNAs are useful in following progression from the normal state to the SMM stage of the disease.

In addition, the miRNA expression profiles between MGUS and SMM circulating exosomes were compared. Eleven miRNAs were found to be differentially expressed (p<0.05): specifically, higher expression of miR-107, and lower expression of miR-28, miR-32, miR-548a, miR-939, miR-99a, miR-345, miR-125a, miR-587, miR-323b, and miR-92a were observed in miRNAs of circulating exosomes isolated from SMM patients as compared to MGUS patients (see, FIG. 1). Among the de-regulated miRNAs, miR-99a, miR-345, miR-92a, and miR-28 are tumor suppressors. Moreover, miR-107 is known to decrease hypoxia-inducible factor-1β (HIF-β) and other predicted targets for miR-107 include genes involved in molding the bone marrow microenvironment; miR-125a is correlated with the expression level of matrix metalloproteinase (MMP) 11 and vascular endothelial growth factor A (VEGF-A); and miR-548a regulates the expression of MMP2.

Figure 3:
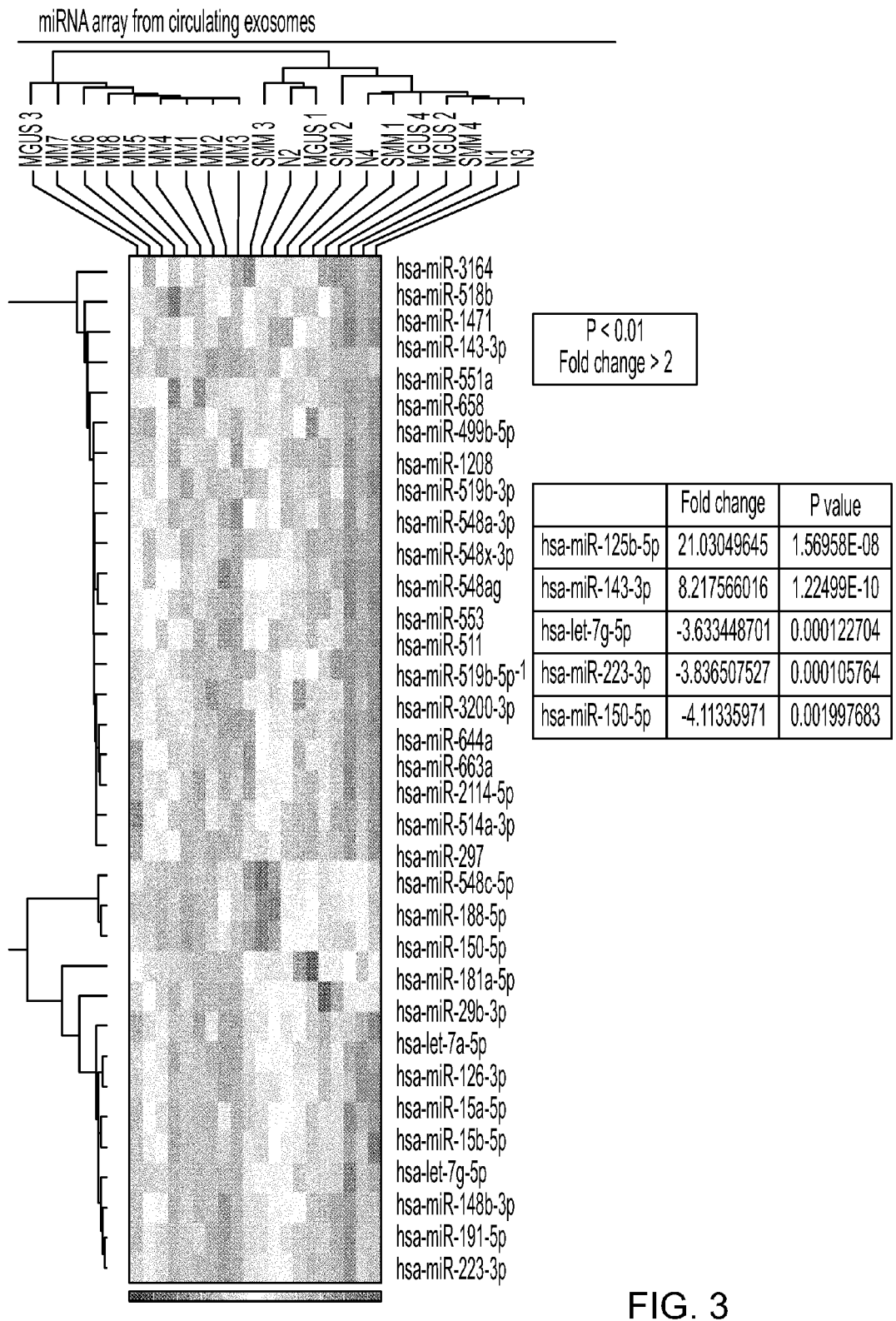
FIG. 3 depicts the results of miRNA profiling from circulating exosomes in normal, MGUS, SMM, and MM patients showing the most significantly changed miRNAs between MM and all the other classes including normal, MGUS and SMM. In the heat map, the intensity of color in each cell correlates with the degree of increase or decrease in expression.
Figure 4:
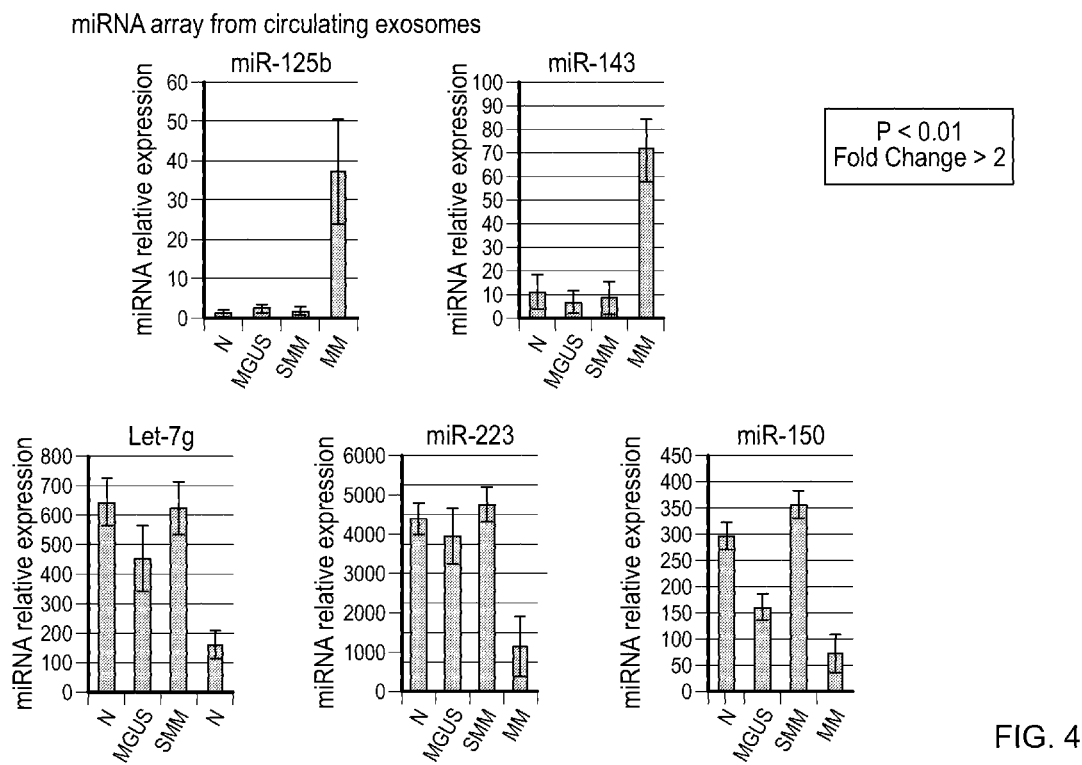
FIG. 4 are bar graphs confirming miRNA expression using qPCR on samples of normal, MGUS, SMM, and MM.

The following miRNAs were found to be upregulated in MM patients over normal, MGUS, and SMM subjects: miR-125b and miR-143; whereas the following miRNAs were found to be downregulated in MM patients compared to normal, MGUS, and SMM subjects: let-7g; miR-223, and miR-150 (see, FIGS. 3 and 4).

These findings indicate that specific miRNAs in circulating exosomes differ between normal and MGUS patients, normal and SMM patients, normal and MM patients, MGUS patients and SMM patients, MGUS patients and MM patients, and SMM and MM patients. These differences could be involved in the differences in the host microenvironment for specific homing of clonal plasma cells to the bone marrow between normal subjects and MGUS, SMM and MM patients, thus providing a better understanding of the epigenetic changes responsible for the transition from the MGUS stage to the SMM stage and the SM stage to the MM stage.

In sum, exosomal miRNAs can be used to follow disease progression from normal to MGUS to smoldering MM to overt symptomatic MM and thus be used to determine the appropriate therapies for a patient.

Example 3: Let-7 MicroRNAs Regulate Cell Proliferation in Multiple Myeloma

This study was performed to investigate the role of Let-7 miRNA family members in MM.

Circulating miRNA profiling was performed in MM patients compared to healthy individuals using TaqMan human miRNA profiling, and validated by qRT-PCR. Exosomes were collected from both normal and MM peripheral blood, using ultracentrifugation and further studied by using electron microscopy and immunogold labeling for the detection of CD63 and CD81. Exosomes were then evaluated for their miRNA content, by qRT-PCR. Gain- and loss-of functions studies were performed on MM cell lines (MM.1S; U266), using Let-7-mimic and Lin28B siRNA, respectively. Scramble probe-transfected cells were used as control. Cell proliferation and cell survival were evaluated by using BrdU assay and MTT assay, respectively. Effects of Let-7 and Lin28B on signaling cascades were evaluated by western blot.

This study identified an MM specific signature (compared to normal patients) characterized by down-regulation of miR-15a, miR-19b, miR-21, let-7b, let-7c, and over-expression of miR-720 (P<0.001) in peripheral blood (whole plasma). Moreover, the same miRNA signature was found in the circulating exosomes, suggesting that circulating miRNAs may be transported by exosomes. The Let-7 family members were significantly decreased in peripheral blood of MM patient compared to healthy individuals, suggesting that the Let-7 family is down-regulated in MM cells. A qRT-PCR was then performed in MM primary cells and it was found that the Let-7 family was significantly downregulated in MM primary cells, especially Let-7b and Let-7c (5 fold change, P<0.05). Over-expression of Let-7b and Let-7c in MM cells (U266; MM1S) by transfection decreased cell proliferation.

These data indicate that miRNA play an important role in the MM biology and thus, provide the basis for the development of new miRNA-based target therapies and biomarkers for this disease.

Example 4. Materials and Methods for Examples 5-9 a) Cells and Reagents:

Primary WM cells were collected from the bone marrow of WM patients using CD19' microbead selection (Miltenyi Biotec, Auburn, Calif.) with more than 90% purity, as confirmed by flow cytometric analysis with monoclonal antibody against human CD19 (BD Biosciences, San Jose, Calif.) 13. Similarly, CD19$^+$ cells were isolated from the bone marrow (BM) and peripheral blood of 3 healthy donors, and used as controls. Approval for these studies was obtained from the Dana-Farber Cancer Institute Institutional Review Board. Informed consent was obtained from all patients and healthy volunteers in accordance with the Declaration of Helsinki protocol. BCWM1, MEC1 and HEK293 cell lines were used in this study. BCWM.1 is a previously described WM cell line derived from CD19$^+$ selected bone marrow lymphoplasmacytic cells isolated from a patient with untreated WM23, MEC1 is a cell line derived from B-chronic lymphocytic leukemia in prolymphocytoid transformation24 and HEK293 is a human embryonic kidney epithelial cell line (ATCC# CRL-1573). The cell lines were cultured as previously described 13. BCWM1, MEC1 and mCherry-Luc+-BCWM1 cells were cultured at 37° C. in RPMI-1640 containing 10% fetal bovine serum (FBS; Sigma Chemical, St Louis, Mo.), 2 mM L-glutamine, 100 U/mL penicillin, and 100 µg/mL streptomycin (Invitrogen, CA). mCherry-Luc+-BCWM1 cells were generated using lentiviral infection and were a gift from Dr. Andrew Kung at Dana-Farber Cancer Institute. Human stromal cells negatively selected by CD19$^+$ microbeads from normal healthy donors or WM patients were cultured at 37° C. in DMEM containing 20% fetal bovine serum, 2 mM L-glutamine, 100 U/mL penicillin, and 100 µg/mL streptomycin. Mouse stromal cells were isolated and cultured as a reference (Raaijmakers M. H. et al., *Nature*, 464(7290):852-857 (2010)). HEK293 cells stably expressing copGFP control plasmid or stably expressing pre-miR-155 were generated using PMIRH155PA-1 or pCDH-CMV-MCS-EF1-copGFP cDNA Cloning and Expression Vector (System Biosciences) by lentiviral infection and sorting by using the GFP marker. HEK293 and mice stromal cells were cultured at 37° C. in DMEM containing 20% fetal bovine serum, 2 mM L-glutamine, 100 U/mL penicillin, and 100 µg/mL streptomycin.

b) DNA Synthesis and Cytotoxicity Assay:

Cell proliferation rate and cytotoxicity of BCWM1, MEC1 or stromal cells were measured by DNA synthesis using [H]$^3$ thymidine uptake assay (Perkin Elmer, Boston, Mass.), and by 3-(4,5-dimethylthiazol-2-yl)-2,5-diphenyltetrazolium bromide (MTT; Chemicon International, Temecula, Calif.) dye absorbance, respectively, as previously described (Roccaro A. M. et al., *Blood*, 113(18):4391-4402, 26 (2009); Leleu X., et al., *Blood*, 110(13):4417-4426 (2007)).

c) Gene Expression Profiling (GEP):

Total RNA from BCWM1 cells treated with antimiR-155 or LNA scramble control oligonucleotide, respectively, for 48 hours, were isolated using RNeasy kit (Qiagen) as described by the manufacturer, and hybridized on an Affymetrix U133A 2.0 array chip (Affymetrix, Santa Clara, Calif.). GEP data were analyzed using dChip software (biosunl.harvard.edu/complab/dchip/). Candidate target mRNAs for miR-155 were identified by using the algorithms TargetScan (genes.mit.edu/targetscan/), PicTar (pictar.bio.nyu.edu/) and RNAhybrid (bibiserv.techfak.uni-bielefeld.de/rnahybrid/).

d) Quantitative Reverse Transcription Polymerase Chain Reaction (qRT-PCR):

Total RNA of cells was isolated with the RNeasy kit (Qiagen). cDNA was synthesized using the SuperScript cDNA synthesis kit (Invitrogen) and qRT-PCR reactions were performed using SYBR master mix (SA Bioscience) with designated primers relative to 18S expression by StepOnePlus™ Real-Time PCR System (Applied Biosystem) in triplicates. TaqMan® microRNA Assays kits (Applied Biosystem) were used for quantifying hsa-miR-155 levels relative to RNU6B expression.

e) Luciferase Assays:

The oligonucleotides comprising the wild-type or mutated miR-155 target sequences were synthesized by Integrated DNA Technologies, and annealed to be cloned into pMiR-GLO vector (Promega) for luciferase reporter assays. The miR-155 target sequences within the 3' UTRs of each target mRNA were predicted by TargetScan, and the sequences are shown below with the wild-type and mutated miR-155 seed match sites underlined. Each construct was confirmed by sequencing at the Molecular Biology Core Facility of Dana-Farber Cancer Institute.

```
                                              (SEQ ID NO: 1)
MAFB wild-type: 5' AAAUACAAAAAAUCUGCAUUAAA 3'
(Position 628-634)

(SEQ ID NO: 2)
MAFB mutated:   5' AAAUACAAAAAAUCUCGUAAUAA 3'

(SEQ ID NO: 3)
SH3PXD2A wild-type: 5' GGAAAUUUCACACUGGCAUUAAC 3'
(Position 5426-5432)

(SEQ ID NO: 4)
SH3PXD2A mutated:   5' GGAAAUUAGUGACUGCGUAAUAC 3'

(SEQ ID NO: 5)
SHANK2-1 wild-type: 5' GUUAUUGAACAAGCAAGCAUUAU 3'
(Position 3148-3154)

(SEQ ID NO: 6)
SHANK2-1 mutated:   5' GUUAUUGAACAAGCAUCGUAAUU 3'

(SEQ ID NO: 7)
SHANK2-2 wild-type: 5' AUCAUGAGAUGAAUGAGCAUUAC 3'
(Position 2190-2196)

(SEQ ID NO: 8)
SHANK2-2 mutated:   5' AUCAUGAGAUGAAUGUCGUAAUC 3'
```

HEK293 cells were seeded into 96-well plates and transfected with the constructs harboring wild-type or mutated 3'UTR target sequences or empty vector as control. Luciferase activity was measured using the Dual-Glo Luciferase Assay System (Promega). Renilla luciferase activity was normalized to corresponding firefly luciferase activity and shown as a relative percentage of the control. Experiments were done in triplicate and repeated three times.

f) In Vivo Studies:

Approval of animal studies was obtained by the Dana-Farber Cancer Institute Institutional Animal Care and Use Committees. 6- to 8-week old, female severely immunodeficient (SCID) mice or Balb/c mice were obtained from Charles River Laboratories (Wilmington, Mass.). Anesthesia was performed by intraperitoneal injections of ketamine (Bedford Laboratories, Bedford, Ohio) (80 mg/kg body weight)/xylazine (Lloyd Laboratories, Shenandoah, Iowa) (12 mg/kg body weight).

Balb/c mice were treated with a single intravenous tail vein injection of FAM-labeled antimiR-155 (synthesized with a complete PS backbone and fully LNA-modified (Obad S., *Nat. Genet.*, 43(4):371-378 (2011)) or with saline as control. Live in vivo confocal imaging was used to detect the distribution of the FAM-labeled antimiR in the mouse bone marrow 1 or 2 weeks after injection. Cells from mouse tissues were analyzed by immunofluorescence and flow cytometry.

Immediately after tail vein injection of mCherry-Luc+-BCWM1 cells (3×106/mouse) in SCID mice, the mice (6 mice/group) were treated with a single intravenous tail vein injection of 25 mg/kg with either antimiR-155 or LNA scramble control, followed by weekly maintenance doses of 5 mg/kg antimiR-155 or LNA scramble control until the mice were sacrificed. Mice were injected with 75 mg/kg luciferin (Caliper Life Sciences, Hopkinton, Mass.), followed by whole-body real-time bioluminescence imaging (Xenogen IVIS imaging system, Caliper Life Sciences, Hopkinton, Mass.) performed at Day 0, Day 14, and Day 19. Mice were sacrificed by inhalation of CO2. RNA was extracted from CD19+ cells isolated from one mouse femur by using CD19+ microbead selection. The other femur, liver, and spleen were fixed in formaldehyde. Tissue sections were stained as previously described (Roccaro A. M. et al., *Blood*, 113(18):4391-4402 (2009)), using antibodies against MAFB (Abcam) or CEBPβ (Abcam).

g) Statistical Analysis:

Data were analyzed using unpaired student's t-tests when comparing two conditions, or a one-way ANOVA with Bonferroni or Newman-Keuls correction for multiple comparisons. Probability-values of less than 0.05 were considered significant and tests were performed two-sided. Data is presented as mean and error bars depict the standard deviation (SD).

Example 5. Inhibition of miR-155 Decreases WM and CLL Proliferation in Vitro

The level of miR-155 was first examined in primary WM and CLL primary cells, as well as in IgM secreting low-grade lymphoma cell lines (BCWM1; MEC1) by quantitative RT-PCR (qRT-PCR). The data showed that miR-155 was significantly higher in these samples compared to normal donor CD19+ cells isolated from healthy subjects (data not shown), thus suggesting that miR-155 may represent a viable therapeutic target in these diseases. In order to inhibit miR-155 function in malignant cells, a fully LNA-modified 8-mer seed-targeting antimiR-155 (3'ATTACGAT 5' (SEQ ID NO:9)) was used (Obad S. et al., *Nat. Genet.*, 43(4):371-378 (2011)).

```
                                              (SEQ ID NO: 10)
       "seed"
5' U UAAUGCUAAUCGUGAUAGGGGU 3' - mouse mirR-155

(SEQ ID NO: 11)
5' U UAAUGCUAAUCGUGAUAGGGGU 3' - human mirR-155

(SEQ ID NO: 9)
3' ATTACGAT 5' - Tiny antimiR-155
```

To assess the uptake of antimiR-155 into BCWM1 or MEC1 cells, a 5' FAM-labeled antimiR-155 was used and the antimiR was added directly to the cell suspension without any transfection reagent. The uptake of FAM-labeled antimiR-155 into BCWM1 cells was higher than 90% as judged by flow cytometry (data not shown), which indicates efficient delivery of the 8-mer antimiR into tumor cells. To further examine the functional effect of antimiR-155 on BCWM1 or MEC1, cell survival and cell proliferation was measured by MTT and $[H]^3$ thymidine uptake assays, respectively. Treatment of BCWM1 or MEC1 cells with 20 μM antimiR-155 or scramble control showed significant reduction in cell proliferation 48 hours after treatment (FIG. 5A), with no change in cell cytotoxicity (data not shown). Thus, miR-155 inhibition regulates cell proliferation, but not cell apoptosis.

Example 6. Identification of Novel miR-155 Targets in B Cell Lymphoma Cells

Figure 5:
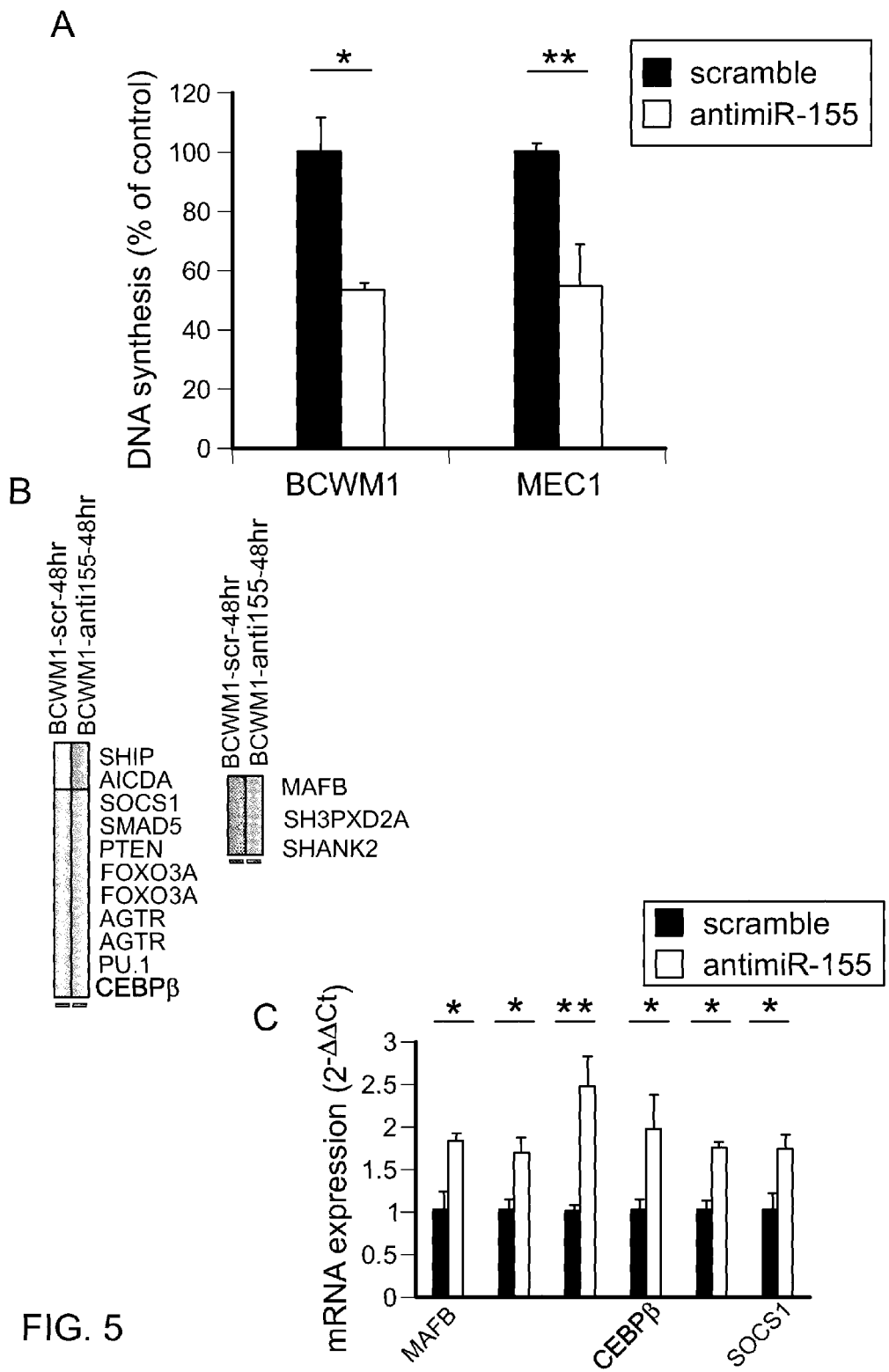
FIG. 5A is a bar graph showing reduction in cellular proliferation (assessed by DNA synthesis) after treatment with anti-miR-155. Mean±SD. *, P<0.05; **, P<0.01.
FIG. 5B shows that several validated miR-155 target mRNAs (left panel) as well as three new targets (MAFB, SHANK2 and SH3PXD2A) (right panel) were upregulated after treatment with antimiR-155 compared to cells treated with scramble control.
FIG. 5C is a bar graph showing qRT-PCR analysis of selected miR-155 targets in BCWM1 cells treated with antimiR-155 or scramble control for 48 hours. Experiments were performed in triplicate and repeated three times. Mean±SD. *, P<0.05; **, P<0.01.
FIG. 5D is a bar graph showing that relative luciferase activity was decreased in miR-155-over-expressing 293 cells transfected with plasmids harboring miR-155 target sequences compared with plasmids harboring mutated target sequences. Experiments were performed in triplicate and repeated three times. Mean±SD. *, P<0.05; **, P<0.01.
FIG. 5E is a bar graph showing mRNA levels of miR-155 target genes detected by qRT-PCR from normal donor blood CD19$^+$ cells, BCWM1 and MEC1 cells, primary WM CD19$^+$ cells, and primary CLL cells. Experiments were performed in triplicate, and repeated three times. Mean±SD.
FIG. 5F is a bar graph showing mRNA levels of miR-155 target genes detected by qRT-PCR from primary WM CD19$^+$ cells treated with 20 μM antimiR-155 or scramble control for 48 hours. Experiments were performed in triplicate, and repeated three times. Mean±SD.
FIG. 5G is a bar graph showing mRNA levels of miR-155 target genes detected by qRT-PCR from primary CLL cells treated with 20 μM antimiR-155 or scramble control for 48 hours. Experiments were performed in triplicate, and repeated three times. Mean±SD.
Figure 5:
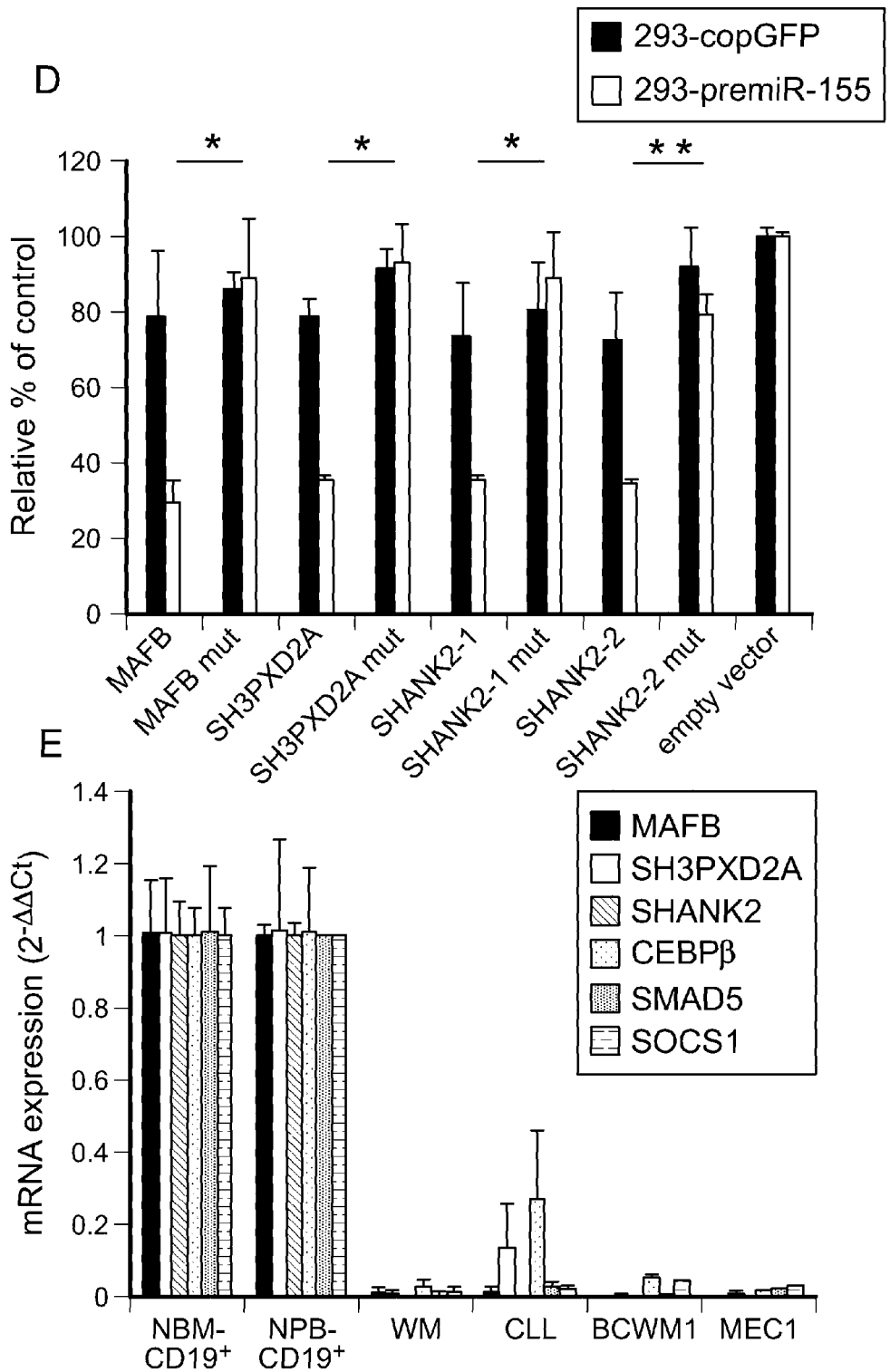
Figure 5:
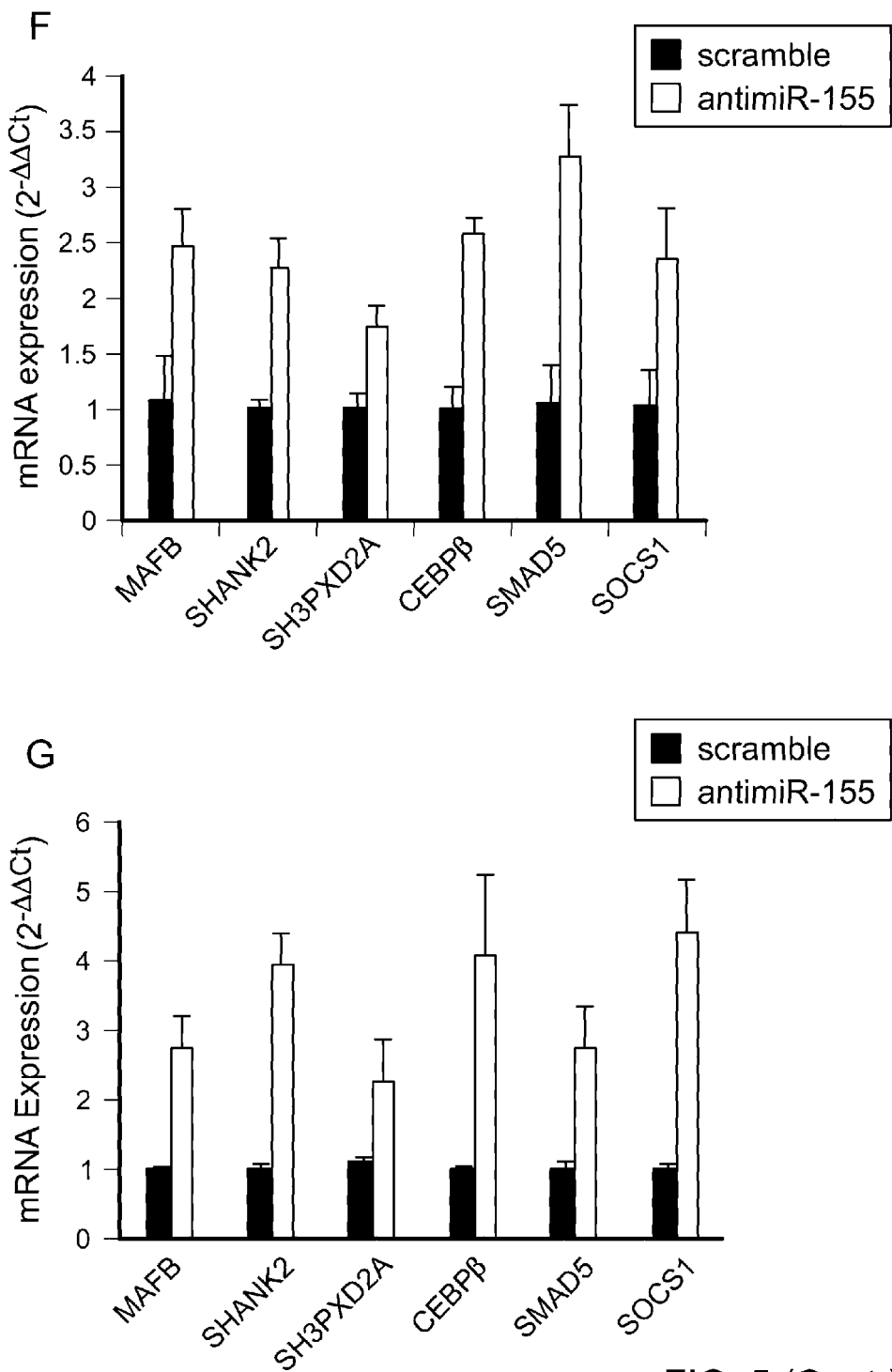

To identify new direct miR-155 targets in B cell lymphomas, gene expression profiling (GEP) was performed on BCWM.1 cells after treatment with antimiR-155 or scramble control for 24 or 48 hours. Based on GEP data, several validated miR-155 target mRNAs, such as CEBPβ, SMAD5, and SOCS1 were found to be up-regulated in the BCWM1 cells after treatment with antimiR-155 compared to cells treated with scramble control (FIG. 5B). Moreover, three potential new targets of miR-155 were identified, namely MAFB, SHANK2, and SH3PXD2A, as predicted by TargetScan software, which were de-repressed 48 hours after antimiR-155 treatment (FIG. 5B). These findings were further validated by qRT-PCR, which confirmed the array data from antimiR-155 treated BCWM1 cells (FIG. 5C).

To functionally validate the miR-155 target mRNA interactions, luciferase 3' UTR reporters for MAFB, SHANK2 and SH3PXD2A were generated. To this end, RNAhybrid was used to depict the miR-155 target sites in the 3'UTRs of MAFB, SHANK2 and SH3PXD2A, followed by cloning of the wild-type and mutated target sequences into the pMiR-GLO vector. After transfection of the luciferase reporters into HEK293 cells stably expressing copGFP control plasmid or HEK293 cells stably expressing pre-miR-155, dual luciferase activity was measured. A significant repression of the luciferase activity was observed for all 3' UTR reporters containing a perfect match target site, while there was no change in luciferase activity for the reporters harboring mutations in the miR-155 target site sequences, implying that MAFB, SHANK2 and SH3PXD2A are indeed bona fide targets of miR-155 (FIG. 5D).

The mRNA levels of the six miR-155 target genes, SMAD5, SOCS1, CEBPβ, MAFB, SHANK2 and SH3PXD2A, in BCWM1 cells were next determined by qRT-PCR from primary WM CD19+ cells, and primary CLL cells, normal donor blood CD19+ cells, BCWM1 and MEC1 cells. All six targets were significantly down-regulated in malignant cells in WM or CLL compared to normal control CD19+ cells (FIG. 5E). Moreover, treatment of primary WM CD19+ cells or primary CLL cells with 20 μM antimiR-155 for 48 hours showed a significant increase in the mRNA levels of the six miR-155 targets compared to scramble control treated cells as judged by qRT-PCR (FIGS. 5F and 5G).

In summary, these data indicate that the mRNAs of SMAD5, SOCS1, CEBPβ, MAFB, SHANK2 and SH3PXD2A are negatively regulated by miR-155 in WM and CLL. MAFB belongs to the MAF family of basic leucine zipper transcription factors (Kataoka K. et al., *Mol. Cell. Biol.*, 14(11):7581-7591 (1994)). Combined deficiency for the transcription factors MAFB and c-Maf enables self-renewal of differentiated functional macrophages (Aziz A. et al., *Science*, 326(5954):867-871(2009)). Mostly, Maf genes including MAFB are bona fide oncogenes as highlighted by studies from their initial isolation to their involvement in human cancer (Eychene A. et al., *Nat. Rev. Cancer,* 8(9):683-693 (2008)). For example, in humans, Maf genes are over-expressed in about 60% of human angioimmunoblastic T-cell lymphomas (Morito N. et al., *Cancer Res.,* 66(2):812-819 (2006)), and in about 50% of multiple myeloma cases, in which they contribute directly to cancer progression (Hideshima T. et al., *Blood,* 104(3):607-618 (2004); Hurt E. M. et al., *Cancer Cell,* 5(2):191-199 (2004)). However, Maf proteins can be either pro- or anti-oncogenic, depending on the cell context, where the anti-oncogenic activity has been linked to their strong terminal differentiating activity (Pouponnot C. et al., *Oncogene,* 25(9):1299-1310 (2006)). Thus, miR-155 appears to control cell proliferation through MAFB, and MAFB may function as a tumor suppressor in B cell malignancies, since the expression level of MAFB in lymphoma was found to be lower compared to normal cells.

Example 7. Delivery of AntimiR-155 into Engrafted WM Cells in Recipient Mice

Figure 6:
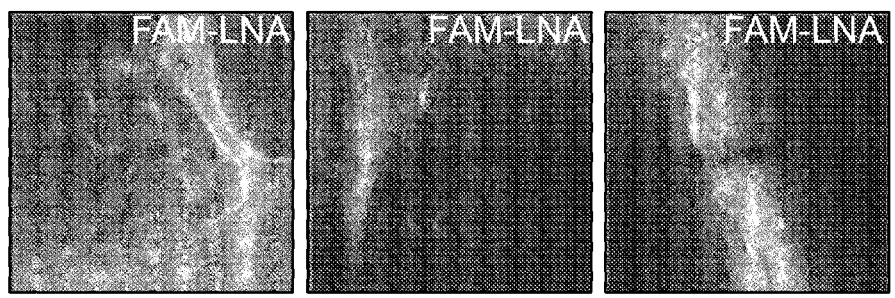
FIG. 6A is a series of confocal images showing the distribution of FAM-labeled antimiR-155 in cells from mice calvarium bone marrow. The images show that FAM-labeled antimiR-155 was successfully taken up by cells present in the bone marrow and was detected up to 2 weeks after a single tail vein injection of the antimiR-155 compound.
FIG. 6B is a series of immunofluorescence images showing the distribution of FAM-labeled antimiR-155 in cells from mice organs. The distribution of FAM-labeled antimiR-155 was also examined in cells of other tissues in the hematopoietic system of the mice, including spleen and femoral bone marrow by immunofluorescence. The data showed that the FAM-labeled antimiR-155 was widely distributed in both spleen and bone marrow. Bar=100 μm.
FIG. 6C are histograms showing the distribution of FAM-labeled antimiR-155 in bone marrow, spleen and liver as measured by flow cytometry. Statistical analysis of flow cytometry is shown in the lower panel as a bar graph. Mean±SD. **, P<0.01.
FIG. 6D is a series of immunofluorescence images showing the distribution of FAM-labeled antimiR-155 in cells from organs of mice. Although seven mice were studied, data from only three representative mice are shown here. SCID mice were engrafted with 3×10$^6$ mCherry-Luc$^+$-BCWM1 cells, followed by a single intravenous tail vein injection of 25 mg/kg FAM-labeled antimiR-155 or saline. Two weeks after injection, mouse femoral bone marrow and spleen were collected for immunofluorescence imaging. The results indicate that FAM-labeled antimiR-155 could be taken up by engrafted WM cells in the bone marrow and spleen of recipient mice. Bar=100 μm.
Figure 6:
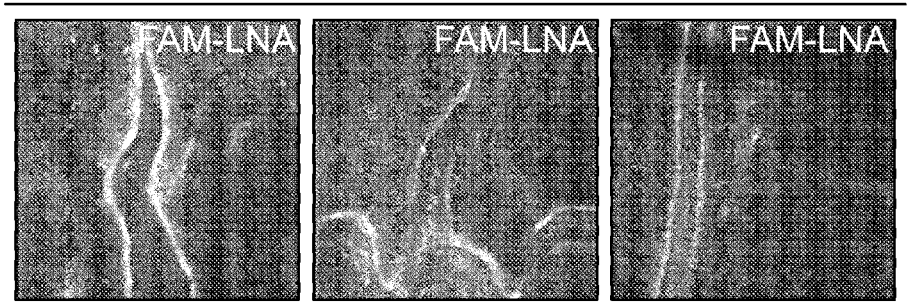
Figure 6:
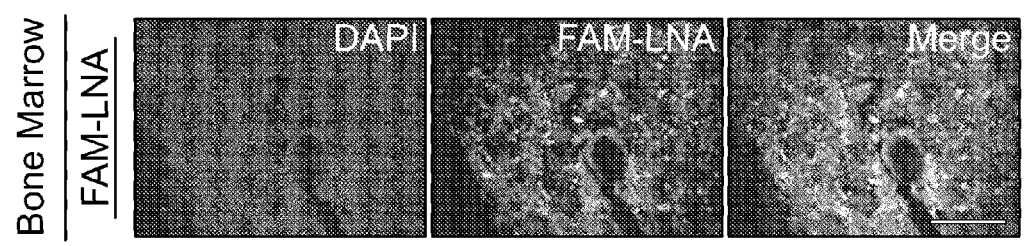
Figure 6:
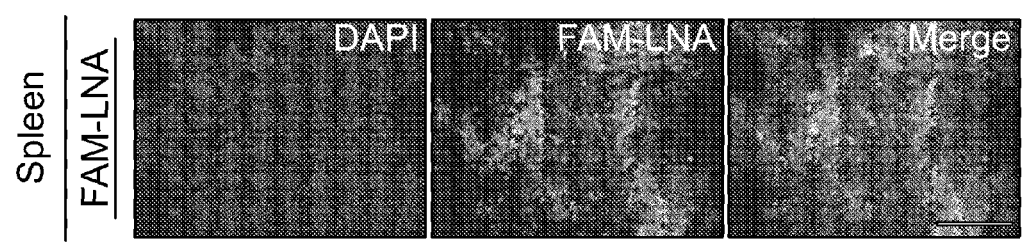
Figure 6:
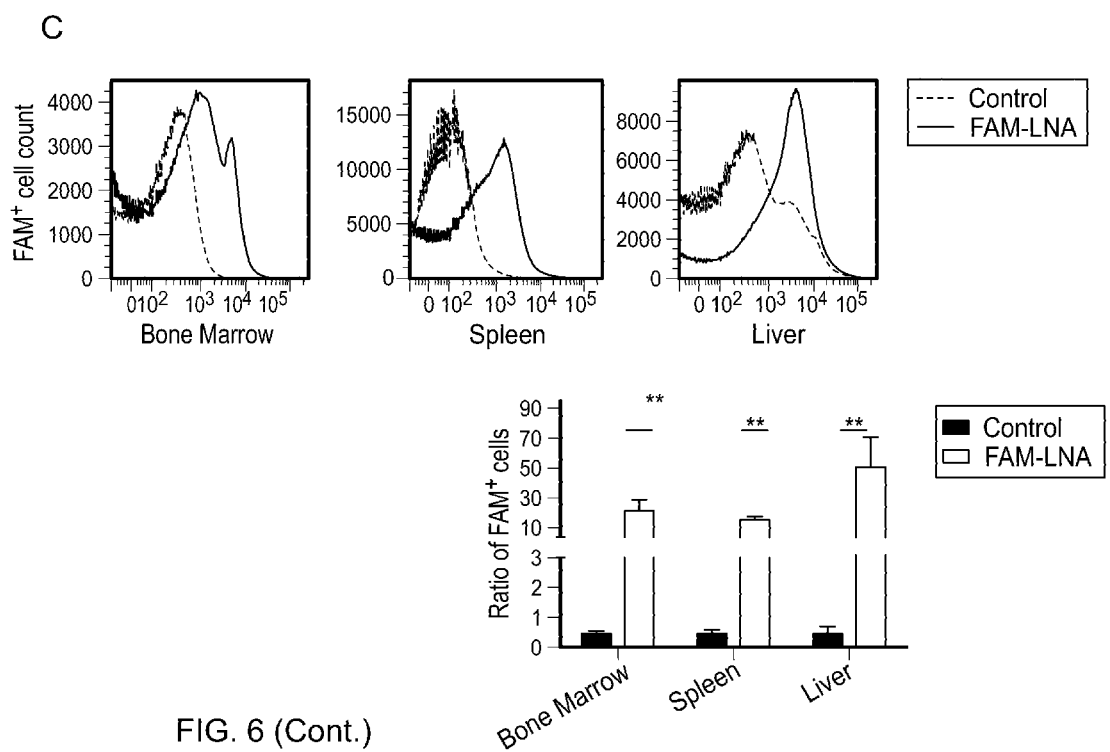
Figure 6:
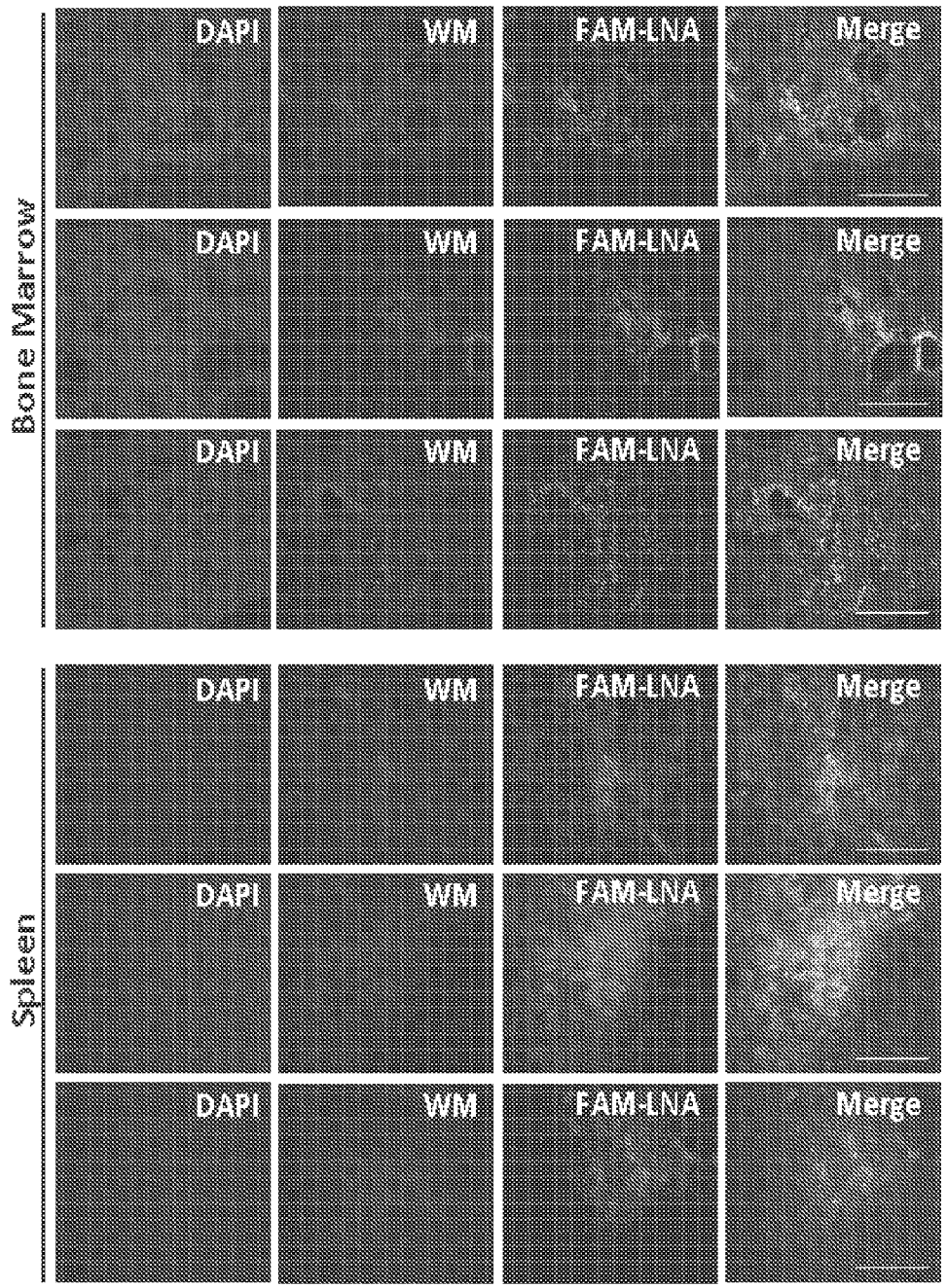

This experiment investigated whether antimiR-155 could be delivered to the bone marrow where low-grade B cell malignancies primarily reside. Balb/c mice were dosed with a single intravenous tail vein injection of 25 mg/kg FAM-labeled antimiR-155 or saline control and examined for distribution after one week and two weeks by live in vivo confocal imaging. As shown in FIG. 6A, the FAM-labeled antimiR-155 was successfully taken up by cells present in the bone marrow and was detected up to 2 weeks after a single tail vein injection of the antimiR-155 compound. The distribution of FAM-labeled antimiR-155 was also examined in cells of other tissues in the hematopoietic system of the mice, including spleen and femoral bone marrow by immunofluorescence. The data showed that the FAM-labeled antimiR-155 was widely distributed in both spleen and bone marrow, which showed high levels of infiltrated malignant B cells in WM and CLL (FIG. 6B). Furthermore, the distribution of FAM-labeled antimiR-155 in cells from the femur, spleen and liver were examined using flow cytometry analysis to quantify the ratio of cells that were positive for FAM-labeled antimiR-155. As shown in FIG. 6C, there was a significant shift in the number of FAM-positive cells. Taken together, these data indicate that the antimiR-155 could be efficiently delivered and taken up by cells of the hematopoietic system.

It was next investigated whether the antimiR-155 compound could be effectively delivered into WM cells in vivo. To this end, seven SCID mice per group were engrafted with $3 \times 10^6$ mCherry-Luc$^+$-BCWM1 cells, followed by a single intravenous tail vein injection of 25 mg/kg FAM-labeled antimiR-155 or saline. Two weeks after injection, mouse femoral bone marrow and spleen were collected for immunofluorescence imaging, and as shown in FIG. 6D, the results indicate that FAM-labeled antimiR-155 could be taken up by engrafted WM cells in the bone marrow and spleen of recipient mice.

Figure 7:
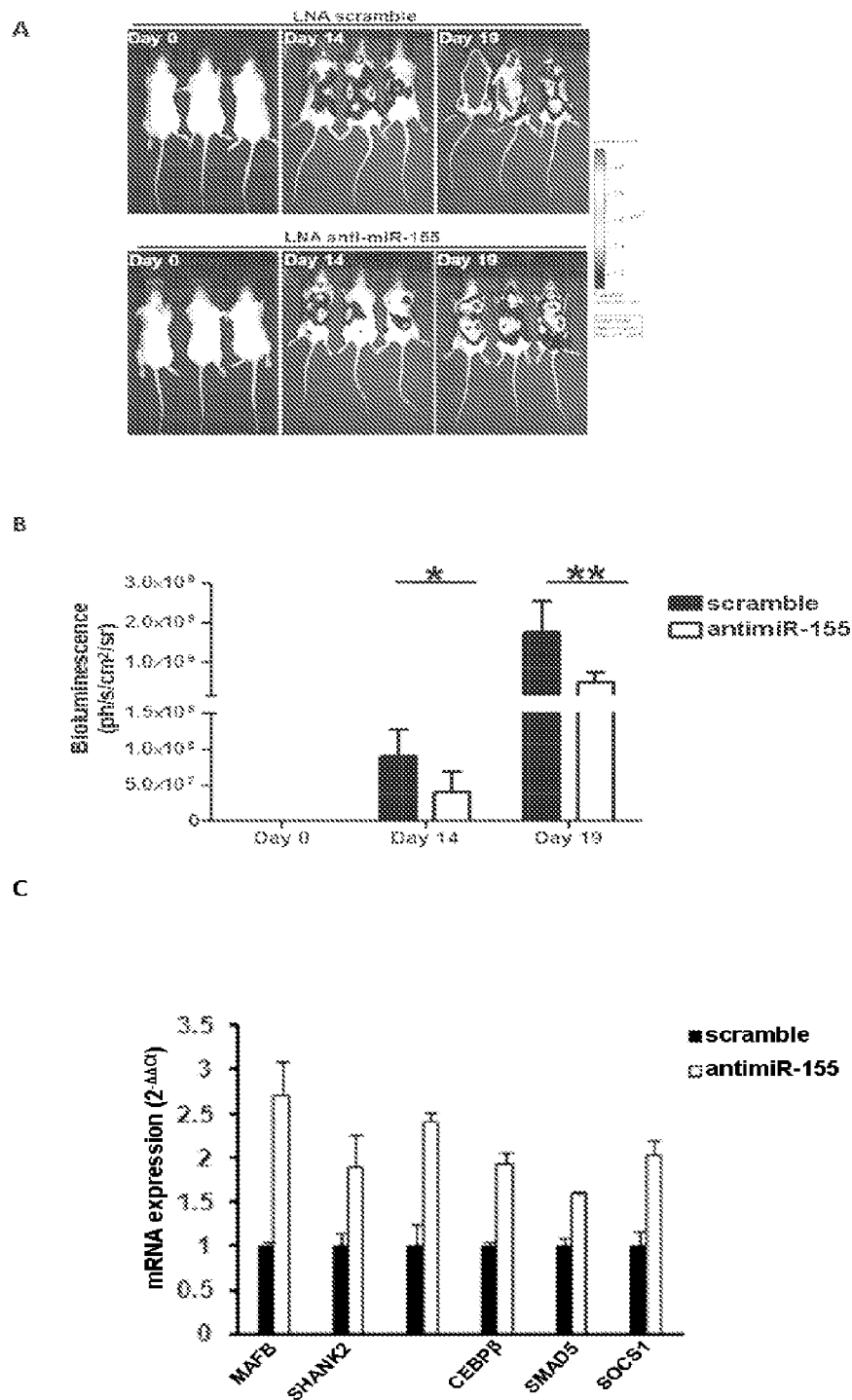
FIG. 7A is a series of photographs of bioluminescent Imaging (BLI) of tumor burden from mice injected with mCherry-Luc$^+$-BCWM1 cells at Day 0, Day 14, or Day 19 after injection.
FIG. 7B is a bar graph showing that treatment with the antimiR-155 significantly decreased tumor burden compared to scramble control. P=0.024 at Day 14; P=0.009 at Day 19. n=6 (per group). Mean±SD. *, P<0.05; **, P<0.01.
FIG. 7C is a bar graph showing mRNA levels of miR-155 targets detected by qRT-PCR in the bone marrow CD19$^+$ cells from mice treated with antimiR-155 or LNA scramble control. Experiments were performed in triplicate and repeated three times. Mean±SD.
FIG. 7D is a series of images obtained by immunofluorescent imaging of protein levels of the miR-155 target gene MAFB from the femur, bone marrow, or spleen of mice. MAFB was detected by immunostaining with anti-MAFB. Immunostaining confirmed de-repression of the MAFB at the protein level in the bone marrow and spleen upon treatment with the antimiR-155.
FIG. 7E is a series of images obtained by immunofluorescent imaging of protein levels of the miR-155 target gene CEBPβ from the femur, bone marrow, or spleen of mice. CEBPβ was detected by immunostaining with anti-CEBPβ. Immunostaining confirmed de-repression of the CEBPβ targets at the protein level in the bone marrow and spleen upon treatment with the antimiR-155.
Figure 7:
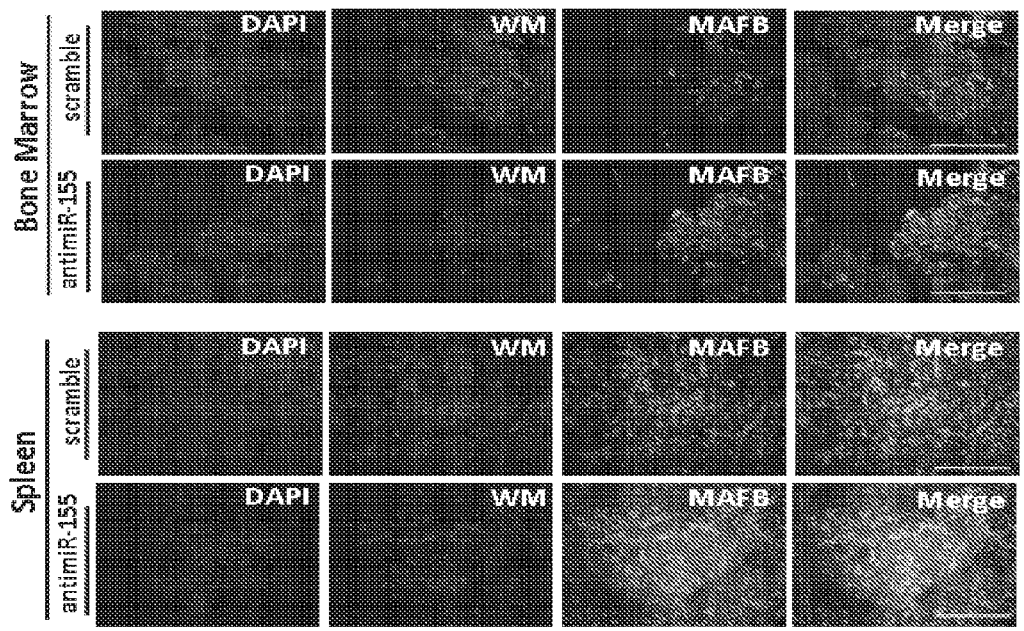
Figure 7:
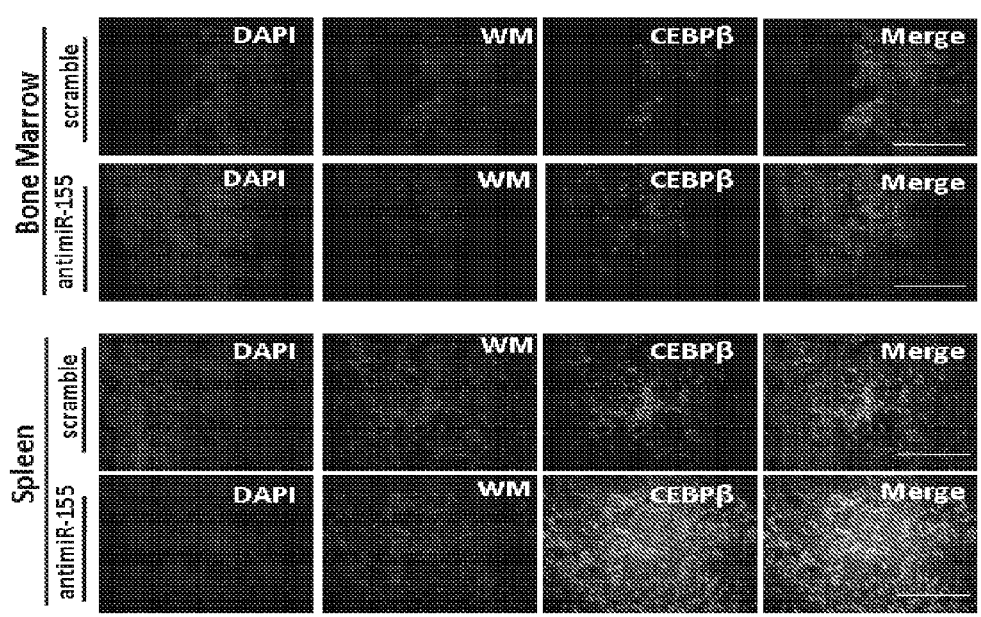

Example 8: Inhibition of miR-155 Decreases Tumor Growth in a Xenograft Mouse Model of WM To assess the anti-tumor activity of antimiR-155 in vivo, a xenograft mouse model of WM was used. Six SCID mice per group were engrafted with $3 \times 10^6$ mCherry-Luc$^+$-BCWM1 cells, after which mice were injected with a loading dose of 25 mg/kg antimiR-155 or scramble control, which was followed by weekly maintenance doses of 5 mg/kg of each respective compound until the mice were sacrificed. Tumor burden was monitored using bioluminescent imaging (BLI) at Days 0, 14, and 19 after injection (FIG. 7A). Image analysis showed that there was a significant reduction in tumor burden at Day 14 and Day 19 in the antimiR-155 treated mice compared to mice treated with the scramble control (FIG. 7B). No difference in body weight was identified between the two groups (data not shown).

The mRNA levels of six miR-155 targets in the bone marrow WM CD19$^+$ cells were quantified by qRT-PCR, which showed that expression of all six targets was de-repressed after treatment with the antimiR-155 compared to scramble control (FIG. 7C). Moreover, immunostaining confirmed de-repression of the MAFB and CEBPβ targets at the protein level in the bone marrow and spleen upon treatment with the antimiR-155 (FIG. 7D).

Taken together, these data indicate that antimiR-155 mediated silencing of miR-155 in a xenograft mouse model of WM leads to de-repression of expression of direct miR-155 targets in the bone marrow WM CD19$^+$ cells and decreases the tumor growth in recipient mice.

Figure 8:
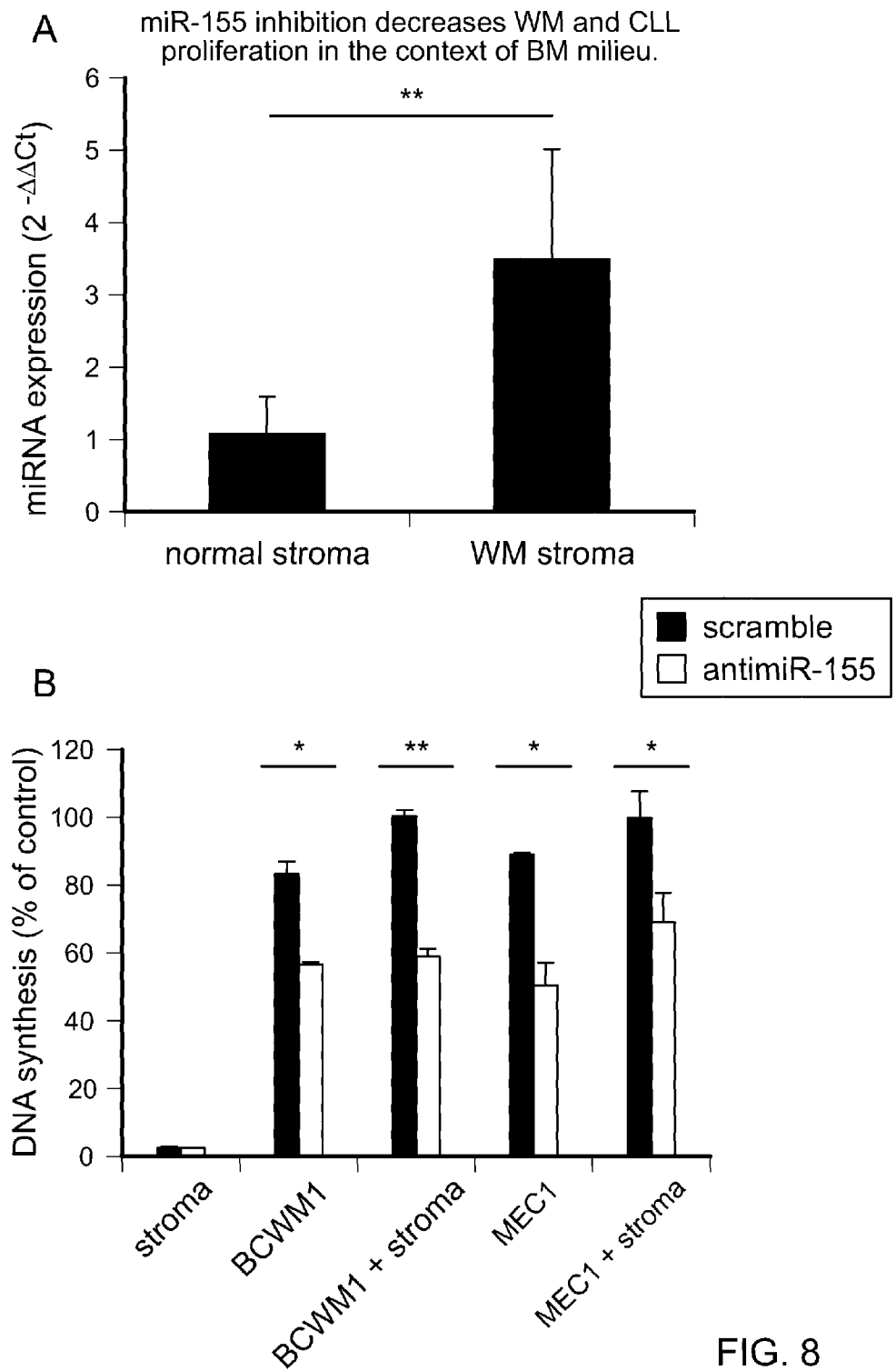
FIG. 8A is a bar graph showing qRT-PCR analysis of miR-155 levels in WM stroma (N=10) compared to normal stroma (N=3). Mean±SD. **, P<0.01.
FIG. 8B is a bar graph showing cell proliferation (evaluated by [H]$^3$ thymidine uptake assay) of BCWM1 or MEC1 cells treated with 20 μM antimiR-155 or scramble control for 48 hours, followed by co-culture with stromal cells from WM patients. Experiments were performed in triplicate and repeated three times. Mean±SD. *, P<0.05; **, P<0.01.
FIG. 8C is a bar graph showing cell proliferation (evaluated by [H]3 thymidine uptake assay) of BCWM1 or MEC1 cells co-cultured with stromal cells from wild-type or miR-155−/− knockout mice. Experiments were performed in triplicate and repeated three times. Mean±SD. **, P<0.01.
FIG. 8D is a bar graph showing cell proliferation (evaluated by [H]3 thymidine uptake assay) of BCWM1 or MEC1 cells treated with 20 μM antimiR-155 or scramble control for 48 hours, followed by co-culturing with stromal cells from wild-type or miR-155−/− knockout mice. Experiments were performed in triplicate and repeated three times. Mean±SD. *, P<0.05; **, P<0.01.
Figure 8:
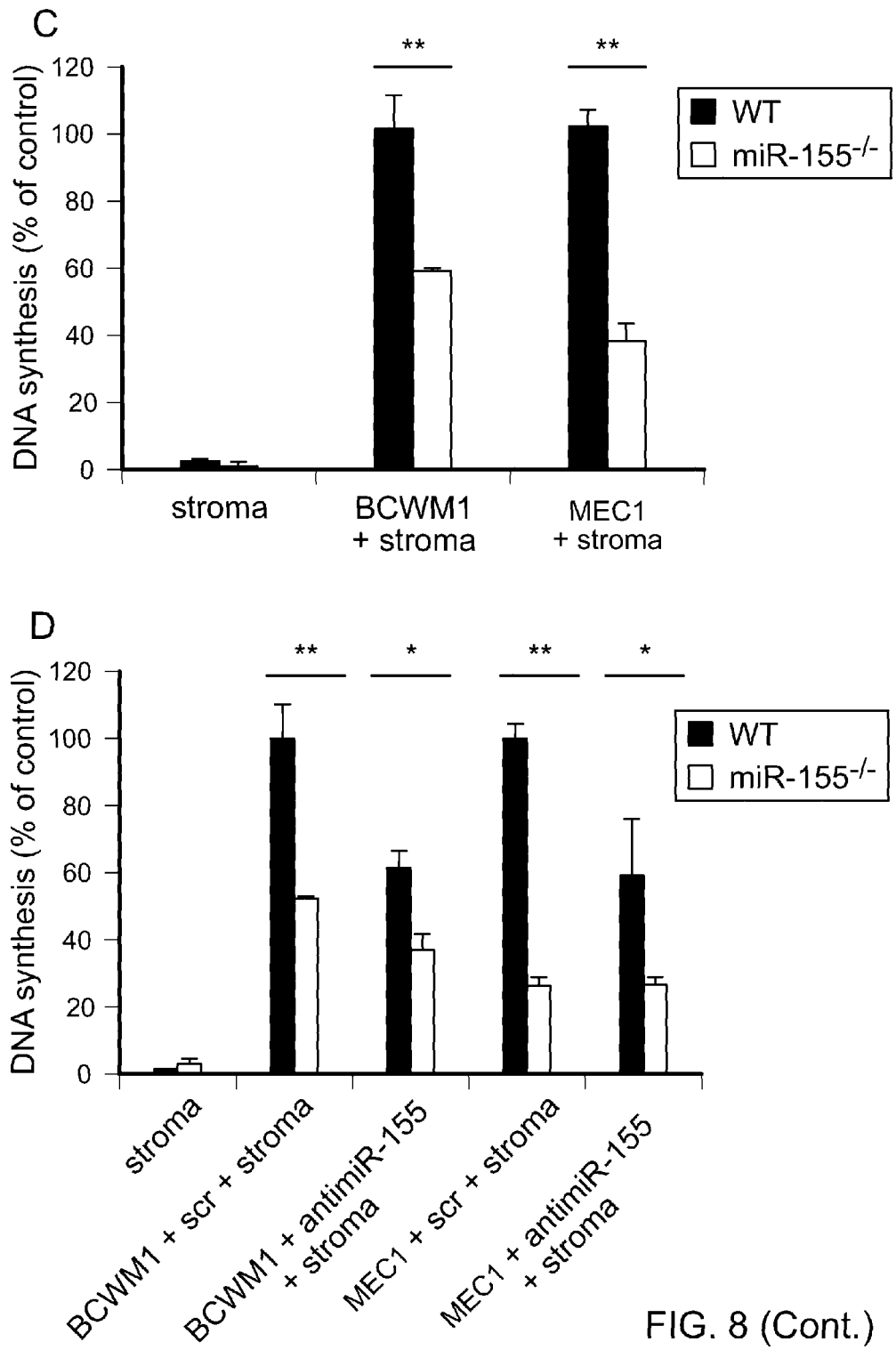

Example 9. Inhibition of miR-155 Decreases WM and CLL Proliferation in the Context of the Bone Marrow Microenvironment To examine the effect of antimiR-155 on tumor progression in the context of the microenvironment, the miR-155 levels were first quantified in bone marrow stromal cells (mesenchymal stem cells) from WM patients in comparison to normal healthy donors. It was found that miR-155 levels in WM stromal cells were higher compared to healthy donor bone marrow stromal cells (FIG. 8A). Consequently, 20 μM antimiR-155 or scramble control was added to a co-culture of BCWM1 and primary WM bone marrow stromal cells or MEC1 cells and primary WM bone marrow stromal cells, and then assessed for cell proliferation by MTT and [H]$^3$ thymidine uptake assays, respectively, after 48-hours. The results indicate that antimiR-155 treatment not only decreased tumor cell proliferation, but also overcame the protective effect of bone marrow stromal cells on WM tumor cells (FIG. 8B). No effect on cell cytotoxicity on stromal cells was observed.

Since the bone marrow microenvironment plays a critical role in supporting tumor cell growth, it was sought to examine the role of miR-155 in tumor proliferation specifically in bone marrow stromal cells. BCWM1 or MEC1 cells were co-cultured with bone marrow stromal cells from miR-155$^{-/-}$ (miR-155 knockout) mice or wild-type mice as control. Cell cytotoxicity and cell proliferation were assessed after 48-hour of co-culture. The stromal cells from miR-155$^{-/-}$ mice significantly inhibited proliferation of BCWM1 and MEC1 cells compared to stromal cells from wild type mice, indicating that miR-155 may also play an important role in the surrounding microenvironmental cells lending significant support to tumor growth and proliferation (FIG. 8C).

To further clarify whether antimiR-155 can affect both tumor cells and stromal cells, BCWM1 or MEC1 cells were treated with antimiR-155 or scramble control, followed by co-culturing of the treated cells with bone marrow stromal cells from wild-type mice in comparison with stromal cells from miR-155$^{-/-}$ mice. Cell survival and cell proliferation were assessed by MTT assay and [H]$^3$ thymidine uptake assays, respectively, after 48-hour of co-culture. The data showed that treatment with antimiR-155 decreased tumor cell proliferation compared to scramble control when co-cultured with wild-type mice stroma, but not significantly upon co-culturing with miR-155$^{-/-}$ stromal cells, indicating that the antimiR-155 treatment leads to a similar effect on WM as the genetic miR-155 loss-of-function (FIG. 8D).

Example 10. Materials and Methods for Examples 11-13 a) Cells:

Primary WM cells were obtained from bone marrow (BM) samples of previously treated WM patients using CD19$^+$ microbead selection (Miltenyi Biotec, Auburn, Calif.) with over 90% purity, as confirmed by flow cytometric analysis with monoclonal antibody reactive to human CD20-PE (BD-Bioscience, San Jose, Calif.). The WM and the IgM secreting lymphoma cell lines (BCWM.1; MEC.1; RL) were used in this study (Roccaro A. M. et al., *Blood*, 111(9):4752-63 (2008)). Peripheral blood mononuclear cells (PBMCs) were obtained from healthy subjects by Ficoll-Hipaque density sedimentation and CD19+ selection was performed as described above. All cells were cultured at 37° C. in RPMI-1640 containing 10% fetal bovine serum (FBS; Sigma Chemical, St Louis, Mo.), 2 mM L-glutamine, 100 U/mL penicillin, and 100 µg/mL streptomycin (GIBCO, Grand Island, N.Y.). Approval for these studies was obtained from the Dana-Farber Cancer Institute Institutional Review Board. Informed consent was obtained from all patients and healthy volunteers in accordance with the Declaration of Helsinki protocol.

b) Reagents:

Everolimus (the 40-O-(2-hydroxyethyl) derivative of sirolimus (rapamycin)) was provided by Novartis, and diluted in DMSO and stored at 4° C. until use, then diluted in culture medium immediately before use. The maximum final concentration of DMSO (<0.1%) did not affect cell proliferation and did not induce cytotoxicity on the cell lines and primary cells tested (data not shown). Bortezomib and Rituximab were obtained from Hospital Pharmacy.

c) Growth Inhibition Assay:

The inhibitory effect of everolimus on the growth of WM cells, IgM secreting cell lines, and primary cells was assessed by measuring 3-(4,5-dimethylthiazol-2-yl)-2,5-diphenyltetrazolium bromide (MTT; Chemicon International, Temecula, Calif.) dye absorbance, as previously described (Roccaro A. M. et al., *Blood*, 113(18):4391-402 (2009)).

d) DNA Synthesis:

DNA synthesis was measured by [$^3$H]-thymidine ([$^3$H]-TdR; Perkin Elmer, Boston, Mass.) uptake, as previously described (Roccaro A. M. et al., *Blood*, 113(18):4391-402 (2009)).

e) DNA Fragmentation:

Cell Death Detection ELISA (Roche Applied Science, Indianapolis, Ind.) was used to quantify DNA fragmentation, as per the manufacturer's instructions, and as previously described (Sacco A. et al., *Clin Cancer Res.*, 17(7):1753-64 (2011)).

f) Immunoblotting:

WM and IgM secreting cell lines were harvested and lysed using lysis buffer (Cell Signaling Technology, Beverly, Mass.) reconstituted with 5 mM NaF, 2 mM Na$_3$VO$_4$, 1 mM PMSF (polymethilsulfonyl fluoride), 5 µg/mL leupeptine, and 5 µg/mL aprotinin. Whole-cell lysates (50 µg/lane) were subjected to sodium dodecyl sulfate-polyacrylamide gel eletrophoresis (SDS-PAGE) and transferred to polyvinyldene fluoride (PVDF) membrane (Bio-Rad Laboratories, Hercules, Calif.). The antibodies used for immunoblotting included: anti-caspase3-, -caspase-9, -PARP, phospho (p)-mTOR, p-p70S6K, p-4EBP1, p-FAK-cyclinD1, -cyclinD2-p27$^{Kip1}$, -p21$^{Cip1}$, p-Akt, -Akt, pERK, -ERK, p-GSK3, -p-STAT3, -p-p65, -p-p50, -p-IkB, -nucleolin and -tubulin antibodies (Cell Signaling, Danvers, Mass.).

g) Caspase Activation:

WM cell lines have been exposed to everolimus (0.1-10 nM) for 24 hours and caspase activation has been assessed using Caspase 3/7 Glo Assay (Promega, Madison, Wis.), according to manufacturer's procedure.

h) Effect of Everolimus on Paracrine WM Cell Growth in the BM:

To evaluate growth stimulation and signaling in WM cells adherent to bone marrow stromal cells (BMSCs), 3×10$^4$ BCWM.1 cells were cultured in BMSC-coated 96-well plates for 48 hours in the presence or absence of everolimus. DNA synthesis was measured as described (Roccaro A. M. et al., *Blood*, 111(9):4752-63 (2008)).

i) Transwell Migration Assay:

Transwell migration assay (Costar; Corning, Acton, Mass.) was performed using BCWM.1 cells in the presence or absence of 30 nM SDF-1, as described (Azab A. K., et al., *Blood*, 114(3):619-29 (2009)).

j) Cell Cycle Analysis:

BCWM.1 cells were stained with propidium iodine (PI; Sigma Chemical) and cell cycle was determined using an Epics (Coulter Immunology, Hialeah, Fla.) flow cytometry, as previously described (Roccaro A. M. et al., *Blood*, 113 (26):6669-80 (2009)).

k) Antibody-Dependent Cell-Mediated Cytotoxicity Assay (ADCC):

ADCC was performed as previously described (Leleu X. et al., *Blood*, 111(10):5068-77 (2008)). Briefly, interleukin-2 (IL-2; R&D, Minneapolis, Minn.)-activated PBMCs were used as effector cells and calcein-AM-labeled BCWM.1 cell line, as targets. PBMCs were separated from leukopheresis products from healthy donors over Ficoll-Hypaque solution after informed consent. Effector cells were used immediately at 37° C. in RPMI complete media after being activated with IL-2 (100 UI/mL for 36 hours). Target cells were labeled with calcein-AM for 1 hour at 37° C., washed thrice, and plated in triplicate in 96-well plates (5000 cells per well). ADCC was performed in the presence of rituximab (10 µg/mL) or human control IgG1 (2 ng/mL) at various effector-target (E/T) ratios (10:1, 20:1, and 40:1). The 96-well plates were centrifuged at 30 g for 2 minutes at room temperature, followed by a 4-hour incubation at 37° C. Culture supernatants were transferred to a Black ViewPlate-96 plate and read on Wallac VICTOR2 using 492/520 nm filter set (Perkin Elmer). Combinatory studies using everolimus (1 nM), Bortezomib (5 nM) and Rituximab (10 µg/mL) were also performed. This assay was valid only if (mean maximum release−medium control release)/(mean spontaneous release−medium control release) was more than 7. Spontaneous release is the CPM in the supernatant from wells containing target cells alone. Maximum release is the supernatants of wells containing target cells and Triton X-100. Experimental release is obtained from the supernatant of wells containing effector cells, target cells, and antibody. Calculation of percentage specific lysis from triplicate experiments was done using the following equation: % specific lysis=100×[(mean experimental release−mean spontaneous release)/(mean maximum release−mean spontaneous release)].

l) NF-κB Activity:

NF-κB activity was investigated using the Active Motif TransAM kits, a DNA-binding enzyme-linked immunosorbent assay (ELISA)-based assay (Active Motif North America, Carlsbad, Calif.). Briefly, BCWM.1 cells were treated with everolimus (1 nM) or bortezomib (5 nM) alone or in combination for 4 hours, and stimulated with TNF-α (10 ng/mL) during the last 20 minutes of culture. NFκBp65 transcription factor binding to its consensus sequence on the plate-bound oligonucleotide was studied from nuclear extracts, following the manufacturer's procedure (Roccaro A. M. et al., *Blood,* 111(9):4752-63 (2008)).

m) Morphogenesis Assay on Matrigel:

Unpolymerized Matrigel (17 mg/mL; Becton Dickinson, Mountain View, Calif.) was placed (50 μL/well) in a 96-well microtiter plate (0.32 cm2/well) and polymerized for 1 hour at 37° C. HUVECs and MMECs (5×103 per well) in 200 μL of DMEM/10% FCS (positive control), serum-free medium (negative control), as well as in the presence or absence of everolimus (0-0.01-0.1-1-10 nM) were layered onto the Matrigel surface. After 6 hours of incubation in a 5% $CO_2$ humidified atmosphere at 37° C., cell growth and tridimensional organization were observed using a reverted phase-contrast light microscope, as described (Roccaro A. M. et al., *Cancer Res.,* 66(1):184-91 (2006)).

n) Immunofluorescence:

The effect of everolimus in combination with the proteasome inhibitor bortezomib (marketed as VELCADE®) on tumor necrosis factor-α (TNF-α)-induced nuclear translocation of p65 was examined by an immunocytochemical method. Briefly, BCWM.1 cells were cultured in presence or absence of everolimus (1 nM) and bortezomib (5 nM) for 4 hours, and then stimulated with TNF-α (10 ng/mL) during the last 20 minutes of culture Immunocytochemical analysis was performed using an epifluorescence microscope (Nikon Eclipse E800; Nikon, Avon, Mass.) and a Photometrics Coolsnap CF color camera (Nikon, Lewisville, Tex.), as previously described. Similarly, evaluation of p-S6R has been evaluated by using immunofluorescence on WM cells treated with everolimus (1 nM), bortezomib (5 nM), the anti-CD20 antibody, rituximab (10 μg/mL), either alone or in combination (Roccaro A. M. et al., *Blood,* 111(9):4752-63 (2008)).

o) Immunohistochemistry:

Bone marrow biopsies from WM patients at pretreatment and at the end of therapy were fixed in Zenker's formalin, embedded in paraffin blocks, and sectioned. Sections were stained for phospho(p)-4EBP1 and p-S6R (Cell Signaling Technology, Inc.). Signal quantification for each target was obtained from four different areas, on matched pre- and post-everolimus treatment of 4 patients presenting with partial response; and on matched pre- and post-everolimus treatment of 3 patients presenting with stable disease. Numbers of positive cells were obtained on 4 different fields of the bone marrow biopsy, and average and standard deviation provided, as previously described (Fingar D. C. et al., *Mol. Cell. Biol.,* 24(1):200-16 (2004).

p) Quantitative Reverse Transcription-PCR (qRT-PCR):

qRT-PCR for miRNA-155 (TaqMan microRNA Assays, Applied Biosystems, Foster City, Calif.) was performed on an *Applied Biosystems AB*7500 Real Time PCR system. All PCR reactions were run in triplicate and miRNA expression, relative to RNU6B, was calculated using the $2^{-\Delta\Delta ct}$ method (Roccaro A. M. et al., *Blood,* 113(18):4391-402 (2009)).

q) miRNA Transfection:

WM cells (BCWM.1; MWCL.1) were transfected with either miRNA-155 LNA knockdown probe (Exiqon, Vedbaek, Denmark) or control knockdown probe (Exiqon, Vedbaek, Denmark), at a final concentration of 40 nM, using Lipofectamine 2000 (Invitrogen, Carlsbad, Calif.) following manufacturer's instruction, and as previously described (Roccaro A. M. et al., *Blood,* 113(18):4391-402 (2009)).

r) Statistical Analysis:

Statistical significance of differences in drug-treated versus control cultures was determined using Student's t-test. The minimal level of significance was p<0.05. Drug synergism was analyzed by isobologram analysis using the CalcuSyn software program (Biosoft, Ferguson, Mo.), as described (Roccaro A. M. et al., *Blood,* 111(9):4752-63 (2008)). Experiments have been repeated in triplicates. Error bars reported in the figures represent standard deviations.

Example 11. Mechanisms of Everolimus-Dependent Anti-WM Activity

Figure 9:
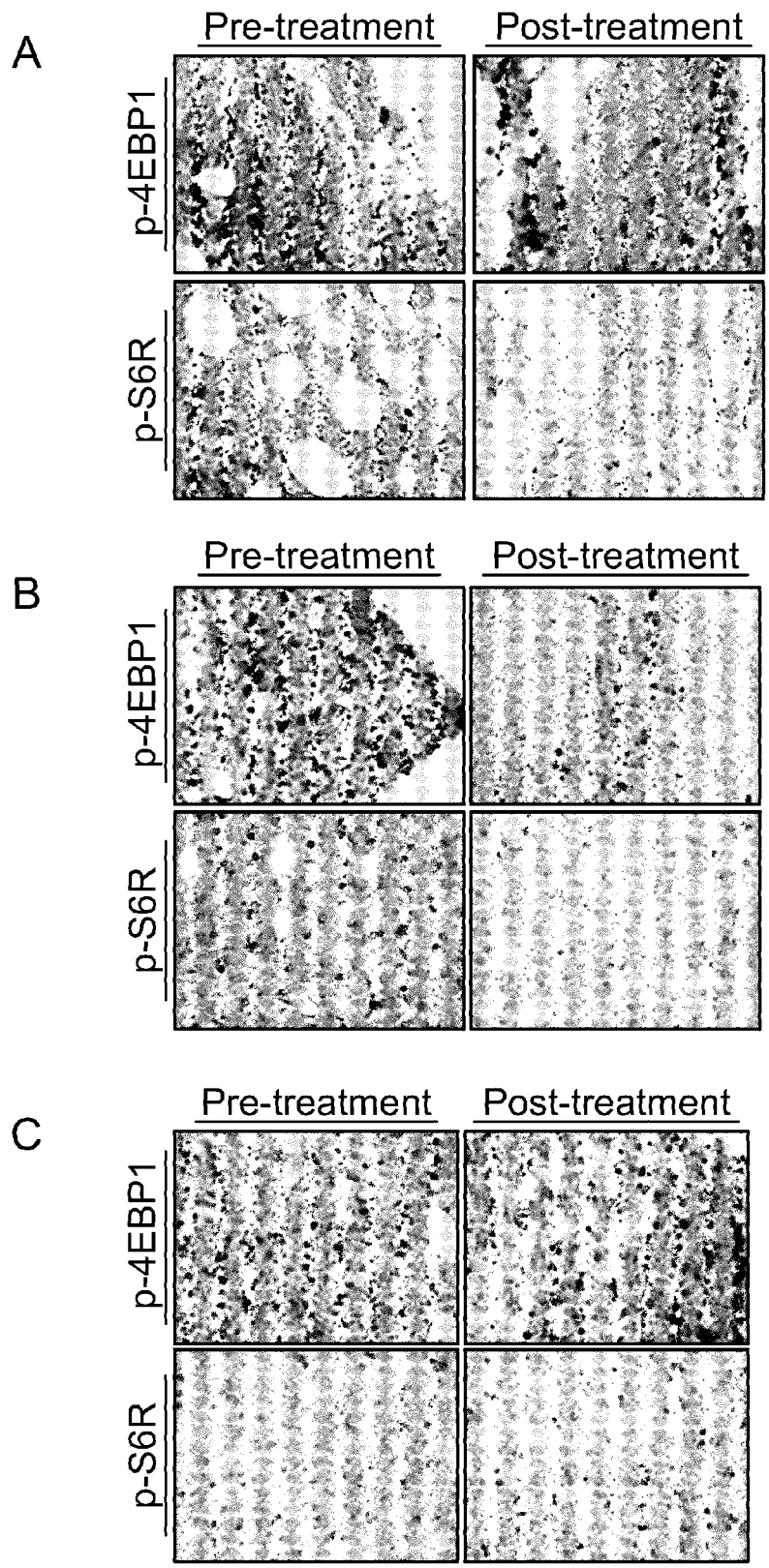
FIG. 9A is a series of images of immunohistochemistry of phosphorylated(p)-4EBP1 and p-S6R in pre- and post-everolimus treated WM patients that presented a partial response. The data demonstrated an inhibition of phosphorylation of ribosomal protein S6 (S6R) and eukaryotic translation initiation factor 4E-binding protein 1 (4EBP1).
FIG. 9B is a series of images of immunohistochemistry of phosphorylated(p)-4EBP1 and p-S6R in pre- and post-everolimus treated WM patients that presented a partial response. The data demonstrated an inhibition of phosphorylation of ribosomal protein S6 (S6R) and eukaryotic translation initiation factor 4E-binding protein 1 (4EBP1).
FIG. 9C is a series of images of immunohistochemistry of phosphorylated(p)-4EBP1 and p-S6R in pre- and post-everolimus treated WM patients that presented stable disease. Everolimus-dependent modulation of phosphorylated ribosomal protein S6 (phospho(p)-S6R) and p-4EBP1 was not observed in those patients with stable disease.

A recently conducted phase II trial of the oral mammalian target of rapamycin inhibitor everolimus (RAD001) in patients with relapsed or refractory WM demonstrated an overall response rate of 70%, with a partial response (PR) of 42% and 28% minor response (Ghobrial I. M. et al., *J. Clin. Oncol.,* 28(8):1408-14 (2010)). This study evaluated bone marrow biopsies of patients that presented with PR, and demonstrated an inhibition of phosphorylation of ribosomal protein S6 (S6R) and eukaryotic translation initiation factor 4E-binding protein 1 (4EBP1) (FIG. 9A-9B), indicating the ability of everolimus to specifically down-modulate the activity of two mammalian target of rapamycin (mTOR) downstream targeted proteins. In contrast, everolimus-dependent modulation of phosphorylated ribosomal protein S6 (phospho(p)-S6R) and p-4EBP1 was not observed in those patients with stable disease (FIG. 9C). These findings demonstrate the ability of everolimus to target mTOR in WM patients, resulting in anti-tumor activity.

Figure 10:
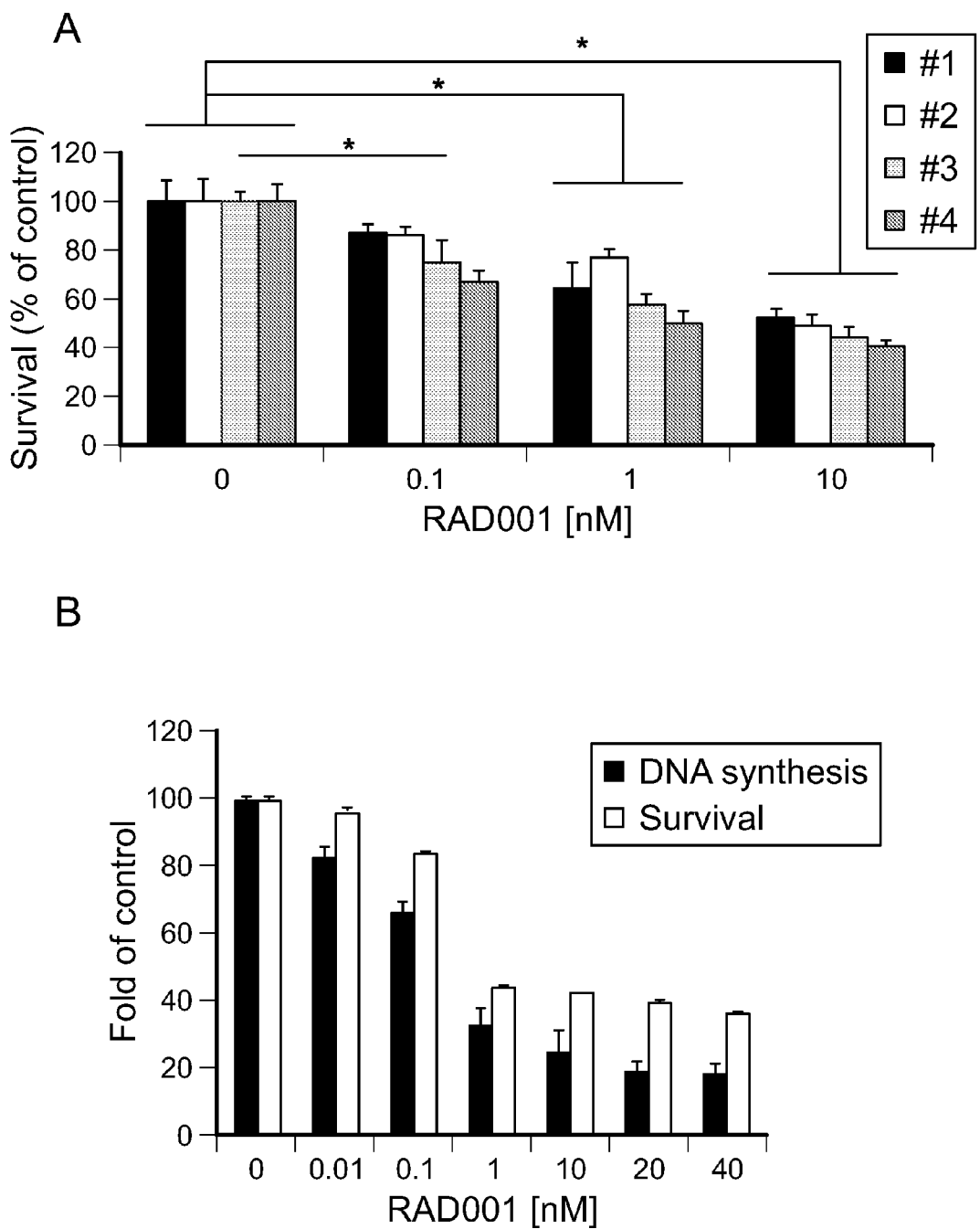
FIG. 10A is a bar graph showing percentage survival (x-axis) relative to treatment of primary WM bone marrow-derived CD19+ cells isolated from 4 patients having relapsed/refractory WM with everolimus 0.1-10 nM for 48 hours. Cytotoxicity was assessed by the MTT assay. Bars represent standard deviation.
FIG. 10B is a bar graph showing proliferation and survival compared to control of BCWM.1 cells cultured with everolimus (0.01-40 nM) for 48 hours. Cytotoxicity and cell proliferation were tested by the MTT assay and the thymidine uptake assay, respectively. Bars represent standard deviation.
FIG. 10C is a photograph of Western blots using anti-phospho(p)-mTOR, -p-p70S6K, -p-4EBP1 and -tubulin antibodies of whole cell lysates from BCWM.1 and MWCL.1 cells treated with everolimus (0.1-10 nM) for 6 hours.
FIG. 10D is a bar graph showing fold survival over control of WM-WSU, RL, MWCL.1 cells cultured with everolimus (0.01-40 nM) for 48 hours. Cytotoxicity was tested by the MTT assay. Bars represent standard deviation.
FIG. 10E is a bar graph showing fold survival over control of freshly isolated primary peripheral blood-derived CD19+ cells from 3 healthy donors, treated with everolimus (60-1000 nM), for 48 hours. Cytotoxicity was tested by the MTT assay. Bars represent standard deviation.
Figure 10:
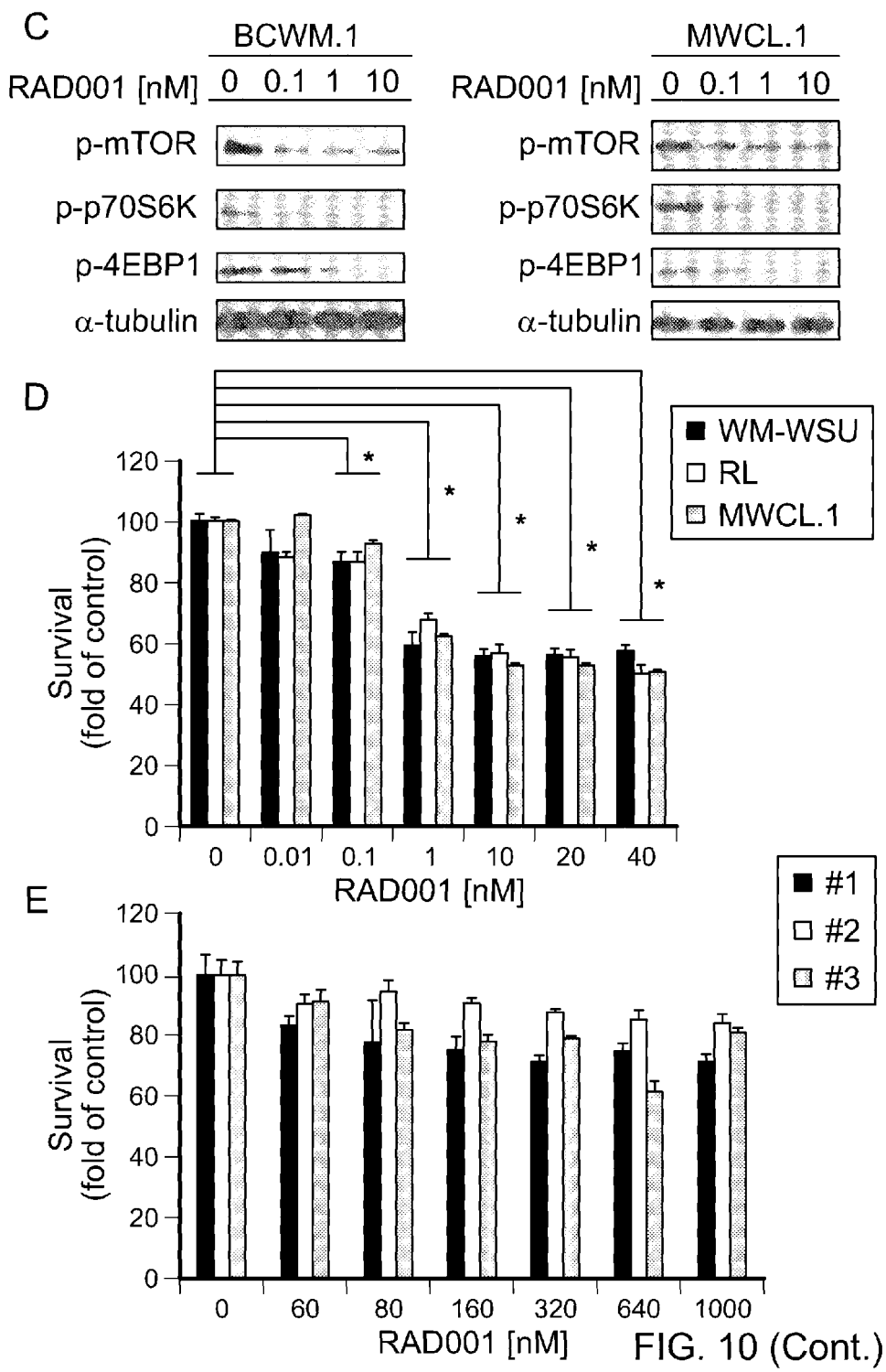
Figure 11:
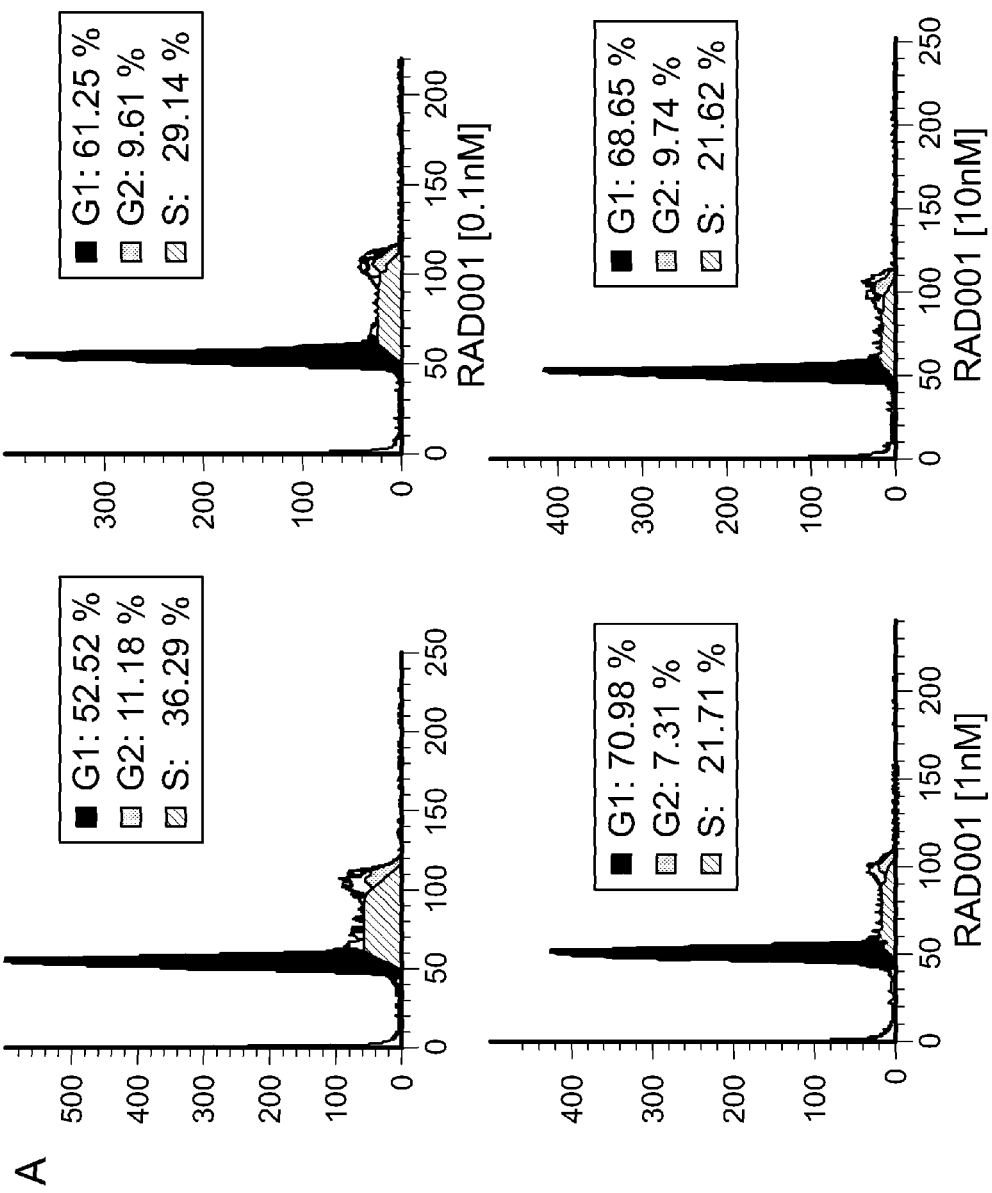
FIG. 11A is a series of histograms showing the distribution in the cell cycle of BCWM.1 cells cultured with everolimus (0.1-10 nM) for 12 hours. Cell cycle was assessed by PI staining and flow cytometry analysis.
FIG. 11B is a photograph of Western blots using anti-cyclin D1, -cyclin D2, -p27$^{Kip1}$, -p2$^{Cip1}$ and -α tubulin antibodies on whole cell lysates of BCWM.1 cells treated with everolimus (0.1-10 nM) for 12 hours.
FIG. 11C is a bar graph showing the percentage of DNA fragmentation (to assess apoptosis) in WM and low grade lymphoma IgM secreting cells (BCWM.1; MWCL.1; RL) treated with everolimus (0.1-10 nM) for 24 hours.
FIG. 11D is a photograph of Western blots using anti-PARP, -caspase-9, -caspase-3, and -α tubulin antibodies on whole cell lysates of BCWM.1 and MWCL.1 cells were treated with everolimus (0.1-10 nM) for 24 hours.
FIG. 11E is a bar graph showing percentage of caspase 3 activation in BCWM.1 and MWCL.1 cells treated with everolimus (0.1-10 nM) for 24 hours. Caspase-3 activation was tested using caspase-glo assay.
Figure 11:
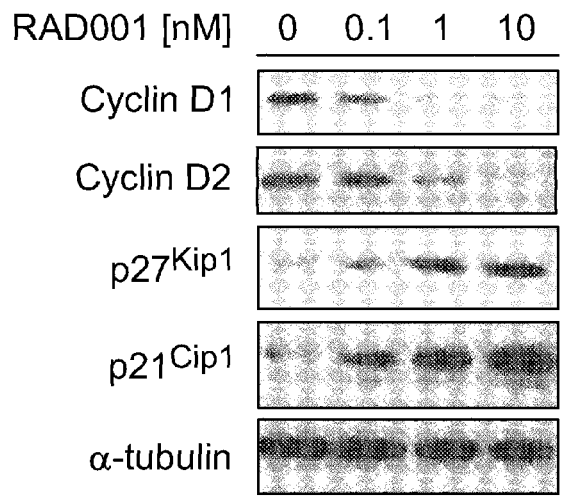
Figure 11:
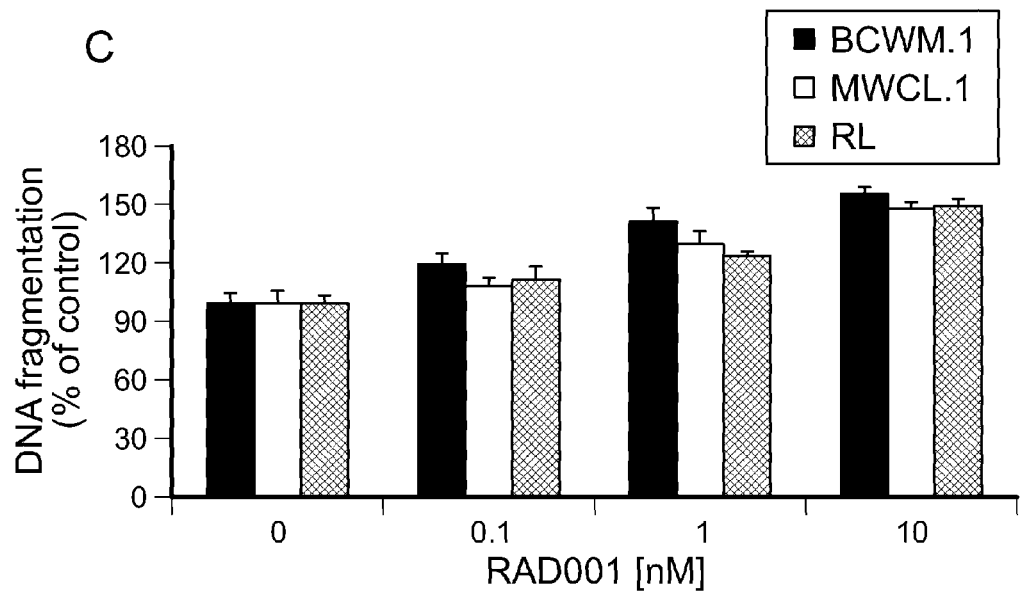
Figure 11:
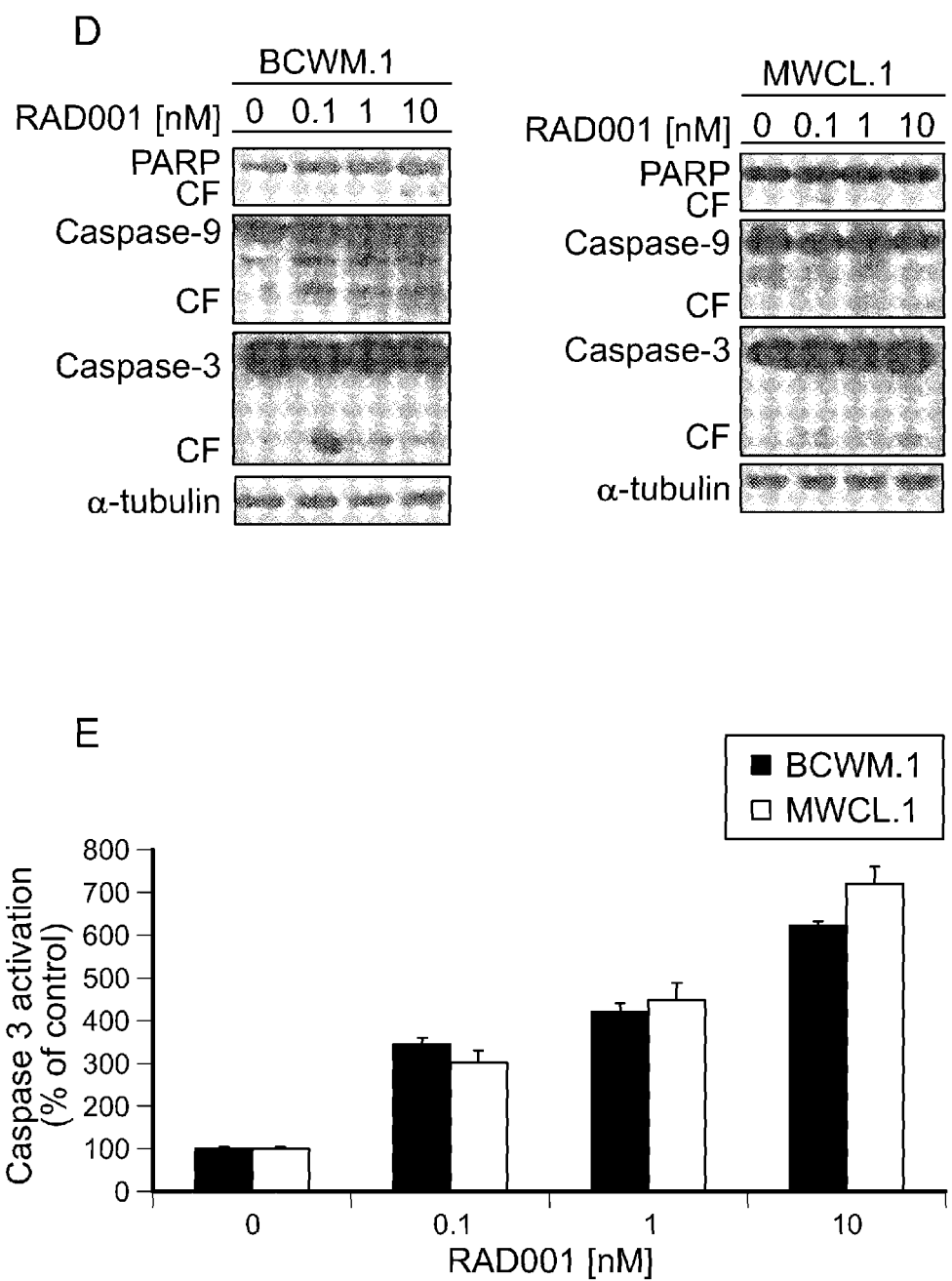

Next, it was sought to determine the underlying mechanisms that led to everolimus-dependent anti-tumor effect in WM. The activity of everolimus in targeting WM cells was tested in primary WM $CD19^+$ cells, and WM and IgM secreting lymphoma cell lines (BCWM1; MWCL.1; RL), as well as in normal PBMC-derived $CD19^+$ cells. The cytotoxic effect of everolimus (0.1-10 nM) was evaluated on primary WM bone-marrow derived $CD19^+$ cells, isolated from 4 patients with relapsed/refractory WM and it was found that everolimus significantly induced toxicity in all the 4 samples evaluated (FIG. 10A; P<0.05). Everolimus-induced toxicity in WM and IgM secreting lymphoma cell lines was subsequently validated. Everolimus targeted WM cells by inhibiting cell proliferation and by inducing cytotoxicity in a dose-dependent manner (FIG. 10B), supported by inhibition of phospo(p)-mTOR, and mTOR-down-stream targeted proteins, such as p-p70S6K and p-4EBP1 (FIG. 10C). Similarly, everolimus-dependent induction of cytotoxicity was validated on IgM low-grade lymphoma cells (FIG. 10D) Importantly, everolimus did not show cytotoxicity on primary peripheral blood-derived $CD19^+$ cells isolated from healthy individuals (FIG. 10E).

mTOR regulates cell cycle progression (Azab A. K. et al., *Blood,* 119(24):5782-94 (2012)); thus, the effect of everolimus in modulating WM cell cycle progression was examined and it was found that everolimus-treated cells presented with cell cycle arrest. Specifically, everolimus increased $G_1$ phase population in BCWM.1 cells: $G_1$ phase BCWM.1 cells increased from 52.52% in control to 61.25% and 70.98% after treatment with 0.1 nM and 1 nM everolimus, respectively. Also, inhibition of the S phase was observed, as indicated by reduction of cells in S phase from 36.29% in control to 29.14% and 21.71% after treatment with 0.1 nM and 1 nM everolimus (FIG. 11A). To determine the mechanism of everolimus-induced cell cycle arrest, the effect of the compound on WM cells was investigated using immunoblotting, and it was found that everolimus induced up-regulation of cyclin kinase inhibitor protein p27$^{Kip1}$, p21$^{Cip1}$ together with down-regulation of cyclin D1 and cyclin D2 (FIG. 11B).

It was next confirmed that everolimus also induced apoptosis in a dose-dependent manner, in WM and IgM low-grade lymphoma cells, as assessed by DNA fragmentation (FIG. 11C). The molecular mechanisms whereby everolimus induces cytotoxicity in WM cells were next examined and it was found that everolimus induced caspase-9, -3 and PARP cleavage in a dose dependent manner (FIG. 11D-11E).

Figure 12:
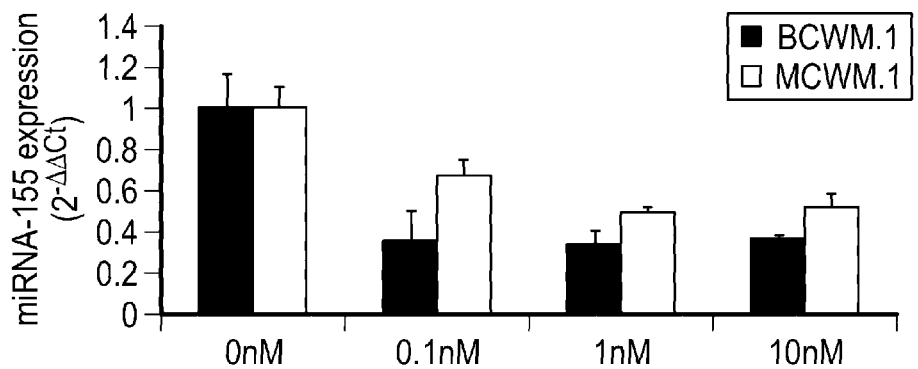
FIG. 12A is a bar graph showing miRNA-155 expression levels in WM cell lines (BCWM.1; MWCL.1) have been treated with everolimus (0.1-1-10 nM) for 12 hours. miRNA-155 expression level was evaluated by qRT-PCR, using the ΔΔCt method.
FIG. 12B is a bar graph showing survival as a percentage of control in the WM cell lines BCWM.1 (upper) and MWCL.1 (lower) transfected with either miRNA-155 knockdown probe or scramble probe, and exposed to everolimus (0.1-1-10 nM) for 48 hours. Cytotoxicity was assessed by the MTT assay.
FIG. 12C is a photograph of Western blots using anti-SHIP, -phospho(p)-Akt, -p-mTOR and -actin antibodies on whole cell lysates from BCWM.1 cells transfected with either scramble probe or anti-miRNA-155 probe and harvested at 8 hours after transfection.
FIG. 12D is a bar graph showing expression levels of miR-155 in miRNA-155 knockdown probe- and scramble probe-transfected WM cell lines (BCWM.1 and MWCL.1) 48 hours after transfection. miRNA-155 expression level was evaluated by qRT-PCR, using the ΔΔCt method.
Figure 12:
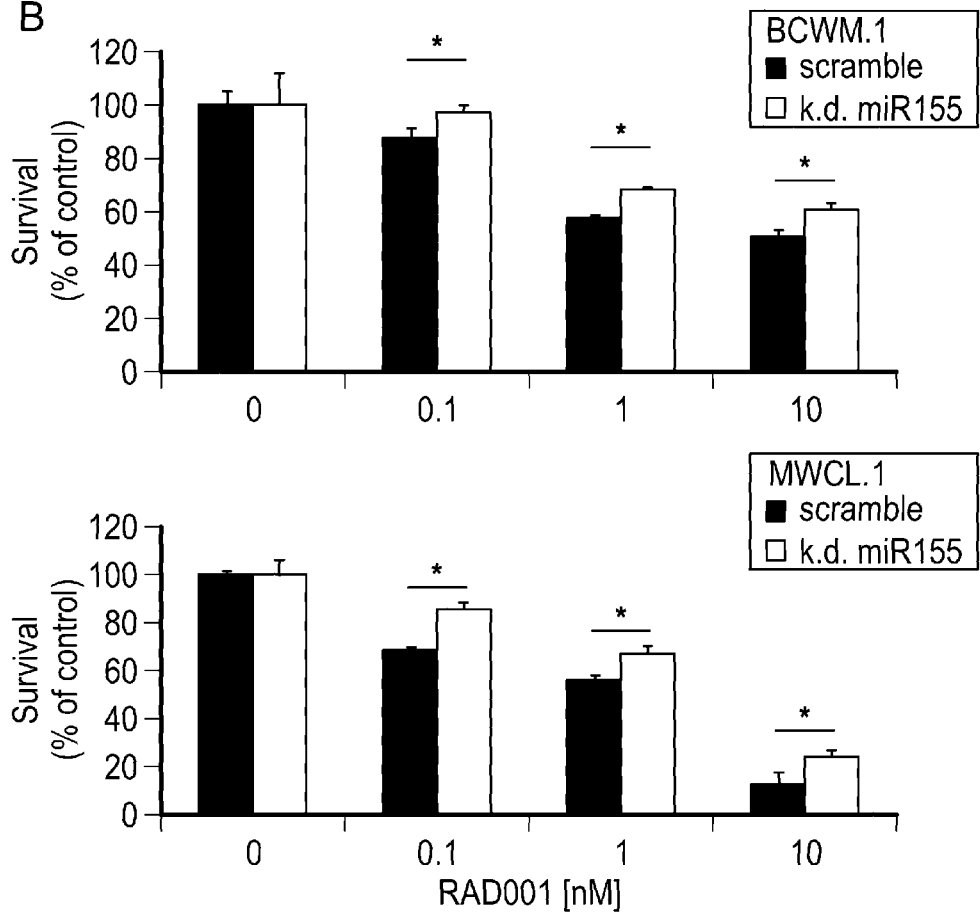
Figure 12:
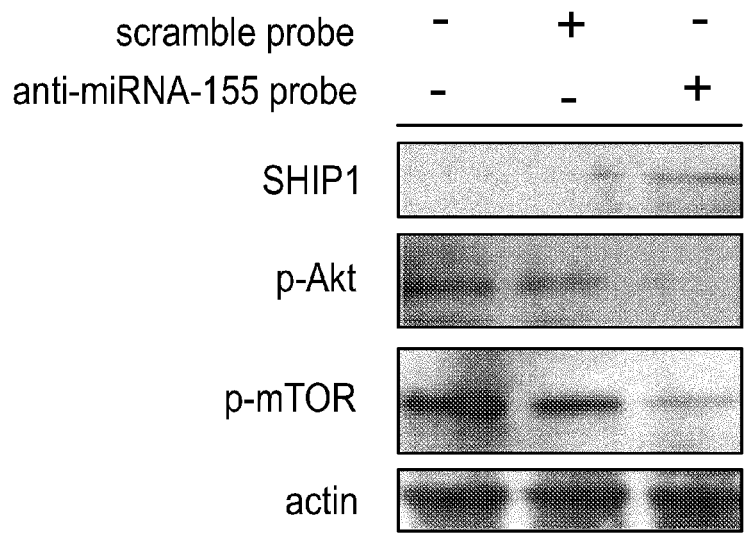
Figure 12:
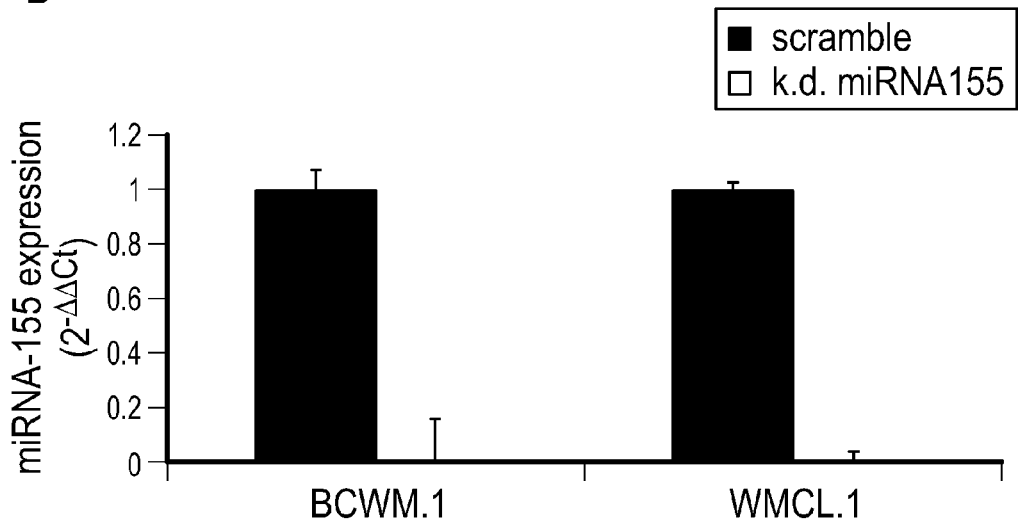

Primary WM cells show increased expression of microRNA (miRNA)-155 compared to the normal cellular counterpart (Roccaro A. M. et al., *Blood*, 113(18):4391-402 (2009)); and miRNA155 targets SHIP1 which acts as negative regulator of the PI3/Akt and mTOR pathway (Pedersen I. M. et al., *EMBO Mol. Med.*, 1(5):288-95 (2009)). It was hypothesized that everolimus-dependent anti-WM activity may be related, at least in part, to its ability to target miRNA-155 in tumor cells. Thus, it was sought to determine whether everolimus-dependent mTOR inhibition could be related to miRNA-155 expression level in WM cells. It was found that everolimus inhibited miRNA155 level in a dose-dependent manner (FIG. 12A). miRNA155-loss of function leads to inhibition of WM cell proliferation, without inducing WM cytotoxicity (Roccaro A. M. et al., *Blood*, 113(18): 4391-402 (2009)). Thus, miRNA155-loss of function studies were performed and it was found that everolimus-dependent induction of toxicity in WM cells was partially inhibited by knocking down miRNA155 (FIG. 12B). Importantly, the effect of miRNA155 knock down on its direct target SHIP has been demonstrated on anti-miRNA155-transfected cells (FIG. 12C). miRNA155 silencing in WM cells has been validated by qRT-PCR (FIG. 12D). These findings indicate that everolimus exerts anti-WM activity, at least in part, by targeting miRNA155 in WM cells.

Figure 13:
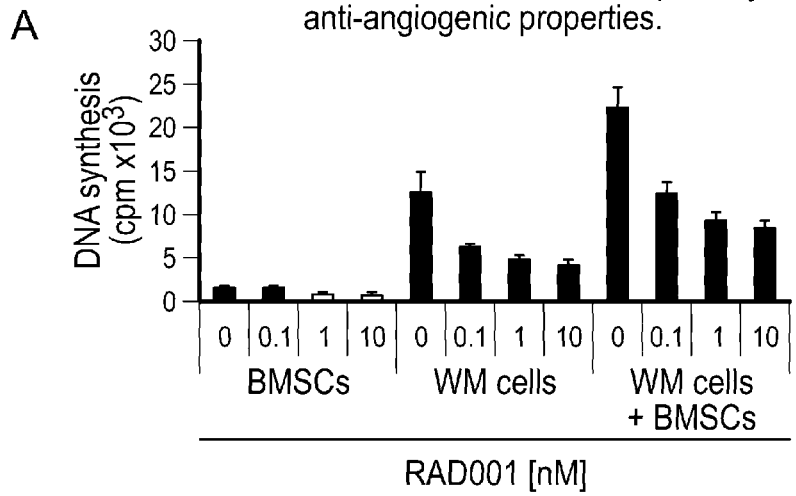
FIG. 13A is a bar graph showing DNA synthesis (to assess cell proliferation) of BCWM.1 cells cultured with control media and with everolimus (0.1-10 nM), for 48 hours, in the presence or absence of primary WM bone marrow stromal cells (BMSCs). Cell proliferation was assessed using [$^3$H]-thymidine uptake assay. All data represent mean (±sd) of triplicate experiments.
FIG. 13B is a bar graph showing the percentage of migrated BCWM.1, MWCL.1 and RL cells in the presence of everolimus (0.01-1 nM) in a transwell migration assay as compared with control with no SDF-1. SDF-1 (30 nM) was placed in the lower chambers to induce migration and migration was determined after 3 h. Everolimus inhibited SDF-1-induced migration in WM cells (P<0.05). Bars represent standard deviation.
FIG. 13C is a bar graph showing the percentage of adherent cells in an adhesion assay with BCWM.1, MWCL.1 and RL in the presence or absence of everolimus (0.01-1 nM). All data represent mean (±SD) of triplicate experiments.
FIG. 13D is a bar graph showing DNA synthesis (to assess cell proliferation) of BCWM.1 cells cultured with control media and with everolimus (0.01-10 nM), for 48 hours, in the presence or absence of endothelial cells (HUVECs). Cell proliferation was assessed using [3H]-thymidine uptake assay. All data represent mean (±sd) of triplicate experiments.
FIG. 13E is a photograph of Western blots using anti-phospo(p)-Akt, -AKT, p-GSK3, -pS6R, -p-ERK, -ERK, p-STAT3, -p-70S6K, and -actin antibodies on whole cell lysates isolated from BCWM.1 cells cultured in presence or absence of endothelial cells (HUVECs), for 8h and 24h.
FIG. 13F is a series of photographs showing HUVECs treated with everolimus (0.01-10 nM) for 4 hours and assessed for in vitro vascularization with the use of matrigel capillary-like tube structure formation assays. Quantification of number of junctions was obtained by using Image J software. In the absence of everolimus, MMECs arranged in branching tubes forming a closely knit capillary-like plexus; at increasing concentrations of drug, tube formation was blocked with almost complete inhibition of capillary formation at 1 nM of everolimus treatment.
FIG. 13G is a photograph of Western blots using anti-phospo(p)-4EBP1, -p-70S6K, and -α tubulin antibodies on whole cell lysates isolated from BCWM.1 cells cultured in presence or absence of HUVECs, and exposed or not exposed to increasing concentration of everolimus (0.01-10 nM) for 6 hours.
Figure 13:
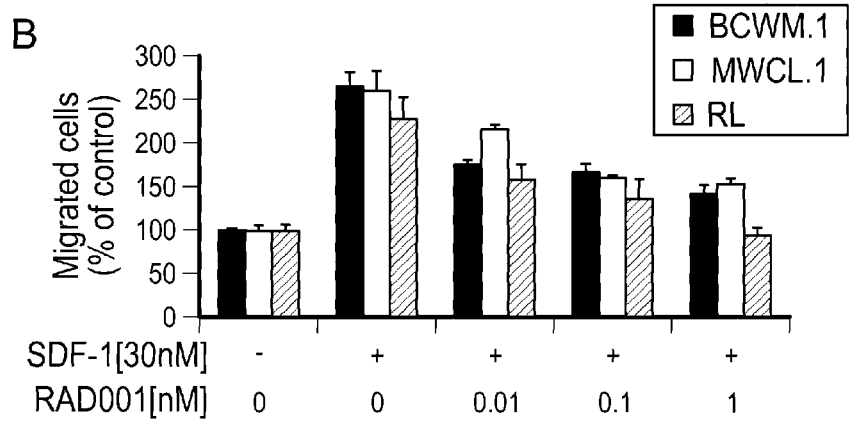
Figure 13:
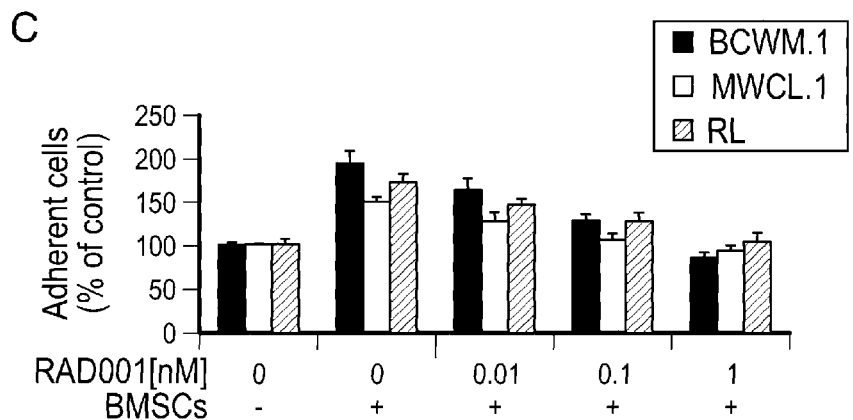
Figure 13:
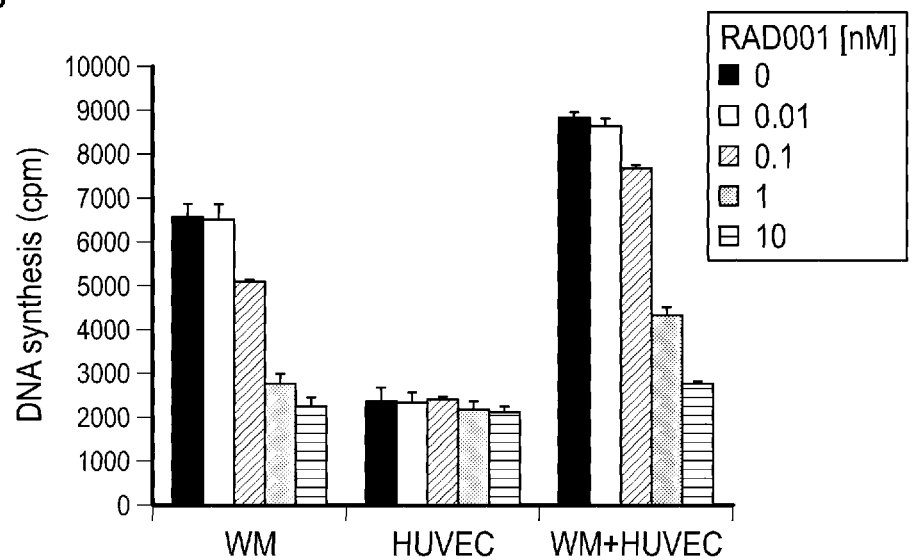
Figure 13:
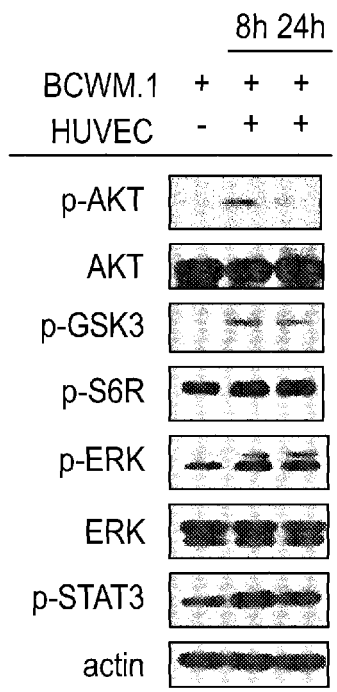
Figure 13:
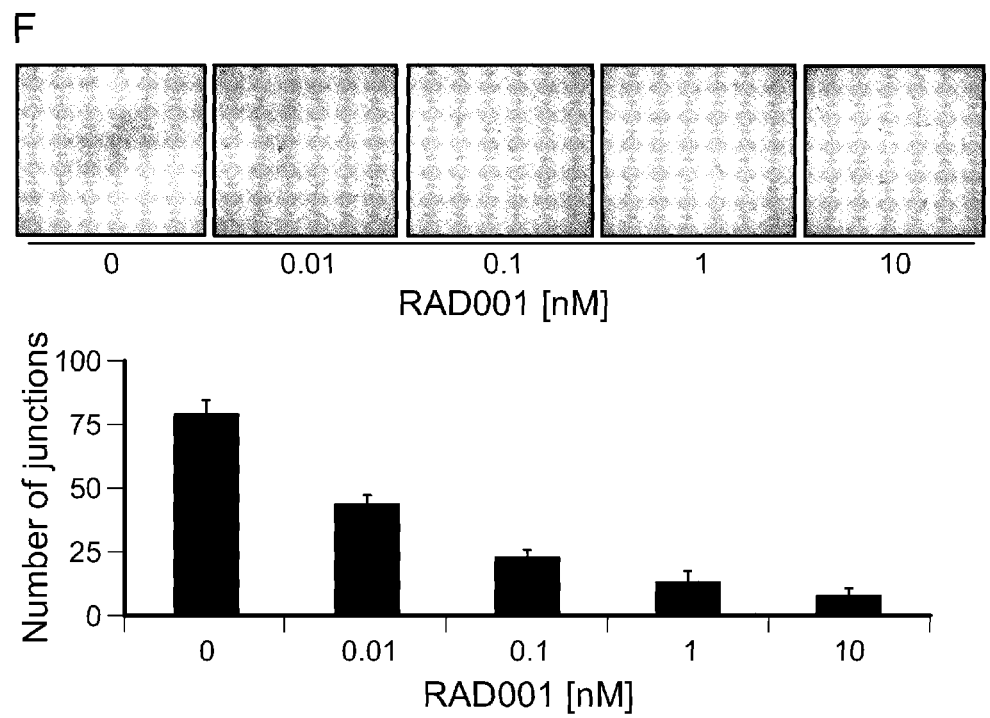
Figure 13:
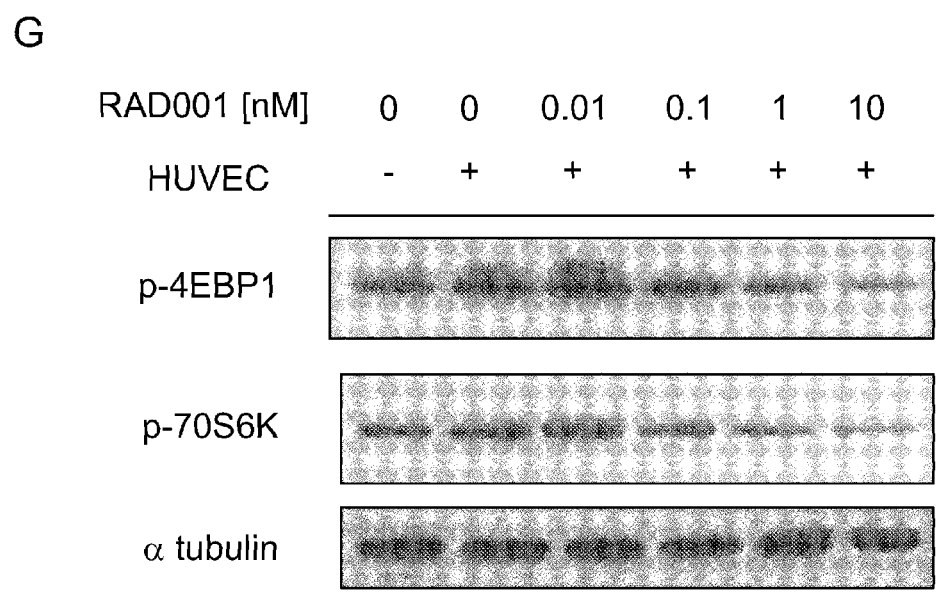

Example 12. Everolimus Targets WM Cells in the Context of Bone Marrow Microenvironment The bone marrow (BM) microenvironment confers growth and induces drug resistance in malignant cells (Mitsiades C. S. et al., *Eur. J. Cancer.*, 42(11):1564-73 (2006)). It was therefore sought to determine the anti-tumor activity of everolimus in the presence of the BM microenvironment. It was first investigated whether everolimus inhibits WM cell growth in the context of the BM milieu. BCWM.1 cells were exposed to everolimus (0.1-10 nM) in the presence or absence of BMSCs for 48 hours. The viability of BMSCs assessed by MTT was not affected by everolimus treatment (data not shown). Using [$^3$H]-TdR uptake assay, adherence of BCWM.1 cells to BMSCs triggered a significant increase in proliferation, which was inhibited by everolimus in a dose-dependent manner (FIG. 13A). Next, the efficacy of everolimus in affecting migration and adhesion of WM cells was evaluated. It was demonstrated that stromal derived factor-1 (SDF-1) induced migration in WM cells at 30 nM SDF-1. To study the effect of everolimus on the migration of WM cells, BCWM.1 cells were incubated with everolimus (0.01-1 nM) for 4 hours. These doses and duration of incubation did not induce cytotoxicity in WM cells as confirmed by MTT (data not shown). Cells were then subjected to migration as previously reported (Roccaro A. M. et al., *Blood*, 113(26):6669-80 (2009)). We found that everolimus inhibited WM cell migration towards SDF-1, in a dose-dependent manner Similar findings were also confirmed with IgM low grade lymphoma cells (FIG. 13B; P<0.05). The effect of everolimus on the adhesion of WM and IgM low grade lymphoma cell lines to primary WM bone marrow stromal cells was next tested and it was found that everolimus inhibited WM cell adhesion in a dose-dependent manner (FIG. 13C; P<0.05).

Neo-angiogenesis supports the pathogenesis of B-cell malignancies, including multiple myeloma and WM (A. Vacca et al., *Leukemia*, 20(2):193-9 (2006)). The role of endothelial cells in supporting WM cells growth was investigated and found that endothelial cells increase the proliferative rate of WM cells by 32% (FIG. 13D), supported by up-regulation of pro-survival signaling pathways, in WM cells exposed to endothelial cells, such as such as p-Akt, p-GSK3, -pS6R, p-ERK and p-STAT3 (FIG. 13E). The efficacy of everolimus in targeting WM cells was evaluated in the presence of endothelial cells and demonstrated that everolimus reduced WM cell proliferation, despite the presence of endothelial cells (FIG. 13D). It was next sought to determine the effect of everolimus on modulating vessel formation. To examine the anti-vascular activity of everolimus, capillary tubule formation assays were performed with the use of HUVECs and it was found that everolimus inhibited endothelial cell morphogenesis on Matrigel in a dose-dependent manner. In the absence of everolimus, MMECs arranged in branching tubes forming a closely knit capillary-like plexus; at increasing concentrations of drug, tube formation was blocked with almost complete inhibition of capillary formation at 1 nM of everolimus treatment (FIG. 13F). The impact of everolimus to target WM cells in presence of endothelial cells was next evaluated at signaling level. Everolimus inhibited endothelial cell-dependent phosphorylation of 4EBP1 and 70SK, in WM cells, in a dose-dependent manner (FIG. 13G).

Taken together these findings indicate the efficacy of everolimus in targeting WM cells, even in the context of bone marrow milieu where it overcomes BMSC-dependent proliferation, as well as adhesion and migration in vitro.

Example 13. Everolimus Acts Synergistically with Bortezomib and Rituximab in Targeting WM Cells The lack of complete responses (CRs) with everolimus in patients with relapsed or relapsed/refractory WM suggests that some of the lymphoplasmacytic cells might be resistant to mTOR inhibition, and this led to the hypothesis that the use of everolimus in combination with other therapeutic agents could be beneficial in patients with WM (Ghobrial I. M. et al., *J. Clin. Oncol.*, 28(8):1408-14 (2010)).

Figure 14:
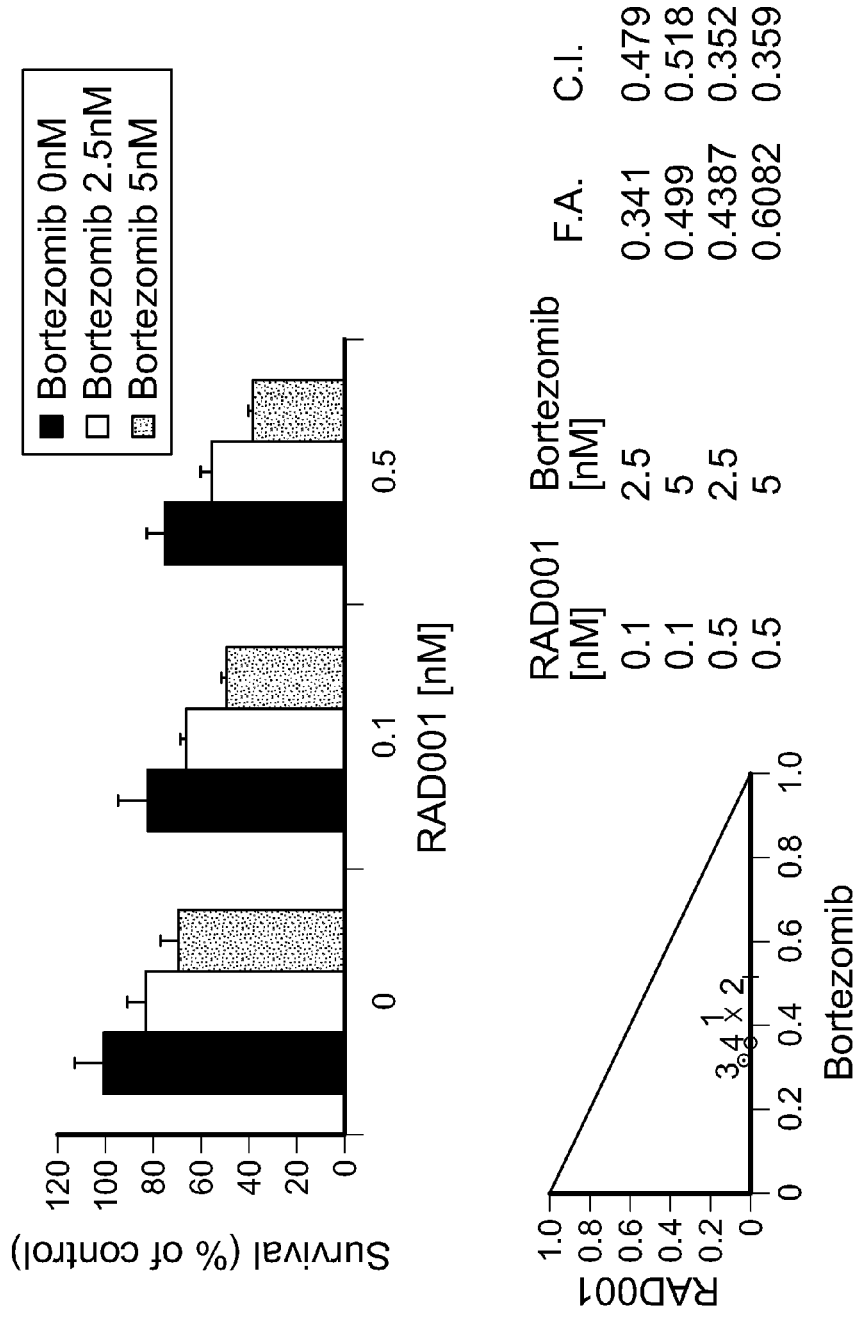
FIG. 14A is a bar graph showing percent survival after BCWM.1 cells were treated with everolimus (0.1-1 nM) in presence or absence of bortezomib (5-10 nM) for 48 hours. Cell survival was assessed by MTT assay. Below the bar graph combination indices (C.I.) and fractions affected (FA) of the combination of everolimus and Bortezomib are shown. All experiments were repeated in triplicate
FIG. 14B is a bar graph showing NF-κB p65 transcription factor binding to its consensus sequence on the plate-bound oligonucleotide was studied from nuclear extracts from BCWM.1 and MWCL.1 cells cultured with either everolimus (1 nM), bortezomib (5 nM), or the combination for 4 hours, and TNF-α (10 ng/mL) added for the last 20 minutes. Wild-type and mutant are wild-type and mutated consensus competitor oligonucleotides, respectively. All results represent means (±SD) of triplicate experiments.
FIG. 14C is a bar graph showing NF-κBp 50 transcription factor binding to its consensus sequence on the plate-bound oligonucleotide was studied from nuclear extracts from BCWM.1 and MWCL.1 cells cultured with either everolimus (1 nM), bortezomib (5 nM), or the combination for 4 hours, and TNF-α (10 ng/mL) added for the last 20 minutes. Wild-type and mutant are wild-type and mutated consensus competitor oligonucleotides, respectively. All results represent means (±SD) of triplicate experiments.
FIG. 14D is a photograph of Western blots using anti-p-NF-κBp65, -NF-κBp50, -nucleolin, -p-IkB, and -actin antibodies on cytoplasmic and nuclear extracts of BCWM.1 cells cultured with either everolimus (1 nM), bortezomib (5 nM), or the combination for 4 hours, and TNF-α (10 ng/mL) added for the last 20 minutes.
FIG. 14E is a series of photographs of immunohistochemical analysis using anti-pospho-NF-κBp65 antibody on BCWM.1 cells cultured with everolimus (1 nM), bortezomib (5 nM), or the combination for 4 hours, and TNF-α (10 ng/mL) added for the last 20 minutes. DAPI was used to stain nuclei. Phospho-p65 translocation from the cytoplasmic compartment to the nucleus was inhibited by the combination of everolimus and bortezomib, resulting in a significant increase in p-p65 expression in the cytoplasmic compartment as shown by immunofluorescence.
FIG. 14F is a bar graph showing mean percentage lysis upon antigen dependent cellular cytotoxicity (ADCC) of BCWM.1 cells treated with everolimus (1 nM), bortezomib (5 nM), rituximab (10 μg/mL), and the combination, in absence and presence of activated effector cells. Results are reported in terms of mean percentage of specific lysis characterized by measurement of release of calcein-AM upon different effector-target ratios (E/T ratio). The following controls showed minimum released of calcein-AM and were not added to the figure: medium alone, BCWM.1 or activated effector cells alone, BCWM.1 incubated with activated effector cells in absence of rituximab, activated effector cells with rituximab in absence of target cells.
FIG. 14G is a series of photographs of immunohistochemical analysis of BCWM.1 cells cultured with everolimus (1 nM), bortezomib (5 nM), rituximab (10 μg/mL), or the triple combination for 4 hours, and TNF-α (10 ng/mL) added for the last 20 minutes. The data show that the everolimus+rituximab+bortezomib combination led to significant inhibition of phosphorylation of S6R, mTOR-downstream targeted protein.
Figure 14:
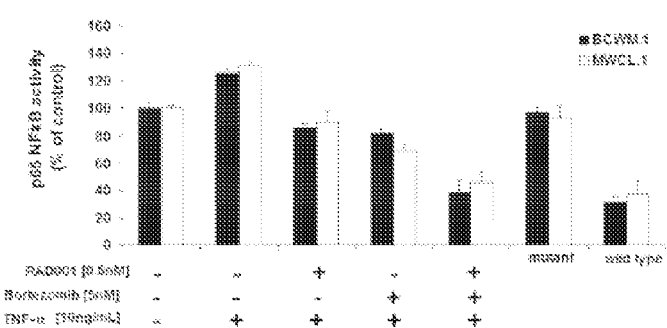
Figure 14:
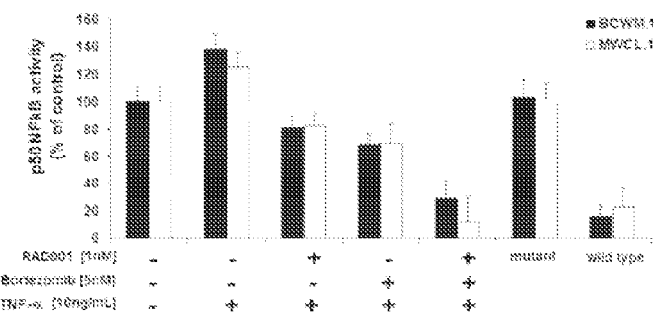
Figure 14:
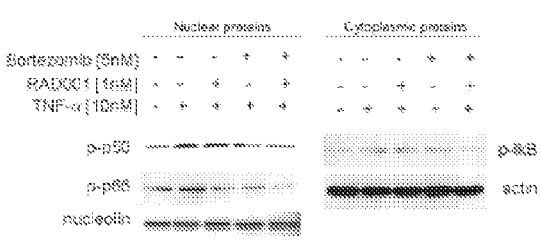
Figure 14:
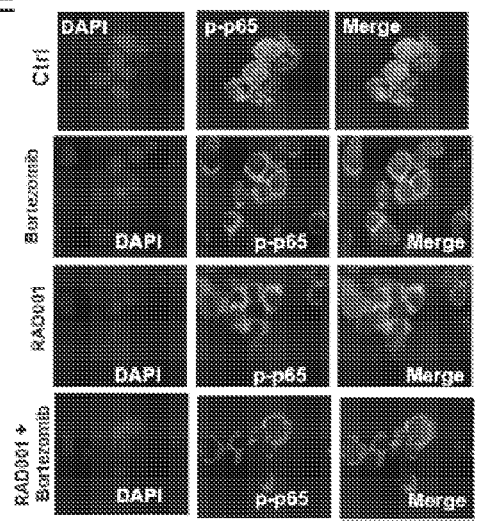
Figure 14:
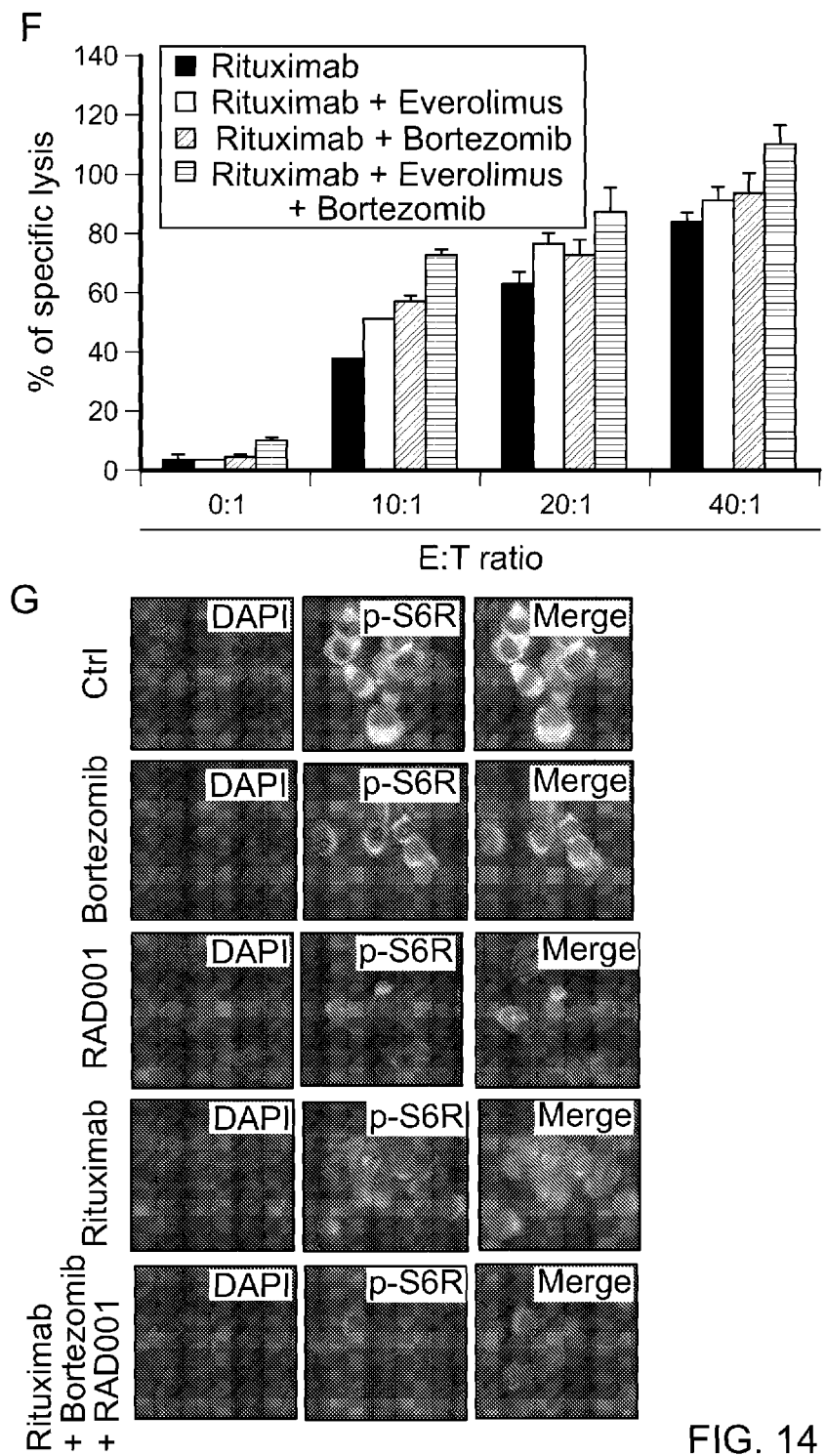

BCWM.1 cells were cultured with everolimus (0.1-0.5 nM) for 48 hours, in the presence or absence of bortezomib (2.5-5 nM). Everolimus showed significant cytotoxic effects when combined with bortezomib, as demonstrated by using MTT assays at 48 hours (FIG. 14A). Everolimus (0.5 nM) induced cytotoxicity in 24% of BCWM.1 cells, which was increased to 43% and 60% in the presence of bortezomib at 2.5 nM (combination index, C.I.: 0.47) and 5 nM (C.I.: 0.51), respectively, indicating synergistic activity. Similar results were obtained using bortezomib with everolimus 0.1 nM. Isobologram analysis, fractions affected, and the combination indexes for each of these combinations are indicated (FIG. 14A).

Primary WM cells present with a constitutive activation of the NFkB pathway, thus resulting in increased tumor cell growth and disease progression (Leleu X. et al., *Blood*, 111(10):5068-77 (2008)). Thus, it was investigated whether everolimus-induced WM cytotoxicity may be due, at least in part, to its ability to modulate NFkB-related proteins, and whether everolimus would lead to a synergistic inhibition of this pathway when used with bortezomib in a combinatory regimen. The effect of everolimus, either alone or in combination with bortezomib, was evaluated on the NF-κB p65 and NF-κB p50 binding activities, studying nuclear extracts from treated cells using the Active Motif assay. It was found that TNF-α treatment induced NF-κB recruitment to the nucleus in BCWM.1 and MWCL.1 cells, which was similarly inhibited by either everolimus or bortezomib, used as single agents. Importantly, a significant inhibition of -NFκB p65 DNA-binding activity (84%) was documented in WM cells exposed to the combination of everolimus and bortezomib (FIG. 14B). Similar findings were observed by testing the effect of everolimus on NF-κBp65 binding activity (FIG. 14C). These findings were further corroborated at protein level, by studying nuclear protein lysates: TNF-α-dependent nuclear translocation of p-p65 and p-p50 was more significantly inhibited in WM cells exposed to the combination of everolimus and bortezomib, compared to each agent used as single drug. This was also supported by a synergistic inhibition of p-IkB at cytoplasmic level, when everolimus and bortezomib were used in a combinatory regimen (FIG. 14D). It was further confirmed that phospho-p65 translocation from the cytoplasmic compartment to the nucleus was inhibited by the combination of everolimus and bortezomib, resulting in a significant increase in p-p65 expression in the cytoplasmic compartment as shown by immunofluorescence (FIG. 14E).

The monoclonal anti-CD20 antibody represents one of the main therapeutic approaches in patients with WM. Thus, the effect of the combination of everolimus with rituximab was assessed by ADCC. A modest increase in specific lysis has been observed in WM cells exposed to Rituximab and bortezomib, compared to Rituximab used as single agent: indeed, the specific lysis increased from 37.7% with rituximab alone to 51.4% when rituximab 10 μg/mL was combined with everolimus (1 nM) with an E/T ratio of 10:1. Importantly, specific lysis increased to 73.1% when WM cells were exposed to the combination of everolimus, rituximab and bortezomib (E/T ratio of 10:1). Increased specific lysis with the combination was observed at all E/T ratios studied (FIG. 14F). These findings were also confirmed by immunofluorescence, where the everolimus+rituximab+bortezomib combination led to significant inhibition of phosphorylation of S6R, mTOR-down stream targeted protein (FIG. 14G).

Example 14: Materials and Methods for Examples 15-18 a) Cells and Patients Characteristics:

Primary BM-MSCs were obtained from both healthy subjects (ND-MSCs) and relapsed/refractory MM patients (MM-MSCs); monoclonal gammopathy of undetermined significance MGUS) patients; smoldering MM (S-MM) patients and cultured and selected in plastic flasks, and used at the $5^{th}$-$6^{th}$ passage (Garayoa M. et al., Leukemia, 23(8): 1515-1527 (2009)). According to previous reports and to the International Society for Cellular Therapy, combinations of monoclonal antibodies were used to define the growing cells as MSCs and included: anti-CD34-APC, -CD19-APC, -CD-45-PerCPCy5.5, -CD14-FITC, -CD90-FITC, -CD73-PE, -CD106-PE and -CD105-FITC (Dominici et al., Cytotherapy, 8(4):315-317 (2006)). Appropriate isotopic controls were used. MM cell lines (MM.1S; RPMI.8226) and stromal cell line (HS-5) were purchased from ATCC® (Manassas, Va.) and used for in vitro studies. The luciferase (luc)-expressing MM.1S-GFP/luc cell lines were generated by retroviral transduction with the pGC-gfp/luc vector (kind gift of Dr. A. Kung, Dana-Farber Cancer Institute, Boston, Mass.). Both patients and healthy individuals presented with median age of 69 and 66.5, ranging from 60 to 72 years and 64 to 73 years, respectively. Patients were diagnosed with either MM, MGUS, or S-MM based on the International Myeloma Working Group criteria (International Myeloma Working Group, Criteria for the classification of monoclonal gammopathies, multiple myeloma and related disorders: a report of the International Myeloma Working Group, Br. J. Haematol., 121(5):749-57 (2003)). All of the patients studied had multiple myeloma at an active stage, with either relapsed disease, or disease refractory to previous treatment. Thus, all the patients were homogenous in their population, since all of them were with active MM, with relapsed-refractory disease.

b) Exosome Purification and Fluorescent Labeling:

Exosomes were purified from cell culture supernatant of BM-MSCs. Fetal bovine serum (FBS) used in culture media for exosome isolation was pre-cleared by ultracentrifugation at 100,000×g for 3 hr at 4° C. Supernatant fractions collected from 48 hours BM-MSC cultures were filtered using a filtration on 0.22 μm pore filters, as previously described (Valadi et al., *Nat. Cell. Biol.*, 9(6):654-659 (2007), Ostrowski M. et al., *Nat. Cell Biol.*, 12(1):19-30 (2010)), followed by ultracentrifugation at 20,000g for 20 min, and incubation with an exosome precipitation solution (ExoQuick, System Biosciences, Mountain View, Calif.) (Karolina D. S. et al., *PLoS One*, 6(8): e22839 (2011)). Exosomes were then harvested by ultracentrifugation at 100,000g for 70 min, as previously described (Peinado H. et al., *Nat. Med.*, 18(6):883-91 (2012)). Isolation of exosomes was also obtained following the same procedure as described above, without including the ExoQuick incubation step, as previously described (Valadi et al., *Nat. Cell. Biol.*, 9(6):654-659 (2007), Ostrowski M. et al., *Nat. Cell Biol.*, 12(1):19-30 (2010), Peinado H. et al., *Nat. Med.*, 18(6):883-91 (2012)). For functional assays where exosomes were used, the concentration of total proteins contained in each exosome pellet has been quantified by Bradford assay (BioRad), as described (Théry C. et al., *J. Cell. Biol.*, 147(3):599-610 (1999), Ostrowski M. et al., *Nat. Cell Biol.*, 12(1):19-30 (2010)): exosomes have therefore been quantified as μg of containing proteins. Exosomes were labeled with the green fluorescent linker PKH67 (Sigma-Aldrish, St. Louis, Mo.), as described (35). Exosomes isolated using the two different procedures (with and without ExoQuick solution) showed similar results, at the ultrastructural level (electron microscopy/immunogold labeling).

c) Electron Microscopy:

Exosomes were adsorbed for 1 minute to a carbon-coated grid that had been made hydrophilic by a 30 second exposure to a glow discharge. Excess liquid was removed with a filterpaper (Whatman #1), and the samples were stained with 1 Uranyl Acetate for 30 seconds. After removing the excess uranyl formate with a filter paper, the grids were examined in a TecnaiG² Spirit BioTWIN and images were recorded with an AMT 2k CCD camera. For immunogold labeling, pelleted exosomes were fixed with 2% paraformaldehyde in 0.1M phosphate buffer at pH7.4, and then processed for ultrathin sectioning and immunogold labeling using anti-CD63 and anti-CD81 antibodies and protein A coupled with 10- or 15-nm gold particles as described (Valadi et al., *Nat. Cell. Biol.*, 9(6):654-659 (2007), Ostrowski M. et al., *Nat. Cell Biol.*, 12(1):19-30 (2010)). Sections were observed at 80 kV with a TecnaiG$^2$ Spirit BioTWIN Transmission electron microscope (FEI, the Netherlands), and images were recorded with an AMT 2k CCD camera.

d) Immunoblotting:

Exosomes were lysed using lysis buffer (Cell Signaling Technology, Beverly, Mass.) reconstituted with 5 mM NaF, 2 mM Na$_3$VO$_4$, 1 mM PMSF (polymethilsulfonyl fluoride), 5 µg/mL leupeptine, and 5 µg/mL aprotinin. Whole-exosomal lysates (100 µg/lane) were subjected to sodium dodecyl sulfate-polyacrylamide gel eletrophoresis (SDS-PAGE) and transferred to polyvinyldene fluoride (PVDF) membrane (Bio-Rad Laboratories, Hercules, Calif.). Anti-CD63, -CD81, -p-cofilin, -fibronectin, -junction plakoglobin (γ-catenin), -CXCL2 (MCP1), -tubulin and -actin antibodies were used.

e) ELISA:

IL-6 levels were measured using an IL-6 ELISA (Human IL-6 immunoassay, R&D Systems, Minneapolis, Minn.), according to manufacturer's protocol. Anti-IL-6 neutralizing antibody and the related isotype control were purchased from R&D Systems (Minneapolis, Minn.).

f) Isolation of Exosomal RNA and miRNA Profiling:

RNA was isolated using RNeasy mini kit (Qiagen, Valencia, Calif.), according to manufacturer's protocol and as previously described (Valadi et al., *Nat. Cell. Biol.*, 9(6): 654-659 (2007)). miRNA profiling was assessed by using TaqMan human miRNA profiling. *C. elegans* miRNA-39 was chosen as internal spiked control because of a lack of sequence homology to human miRNAs and absence of empiric hybridization to human miRNA probes on miRNA microarrays, as previously described (Kroh E. M. et al., *Methods*, 50(4):298-301 (2010)). Mean miRNA expression value has been used for miRNA RT-qPCR data normalization, as described (Mestdagh P. et al., *Genome Biol.*, 10(6): R64 (2009)). Comparison between normal (n=4), and MM- (n=7), MGUS (n=2) BM-MSCs-derived exosomes was performed using dChip software (1.5 fold change; P<0.05).

g) Quantitative Reverse Transcription-PCR (qRT-PCR):

qRT-PCR for miRNAs of interest (TaqMan microRNA Assays, Applied Biosystems, Foster City, Calif.) was performed on an *Applied Biosystems AB*7500 Real Time PCR system. All PCR reactions were run in triplicate and miRNA expression, relative to RNU6B or *C. Elegans* miRNA39, was calculated using the $2^{-\Delta\Delta Ct}$ method (Livak K. J. et al., *Methods*, 25(4):402-408 (2001)).

h) miRNA Transfection:

HS-5 and normal primary normal BM-MSCs were transfected with either precursor (pre)-, anti-miRNA-15a or scramble probe, used as control (Exiqon, Vedbaek, Denmark), at final concentration of 40 nM, as previously described (Roccaro A. M. et al., *Blood*, 113(26):6669-6680 (2009)), using Lipofectamine 2000 following manufacturer's instructions (Invitrogen, Carlsbad, Calif.). Efficiency of transfection was validated by qRT-PCR for the detection of miRNA-15a levels.

i) Confocal Microscopy-Time lapse:

Exosomes and MM cells were fluorescently labeled using PKH67 and FITC conjugated anti-tubulin antibody, respectively. Cellular nuclei were stained using DAPI. Imaging of exosome uptake was performed using a Yokogawa spinning disk confocal system (Andor Technology, South Windsor, Conn.) with a 100×1.4NA Plan-Apochromatic objective on a Nikon Ti-E microscope equipped with a Hamamatsu OrcaER CCD camera. Laser illumination, shutters and filter wheel were controlled by Andor iQ software. MM.1S GFP+ cells were incubated with DiD-labeled exosomes for 30 minutes. Laser excitation of GFP and DiD was performed sequentially using the 488 nm and 640 nm lasers. Images were acquired using a 100× Plan Apo objective lens with a Hamamatsu OrcaER camera. Acquisition parameters, shutters, filter positions and focus were controlled by Andor iQ software (Andor Technology, South Windsor, Conn.).

j) In Vivo Studies:

MM cells homing to the bone marrow (BM) were imaged in vivo using a Zeiss 710 confocal system (Carl Zeiss Microimaging, Jena, Germany) on an upright Examiner stand with a custom stage. A skin flap was made in the scalp of the mice to expose the underlying dorsal skull surface. Images of the tumors were captured in approximately 1 hour-long sessions. High-resolution images with cellular detail were obtained through the intact mouse skull at depths of up to 250 µm from the surface of the skull using a 10×0.45NA Plan-Apo objective (Carl Zeiss Microimaging). Multiple imaging depths were acquired, and a maximum intensity z-projection was performed in Image J to merge the images. GFP was excited with the 488 nm line on an Argon laser. Blood vessels were imaged using Evans Blue (Sigma-Aldrich, St. Louis, Mo.) excited with a 633 nm laser. Emission signals were collected by using the Zeiss internal confocal Quasar detectors. In vivo tumor growth has been assessed by using in vivo bioluminescence imaging. Mice were injected with 75 mg/kg of Luciferin (Xenogen, Hopkington, Mass.), and tumor growth was detected by bioluminescence, using Xenogen In Vivo Imaging System (Caliper Life Sciences, Hopkinton, Mass.). Five weeks old female SCID-beige mice were obtained from Charles River Labs (Wilmington, Mass.). C57BL/6 miRNA-15a/16-1$^{-/-}$ were a kind gift of Dr. R. Dalla Favera (Columbia University, New York, N.Y.). All mice (C.B-17/Icr/Crl-scid/bgBR; C57BL/6 BL; C57BL/6 miRNA-15a-/-) were treated, monitored, and sacrificed in accordance with approved protocol of the Dana-Farber Cancer Institute Animal Care and Use Committee.

k) Tissue Engineered Bones:

Silk scaffolds were created and differentiated into tissue-engineered bone (TEB) as previously reported (Goldstein R. H. et al., *Cancer Res.*, 70(24):10044-10050 (2010)). TEBs were loaded with MM cells (3×10$^6$ cells) alone or in presence of normal or MM BM-MSC-derived exosomes (1 µg). MM cells were previously cultured in the presence or absence of exosomes for 48 hours and subsequently implanted s.c. Exosomes (1 µg) were injected in situ, every four days, until the end of the studies. TEB scaffold loaded with MM cells and materials recovered after Exoquick precipitation of medium that had not been conditioned by any cells were used as control in vivo.

l) In Vitro Studies:

DNA synthesis was measured by [$^3$H]-thymidine ([$^3$H]-TdR; Perkin Elmer, Boston, Mass.) uptake, as previously described (Roccaro A. M., et al., *Blood*, 113(26):6669-6680 (2009)). Adhesion was evaluated by using an in vitro adhesion assay to fibronectin, following the manufacturer's recommendations (EMD Biosciences, San Diego, Calif.). Calcein AM was used to measure adherent cells, and the degree of fluorescence was measured using a spectrophotometer (485-520). BSA-coated wells served as a negative control. 48 hour co-cultures of MM cells (MM.1S; RPMI.8226) with primary normal BM-MSCs or HS-5 were performed, and MM cell proliferation rate was evaluated by [$^3$H]-TdR uptake, as previously described (Roccaro A. M., et al., *Blood,* 113(26):6669-6680 (2009)). Exosomes were tested for their functional effects at concentrations previously reported (Skog J. et al., *Nat. Cell. Biol.,* 10(12):1470-1476 (2008), Montecalvo A. et al., *J. Immunol.,* 180(5):3081-3090 (2008), Yu S. et al., *J. Immunol.,* 178(11):6867-6875 (2007)).

m) Tissue Immunofluorescence:

Tissue immunofluorescence was performed on both TEBs and femurs harvested from mice, as described (Hsieh A. C. et al., *Nature,* 485(7396):55-60 (2012)). Cells of interest were MM.1S-GFP+. Nuclear stain DAPI was added to each slide. Slides were analyzed using a fluorescence microscope (Nikon TE2000-E; objective 40× plan fluor 0.75NA). MM.1S-GFP+ cells were counted from 4 separate fields per slide. Images were taken using the Hamamatsu OrcaER camera and the NIS-Element software. Image J was used to merge the two different channels.

n) Protein Array:

Exosomal and cellular protein contents were evaluated by using antibody microarray (BD Clontech, Palo Alto, Calif.), as described (Ghobrial I. M. et al., *Blood,* 105(9):3722-3730 (2005)).

o) Statistics:

P values described in the in vitro assays are based on T-tests (two-tailed; a 0.05); or on ANOVA. Actual P values are provided for each figure. In the protein arrays, prior to analysis of the protein expression, the data were background corrected (Ritchie M. E. et al., *Bioinformatics,* 23(20):2700-2707 (2007)), normalized within array using loess normalization of the M-values and normalized across arrays using quantile normalization to the A-values (Smyth G. K., *Methods,* 31(4): 265-273 (2003)). Linear model with adjustment for correlation between duplicate spots was then applied using the FDR approach. The limma package in R was used for the analysis (Smyth, G. K. Limma: linear models for microarray data. In: *Bioinformatics and Computational Biology Solutions using R and Bioconductor,* R. Gentleman, V. Carey, S. Dudoit, R. Irizarry, W. 2005. Huber, eds. (Springer, New York), pp397-420)).

p) Accession Numbers:

miRNA expression profiling has been deposited in NCBI's Gene Expression Omnibus (series accession number: GSE39571).

Figure 15:
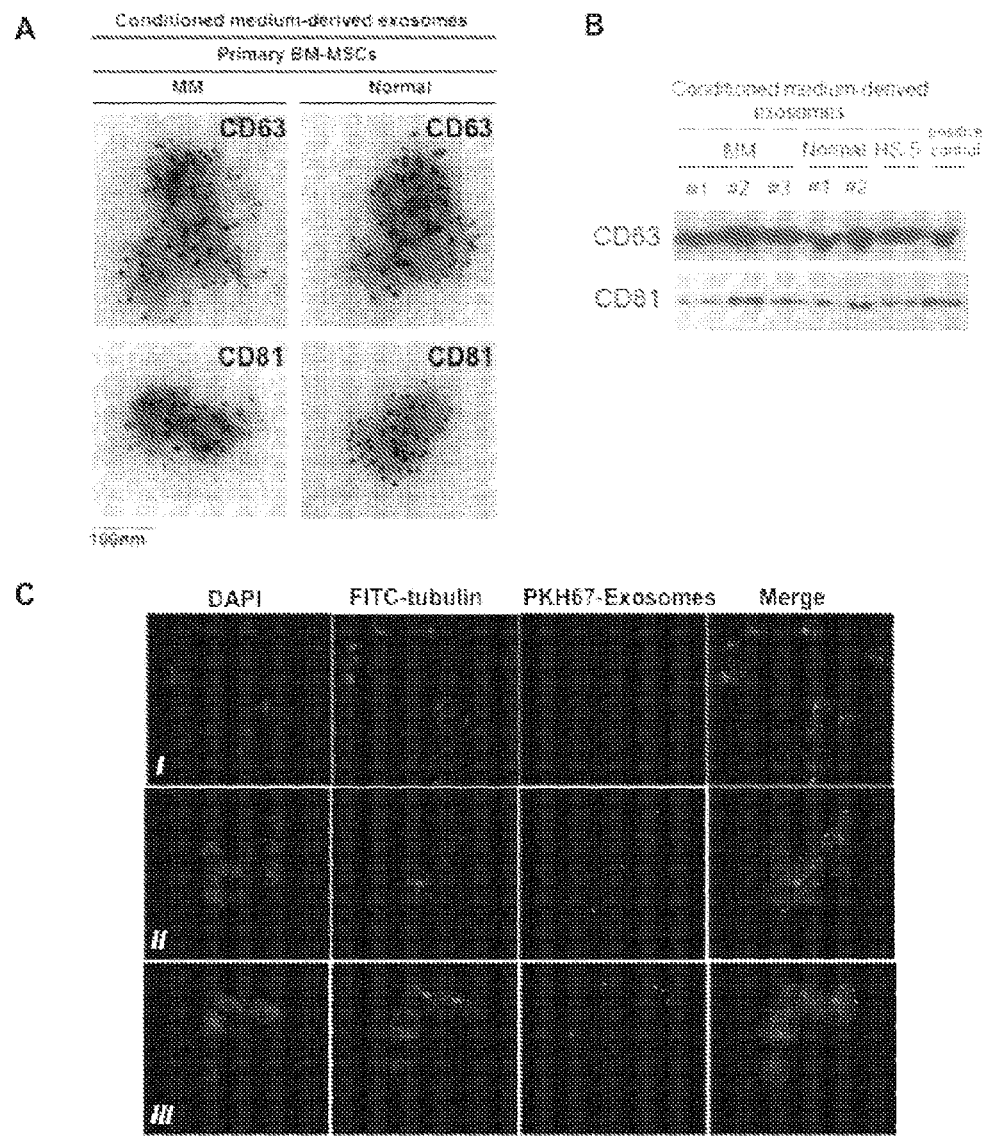
FIG. 15A is a series of photographs of bone marrow mesenchymal stromal cells (BM MSC)-derived exosomes. Exosomes were immunogold labeled with anti-CD63 and anti-CD81. The scale bar indicates 100 nm.
FIG. 15B is a photograph of Western blots using anti-CD63 and anti-CD81 antibodies on MM-(n=3) and normal-(n=2) BM-MSCs-exosomes. HS-5 normal stromal cell line has been included. Lysates obtained from either human CD63- or human CD81-transfected 293T cells served as positive controls.
FIG. 15C is a series of photographs of confocal images of MM.1S cells cultured in the absence (I), or presence of normal-(II), or MM-BM-MSCs (III)-derived PKH67-labelled exosomes, for 30 minutes. In panel (I) cells were incubated with non-containing cell media processed as in panels (II) and (III). Exosomes were taken up by MM cells, as shown by using a confocal microscope (100× objective). MM cells were stained using DAPI (nuclei) and FITC conjugated-anti-tubulin antibody.

Example 16. Bone Marrow Mesenchymal Stromal Cell-Derived Exosomes are Transferred to Multiple Myeloma Cells Exosomes were isolated from primary BM-MSC conditioned medium obtained from either patients with MM or healthy individuals, as described (Valadi et al., *Nat. Cell. Biol.,* 9(6):654-659 (2007), Ostrowski M. et al., *Nat. Cell Biol.,* 12(1):19-30 (2010); Karolina D. S. et al., PLoS One, 6(8): e22839 (2011)). The purity of BM-MSCs, evaluated as previously described (Dominici M. et al., *Cytotherapy,* 8(4): 315-317 (2006), Garayoa M. et al., *Leukemia,* 23(8):1515-1527 (2009)), was greater than 95%, showing a multipotent mesenchymal stromal cell origin. Isolated exosomes were studied by electron microscopy demonstrating rounded particles with a size of approximately 100 nm, with a membrane-like bilayer, usually observed in exosomes. The exosomal expression of CD63 and CD81, surface antigens commonly used as exosomal markers, was evaluated and confirmed by using immunogold labeling (FIG. 15A), and western blot (FIG. 15B). Similar results were obtained when the morphology and immunophenotype of exosomes isolated using the two isolation procedures adopted were compared (with or without ExoQuik solution). The CD63 and CD81 phenotype was also validated on BM-MSCs isolated from both MM and healthy subjects, as well as on BM-MSC line, HS-5.

It was next sought to examine whether BM-MSC-derived exosomes could be transferred to MM cells. PKH67-fluorescently labeled exosomes isolated from both normal and MM BM-MSCs conditioned medium were cultured with MM cells. The ability of MM cells to uptake exosomes was confirmed, as shown by confocal microscopy (FIG. 15C). These findings were validated by reading the fluorescence signal of MM cells exposed to fluorescently labeled exosomes. Further confirmation was obtained using time-lapse microscopy, showing uptake of DiD-labeled exosomes into MM.1S GFP+ cells. These results indicate that either normal or MM BM-MSCs-derived exosomes can be transferred into MM cells, suggesting their potential role in regulating MM biology.

Example 17. Functional Sequelae of Exosomes on MM Cell Proliferation and Homing to the Bone Marrow The interaction between the BM microenvironment and MM plasma cells plays a pivotal role in supporting MM pathogenesis and progression (Mitsiades C. S. et al., *Eur. J. Cancer,* 42(11):1564-1573 (2006)). The findings of exosomal transfer between BM-MSCs and MM cells support the hypothesis that exosomes actively mediate tumor growth and dissemination. Therefore, the effect of normal and MM BM-MSCs-derived exosomes on the in vitro and in vivo growth of MM cells was investigated.

Figure 16:
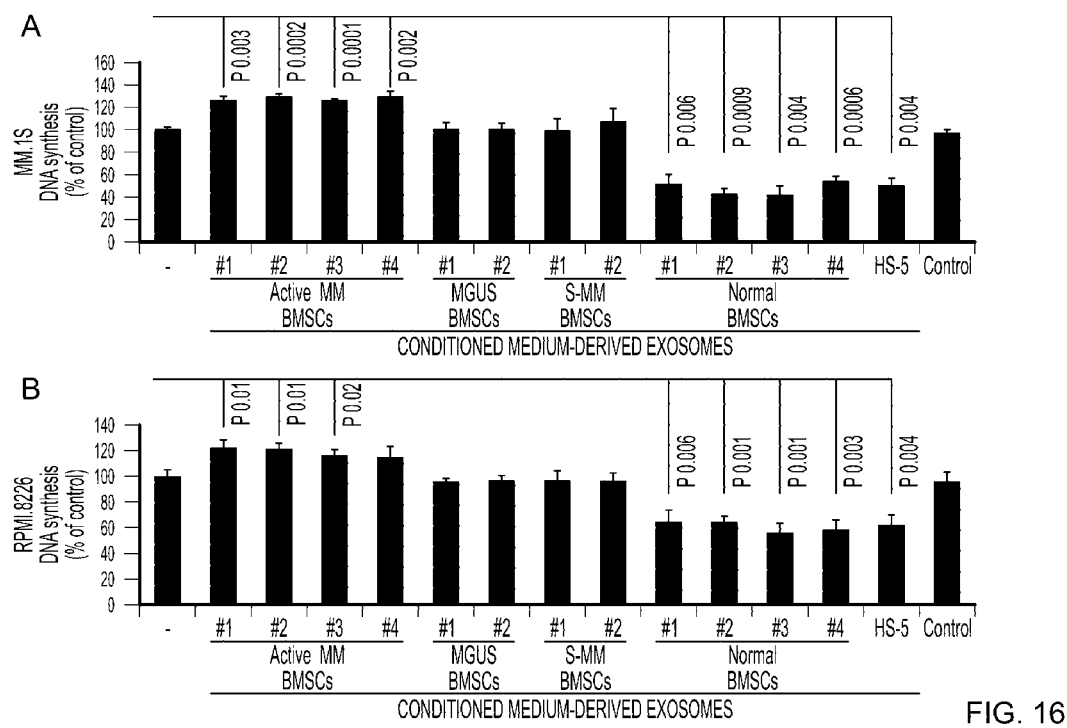
FIG. 16A is a bar graph showing that normal and MM BM-MSC-derived exosomes differentially affect MM cell proliferation in vitro. MM.1S cells (30,000 cells/well; RPMI medium 10% exosome-depleted FBS) RPMI.8226: panel b) were cultured in absence (−) or presence of MM (n=4)-, MGUS (n=2)-, smoldering (S; n=2)-, or normal (n=4)-BM-MSC-derived exosomes (200 μg/mL; 48h). Loaded exosomes are expressed as μg of protein-contained exosomes. Cell proliferation was assessed using [$^3$H]-thymidine uptake. Control indicates non-containing cell conditioned media processed as in all the samples tested. The average of three independent experiments is shown. P values were generated using ANOVA. MM- and normal-BM-MSC-derived exosomes showed a differential impact on MM cell growth in vitro.
FIG. 16B is a bar graph showing that normal and MM BM-MSC-derived exosomes differentially affect MM cell proliferation in vitro. RPMI.8226 cells (30,000 cells/well; RPMI medium 10% exosome-depleted FBS) were cultured in absence (−) or presence of MM (n=4)-, MGUS (n=2)-, smoldering (S; n=2)-, or normal (n=4)-BM-MSC-derived exosomes (200 μg/mL; 48h). Loaded exosomes are expressed as μg of protein-contained exosomes. Cell proliferation was assessed using [3H]-thymidine uptake. Control indicates non-containing cell conditioned media processed as in all the samples tested. The average of three independent experiments is shown. P values were generated using ANOVA.
FIG. 16C is a bar graph showing the ability of MM BM-MSC-derived exosomes to modulate MM cell growth in vivo using tissue-engineered bones (TEBs). Tissue-engineered bones (T.E.B.) were loaded with either MM.1S-GFP+/Luc+ cells alone or with primary MM- or normal-BM-MSC-derived exosomes ($3\times10^6$ cells/T.E.B.; 1 μg exosomes), and implanted subcutaneously in SCID mice. Exosomes (1 μg) were also injected in situ, every four days, until the end of the studies. Detection of tumor growth, as performed by measuring bioluminescence imaging (BLI) intensity, was at baseline (t0), day 7th (t1), 10th (t2), and 14th (t3) (n=5/each group).
FIG. 16D is a series of photographs showing immunofluorescence studies of MM.1S-GFP+ cells ex vivo, on TEB scaffolds. Nuclei were stained using DAPI. One representative image from each group is shown (40×).
FIG. 16E is a bar graph showing quantification of MM cells ex vivo. MM.1S GFP+ cells were counted in 4 different regions of each tissue engineered bone (T.E.B.) scaffold, from each mouse. Average count is shown. Bars indicate s.d.
Figure 16:
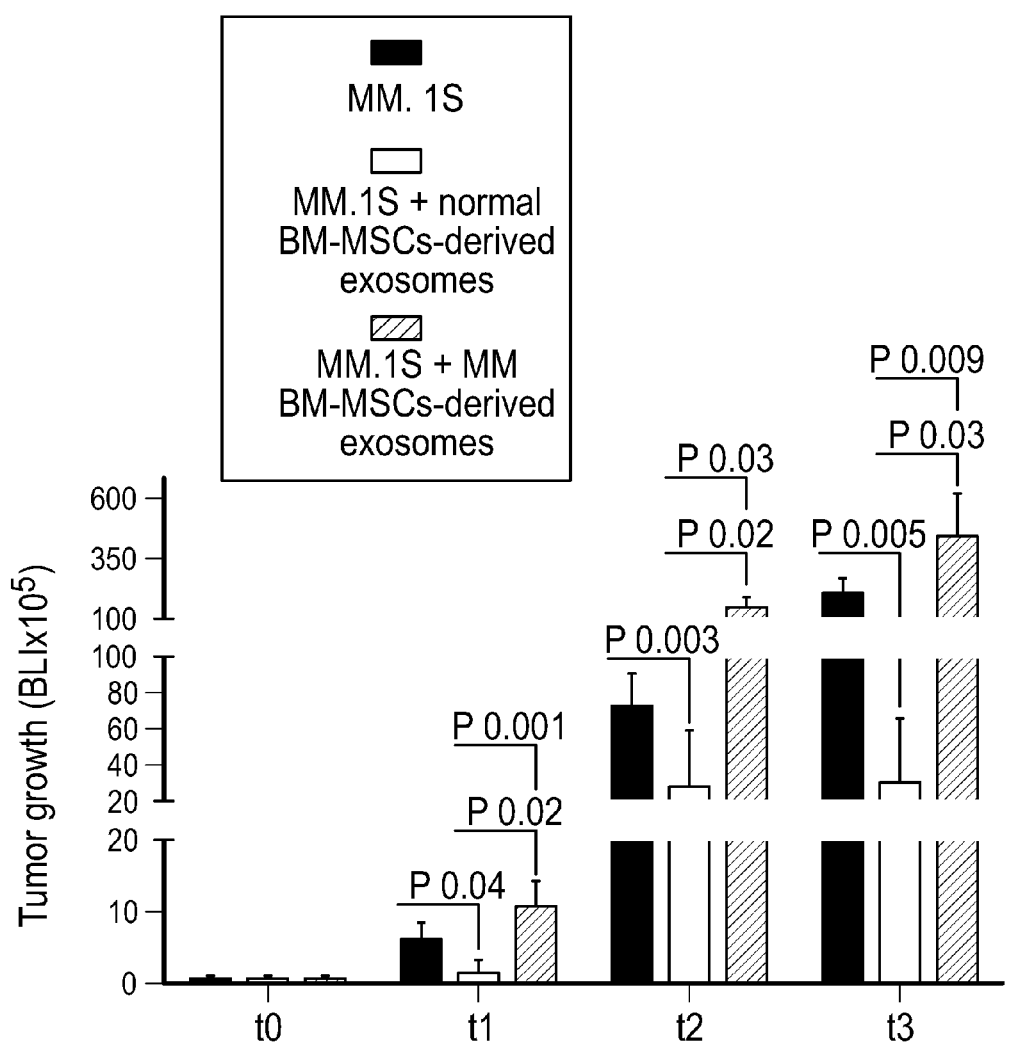
Figure 16:
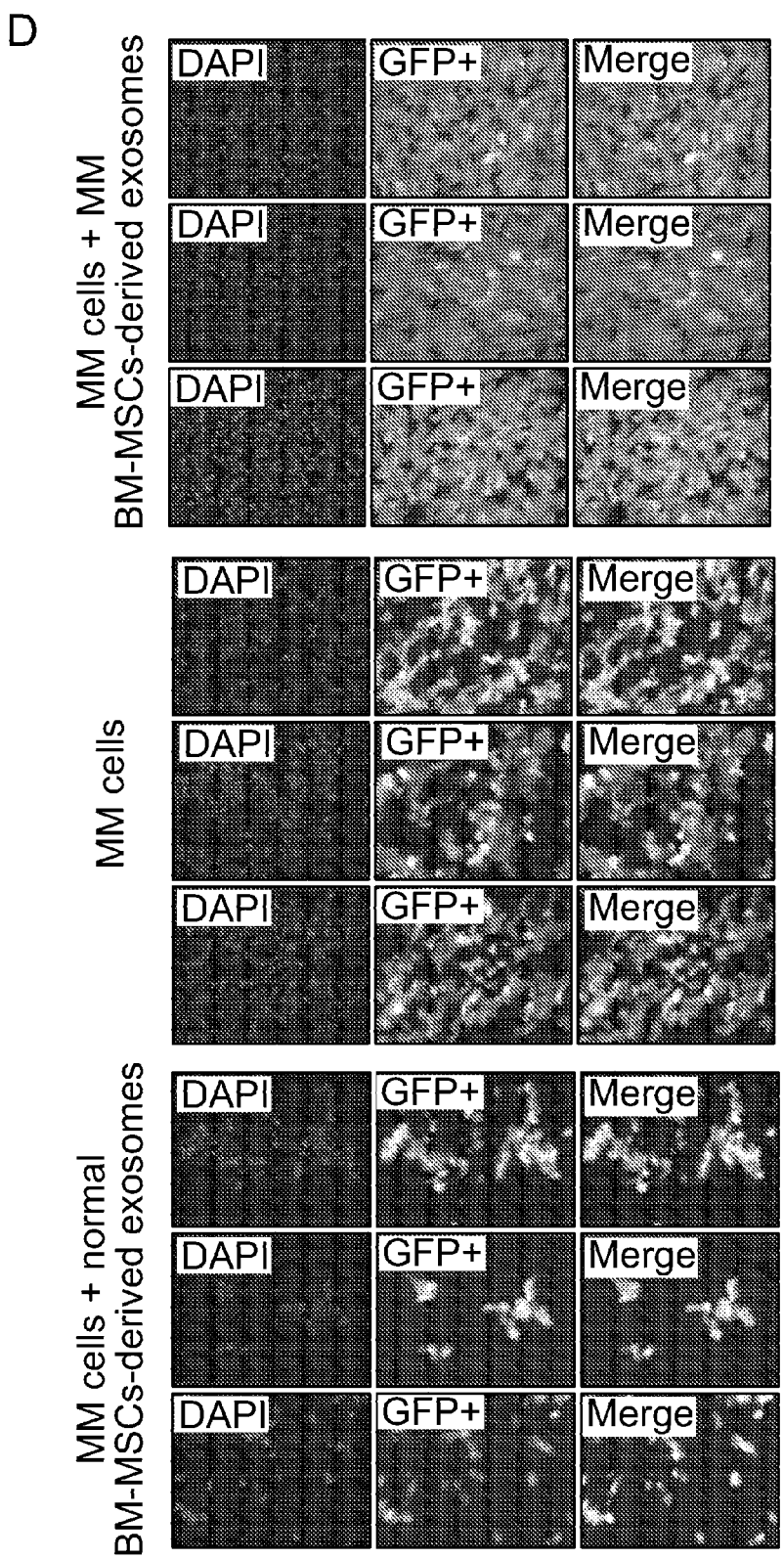
Figure 16:
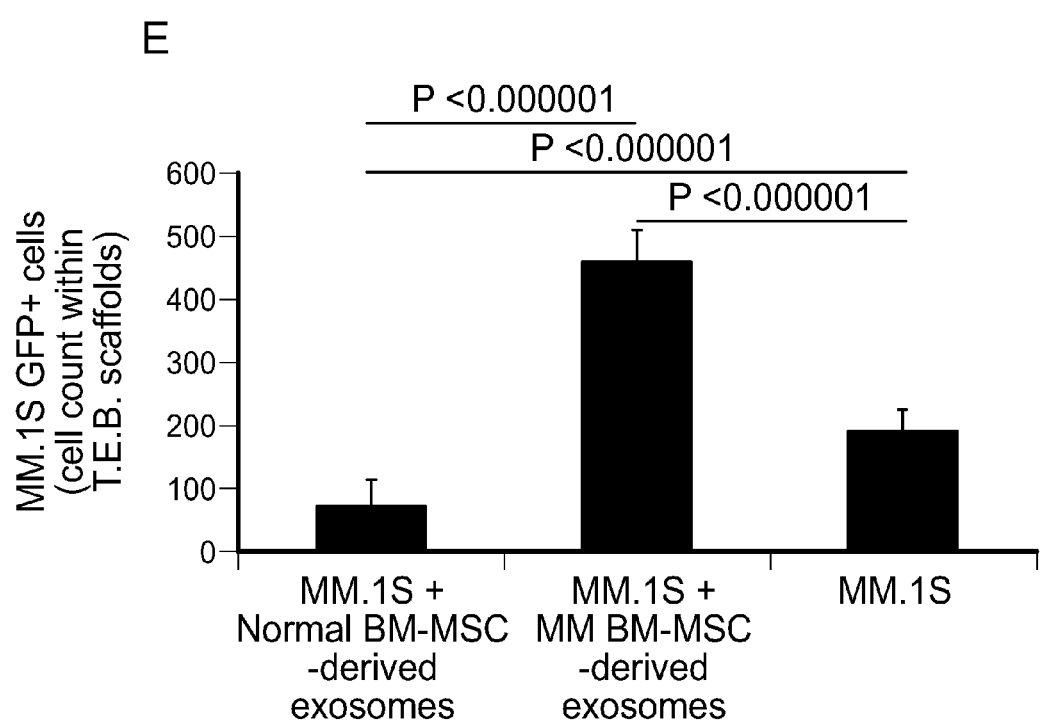

MM cells (MM.1S; RPMI.8226) were exposed to increasing concentrations of conditioned medium-derived exosomes isolated from both primary normal and MM BM-MSCs. Exosome were tested for their functional effects at concentrations previously reported (19, Montecalvo A. et al., *J Immunol.,* 180(5):3081-3090 (2008), Yu S. et al., *J Immunol.,* 178(11):6867-6875 (2007)). Normal BM-MSC-derived exosomes were able to significantly reduce MM cell proliferation compared to MM-MSC-derived exosomes, which slightly increased MM cell growth in vitro. Similar findings were confirmed using exosomes isolated from 4 primary MM BM-MSCs, 2 monoclonal gammopathy of undetermined significance (MGUS), 2 smoldering-MM and 4 primary normal BM-MSCs (FIG. 16A; FIG. 16B).

Normal and MM BM-MSC-derived exosomes' ability to modulate MM cell growth and dissemination in vivo was next investigated. Tissue-engineered bones (TEBs) were loaded with equal number of MM.1S-GFP+/Luc+ in the presence of either primary MM-MSC-derived exosomes or primary normal-MSCs-derived exosomes (Goldstein R. H. et al., *Cancer Res.,* 70(24):10044-10050 (2010)). TEBs loaded with MM.1S-GFP+/Luc+ cells were used as control. TEBs were then injected subcutaneously in SCID mice. Tumor burden was evaluated by using bioluminescence in vivo imaging. It was found that mice had similar tumor penetrance at t0; while at day $7^{th}$, $10^{th}$, and $14^{th}$ after the implant, mice implanted with MM BM-MSC-derived exosomes had a significantly higher tumor growth rate compared to mice that received MM cells only or those mice implanted with normal BM-MSC-derived exosomes (FIG. 16C).

These findings were further confirmed by immunofluorescence on TEB scaffolds ex vivo (FIG. 16D). A significantly higher number of MM cells was documented in those TEBs loaded with MM BM-MSC-derived exosomes versus TEB loaded with normal BM-MSC-derived exosomes (FIG. 16E), suggesting that the presence of normal MSCs-derived exosomes inhibited tumor growth, while the presence of MM-MSCs-derived exosomes induced tumor growth, compared to control MM cells alone.

Figure 17:
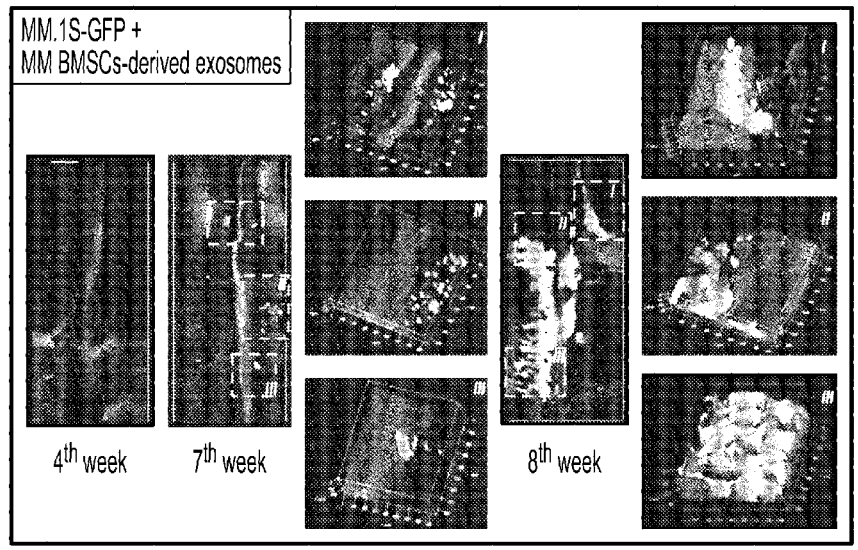
FIG. 17A is a series of photographs of confocal images showing MM cells homing to the bone marrow (BM). GFP+ MM cells (bright). Evans Blue positive-blood vessels (dull). Specific BM niches are highlighted with dotted lines. A 3D reconstruction is also provided.
FIG. 17B is a series of photographs of confocal images showing MM cells homing to the BM. Specific BM niches were obtained by changing the focal plane, moving towards the skull of the mouse, and highlighted with continuous white line. A 3D reconstruction is also provided.
FIG. 17C is a series of photographs of confocal images showing MM cells homing to the bone marrow (BM). GFP+ MM cells (bright). Evans Blue positive-blood vessels (dull). Specific BM niches are highlighted with dotted lines. A 3D reconstruction is also provided.
FIG. 17D is a series of photographs of immunofluorescence studies to detect MM.1S-GFP+ cells ex vivo on bone tissues. Nuclei were stained using DAPI. One representative image for each mouse from each group is shown (40×).
FIG. 17E is a bar graph showing the quantification of MM cells ex vivo. MM.1S GFP+ cells were counted in four different regions of each femur, from each mouse. Average count is shown. Bars indicate s.d.
Figure 17:
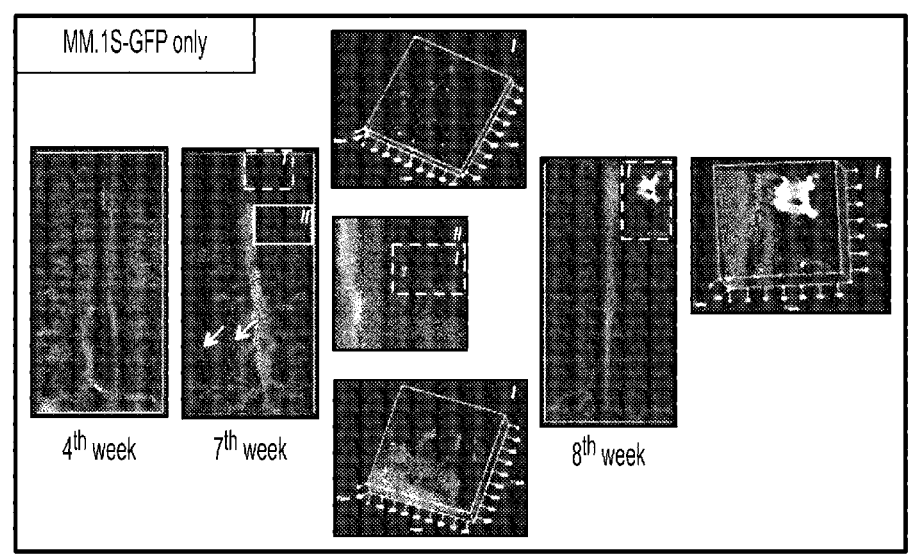
Figure 17:
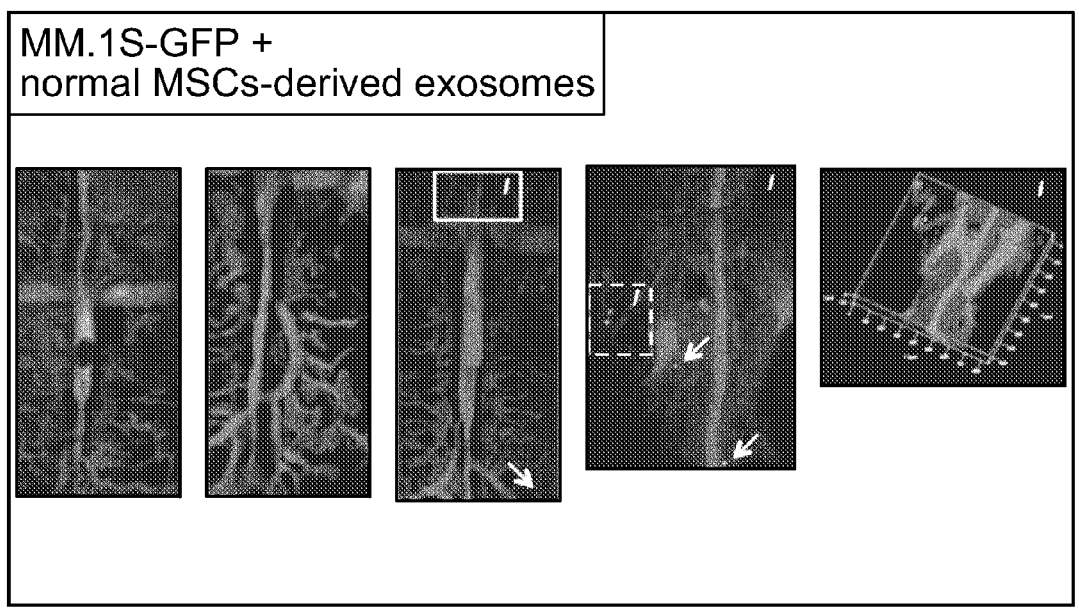
Figure 17:
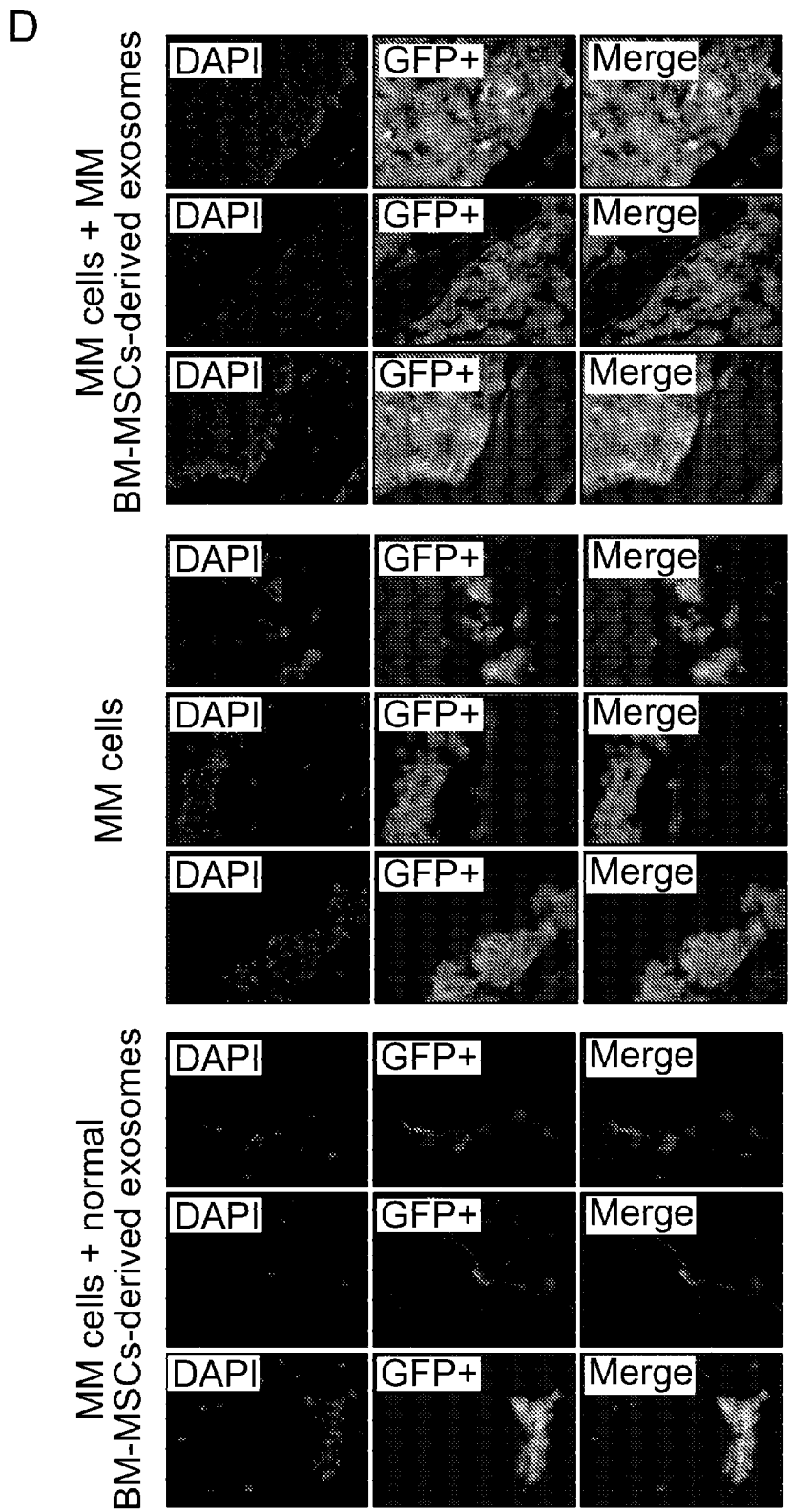
Figure 17:
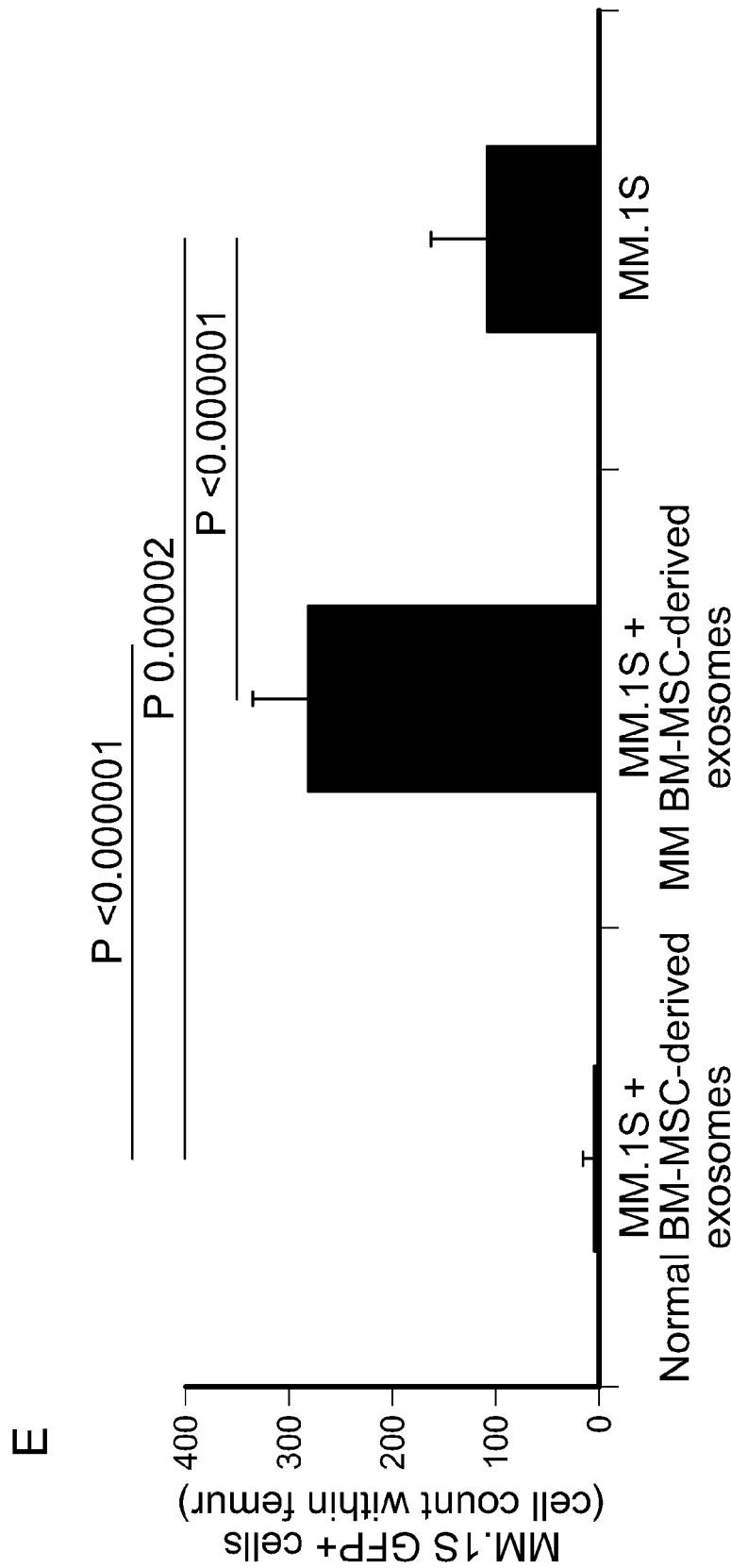

To further corroborate the differential impact of exosomes in regulating MM cell pathogenesis, it was next examined whether MM BM-MSCs derived exosomes could also induce cell dissemination and metastasis to distant bone marrow niches, which is a hallmark of MM. By using in vivo confocal imaging, it was possible to visualize the BM vasculature and the possible presence of GFP+ MM cells (Sipkins D. A. et al., Nature, 435(7044):969-973 (2005)). Mice were imaged four weeks after the s.c implant of the TEBs, and this time point was considered as baseline across the three cohorts of animals, where no detection of GFP+ MM cells was observed. Mice were imaged at $7^{th}$ and $8^{th}$ week post-implant, and clear differences were observed in the ability of MM cells to disseminate to the distant BM niches in vivo. At the $7^{th}$ week, a higher tumor burden was observed in those mice that received implants of TEB loaded with MM cells exposed to MM-BM-MSC-derived exosomes (FIG. 17A) compared to TEB loaded with MM cells only (FIG. 17B). In contrast, in mice implanted with TEB loaded with MM cells mixed with normal BM-MSC-derived exosomes, only a weak GFP signal was detected (FIG. 17C). These results were further corroborated by femur bone marrow immunofluorescence ex vivo (FIG. 17D; FIG. 17E). These findings suggest that BM-MSCs play an oncogenic role in the progression and widespread dissemination of this disease.

Example 18. Exosomal miRNA and Protein Content Differs Between Normal and MM BM-MSCs Large amounts of small RNAs have recently been reported in exosomes, suggesting that they may contain microRNAs (miRNA). Indeed the presence of miRNAs in exosomes has been documented in mast cells (Valadi H. et al., Nat. Cell Biol., 9(6):654-659 (2007)). Thus, it was hypothesized that BM-MSC-derived exosomes may differ in their miRNA content, leading to epigenetic transfer of this information to the tumor clone. miRNA expression profiling was next performed on exosomes isolated from normal BM-MSCs, MGUS- and MM BM-MSCs. Supervised clustering analysis comparing normal versus MM and MGUS BM-MSC-derived exosomes showed statistically significant differences between the two cohorts of samples: specifically, reduced expression of 16 miRNAs and increased expression of 2 miRNAs was observed in MM BM-MSCs-derived exosomes compared to normal- and MGUS-BM-MSCs-derived exosomes, which presented with a similar pattern (FIG. 18A; P<0.05). In particular, it was found that miRNA-15a was one of the down-modulated miRNAs in MM-BMSC-isolated exosomes. This lower miRNA15a levels was validated in an additional 5 MM-BM-MSC-derived exosomes, as compared to 2 normal BM-MSC-derived exosomes.

Figure 18:
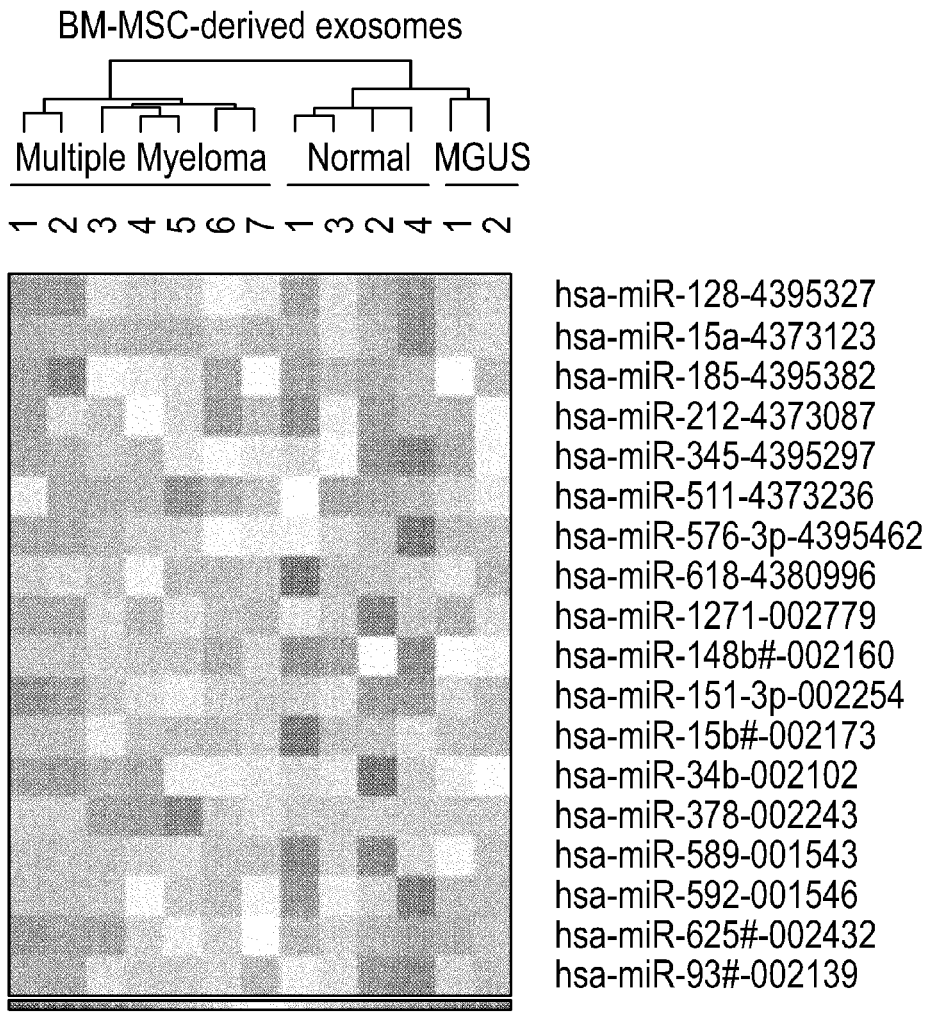
FIG. 18A is a heatmap that provides the results of miRNA expression profiling has been performed on total RNA isolated from normal (n=4), MM (n=7), and MGUS (n=2) BM-MSC-derived exosomes. Differential expression of miRNA is shown by the intensity of red (up-regulation) versus blue (down-regulation) (d-Chip software; normal vs MM: 1.5 fold change; P<0.05). The intensity of color in each cell correlates with the degree of increase or decrease in expression.
FIG. 18B provides a bar graph showing the expression levels of hsa-miRNA-15a in MM cells (MM.15; RPMI.8226) cultured in the absence (−) or the presence of either primary MM (n=4) or normal (n=3) BM-MSCs, or HS-5 cell line for 48 hours. Expression levels were determined using the ΔΔCt method, with normalization to the reference RNU6B miRNA. Average of three independent experiments is shown. Bars represent s.d.
FIG. 18C is a bar graph showing mmu-miRNA-15a levels in human MM cells by qRT-PCR, using the ΔΔCt method with normalization to the reference C. elegans miRNA-39 used as spiked control. Murine exosomes have been isolated from the BM of either C57BL/6 or C57BL/6 miRNA-15a/16-1−/− mice; and subsequently added to MM cells (MM.1S; RPMI.8226) for 48 hours. Bars represent s.d.
FIG. 18D is a bar graph showing cell proliferation of MM cells (assessed using [$^3$H]-thymidine uptake) cultured in the presence or the absence of murine C57BL/6 BM-MSCs (either wild type or miRNA-15a/16-1−/−) for 48 hours. Bars indicate s.d.
FIG. 18E is a bar graph showing cell proliferation (assessed using [$^3$H]-thymidine uptake) of MM cells exposed for 48 hours to conditioned medium-derived exosomes isolated from HS-5 cells transfected with either scramble-, pre-miR-15a-, or anti-miR-15a-probe. Control indicates non-containing cell conditioned media processed as in all the samples tested. Bars indicated s.d.
FIG. 18F is a bar graph showing cell proliferation (assessed using [$^3$H]-thymidine uptake) of MM cells exposed for 48 hours to conditioned medium-derived exosomes isolated from primary BM-MSCs transfected with either scramble-, pre-miR-15a-, or anti-miR-15a-probe. Control indicates non-containing cell conditioned media processed as in all the samples tested. Bars indicate s.d.
Figure 18:
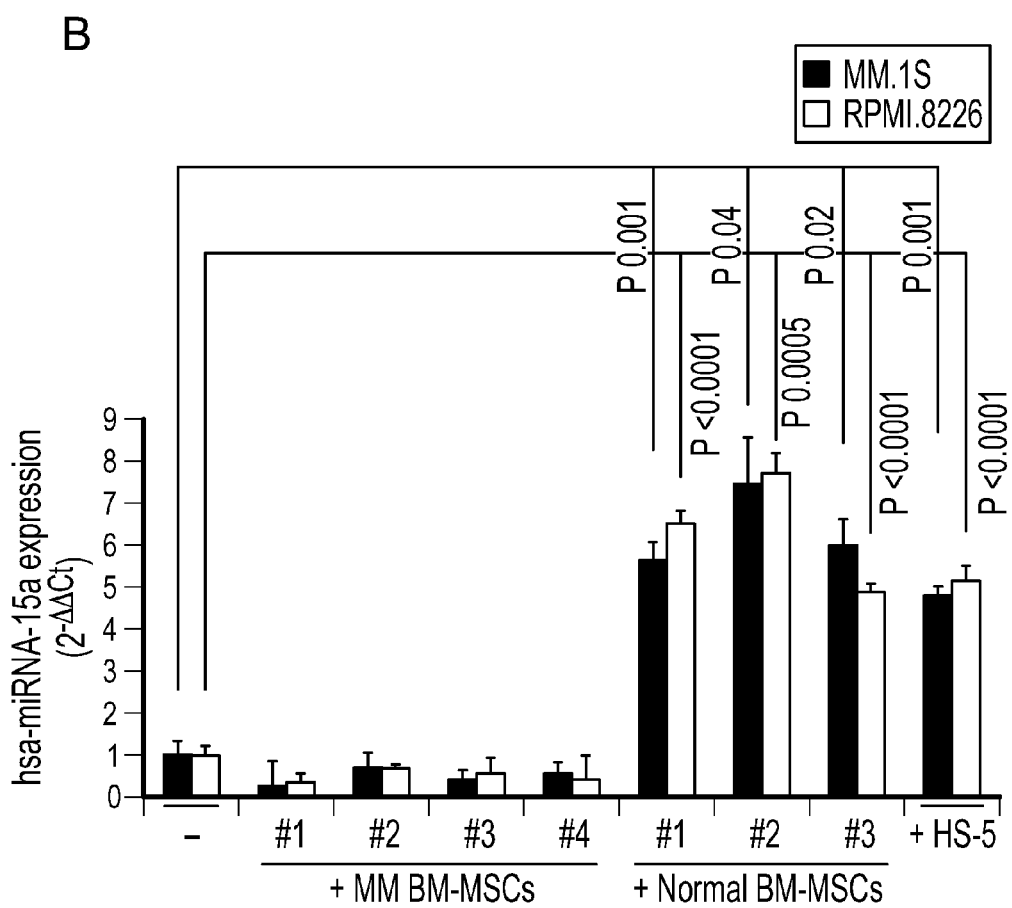
Figure 18:
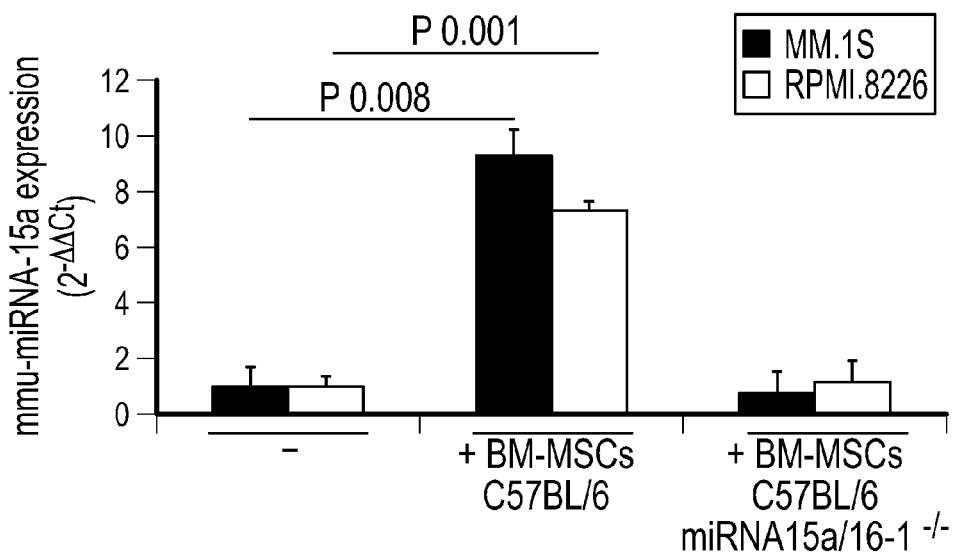
Figure 18:
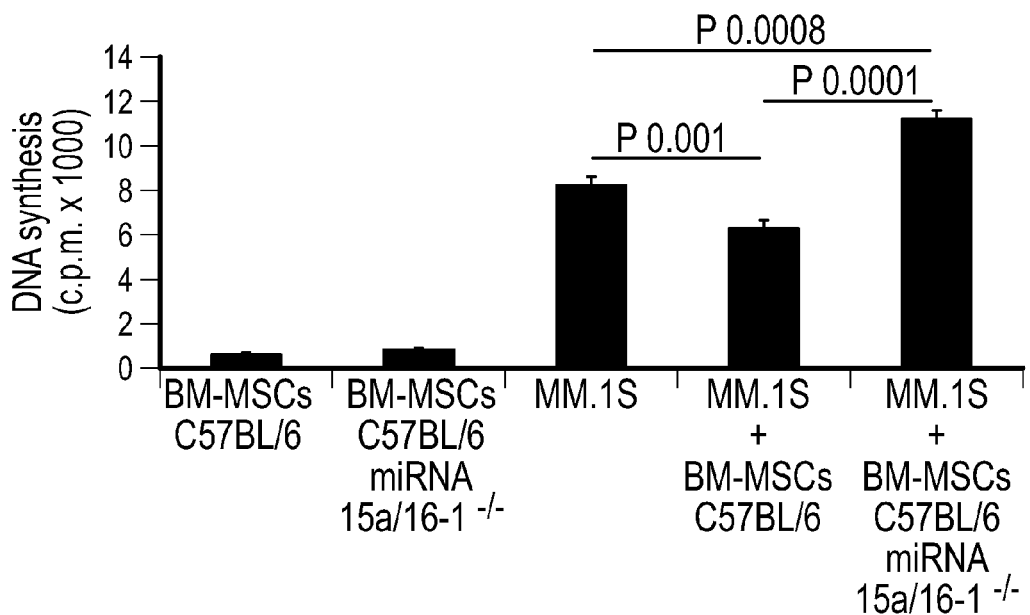
Figure 18:
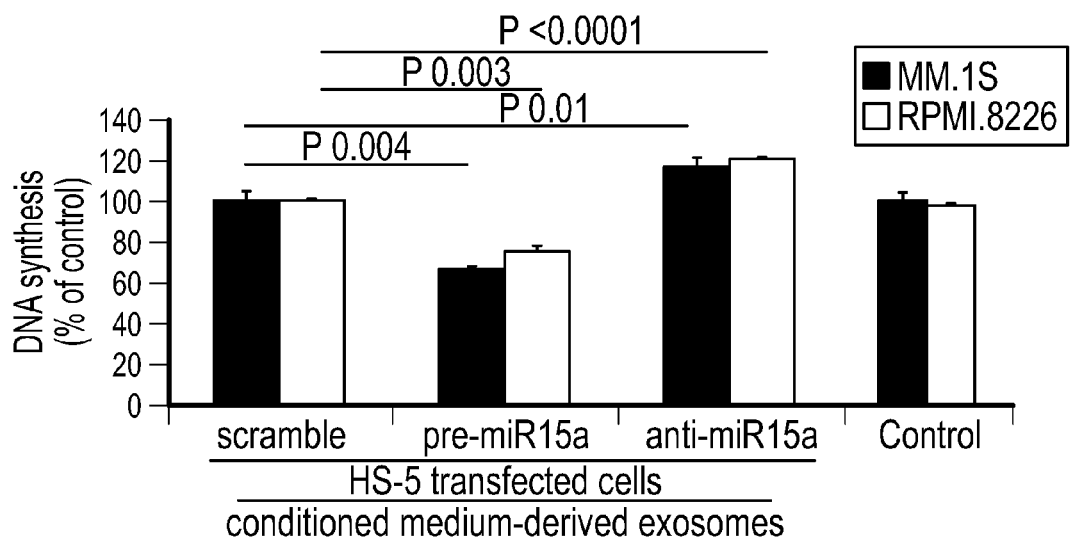
Figure 18:
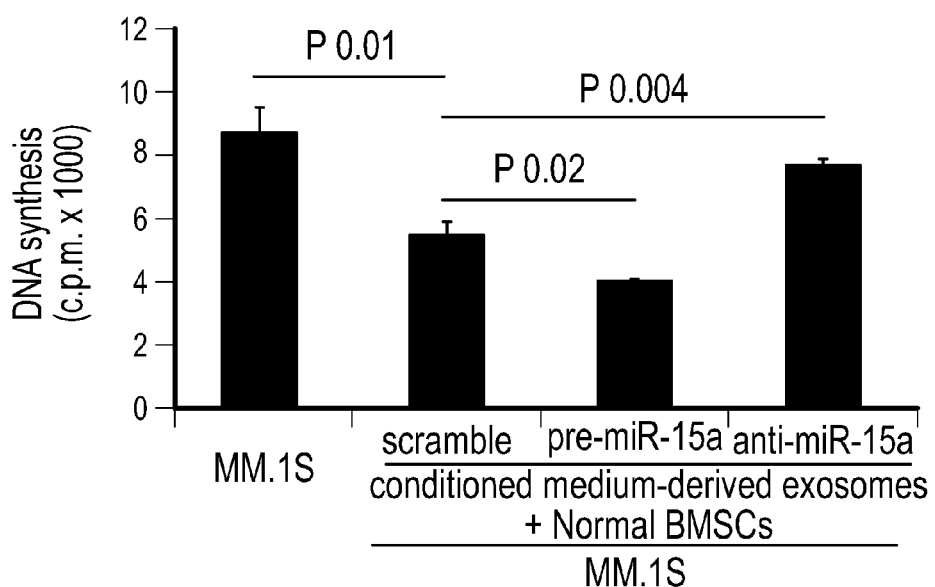

The presence of miRNAs in exosomes led to the hypothesis that exosomes may represent an active vehicle between the BM microenvironment and MM cells, thus functionally modulating the biological behavior of MM cells. Primary MM cells present with reduced expression of miRNA-15a compared to their normal cellular counterpart, and functional studies have corroborated the role of miRNA-15a as a tumor suppressor miRNA in this disease (Roccaro A. M. et al., Blood, 113(26):6669-6680 (2009)). However, the finding that miRNA-15a is also deficient in MM BM-MSCs and not only in the tumor clone, led to the hypothesis that the lack of this miRNA in the transfer of exosomes from the MM BM-MSCs to the tumor clone mediates oncogenesis in MM. The expression of miRNA-15a in BM-MSCs was evaluated and it was found that primary normal BM-MSCs have a higher expression of miRNA-15a compared to primary MM BM-MSCs. In addition, miRNA-15a level in HS-5 was comparable to normal primary BM-MSCs. The expression of miRNA-15a in MM cells cultured either alone or in the presence of BM-MSCs was next evaluated and it was found that miRNA-15a level was significantly up-regulated in MM cells that were co-cultured with normal BM-MSCs or HS-5, but not with MM BM-MSCs, suggesting transfer of miRNA-15a from BM-MSCs to MM plasma cells (FIG. 18B). To further confirm that miRNA-15a is actively transferred to the tumor cells, C57BL/6 miRNA15a/16-1$^{-/-}$ and C57BL/6 wild type mice were used. Murine BM-MSC-derived exosomes were isolated from MSCs of C57BL/6 mice, either wild type or 15a/16-1$^{-/-}$. Levels of mmu-miRNA-15a and -16-1 have been confirmed by qRT-PCR on both BM-MSCs and BM-MSC-derived exosomes from either C57BL/6-15a/16-1$^{-/-}$ or wild type mice. After co-culture of MM cells with wild type murine BM-MSCs-derived exosomes, an increased expression of mmu-miRNA-15a was demonstrated in MM cells, further proving transfer of MSC-derived exosomes containing miRNA-15a into the plasma cells. No changes were observed in MM cells exposed to C5BL/6 miRNA-15a/16-1$^{-/-}$ BM-MSCs-derived exosomes (FIG. 18C). Similar findings were demonstrated for miRNA-16-1. It was next sought whether murine miRNA-15a/16-1$^{-/-}$ BM-MSCs can functionally target MM cells. MM cells were cultured in presence or absence of BM-MSCs isolated from either C57BL/6 or C57BL/6 miRNA15a/16-1$^{-/-}$ mice. These studies demonstrated that miRNA15a-deficient BM-MSCs significantly induced MM.1S cell proliferation (FIG. 18D). Similar results were obtained using RPMI.8226.

To further confirm that miR-15a plays a critical role in MSC-mediated tumor progression, loss- and gain-of-function studies were performed. HS-5 cells were transfected with either pre- or anti-miRNA-15a. Transfection efficiency was tested by qRT-PCR. MM cells were exposed to exosomes isolated from HS-5 transfected cells for 48 hours Importantly, exosomes isolated from pre-miRNA-15a-transfected HS-5 significantly inhibited MM cell proliferation (FIG. 18E). To further confirm the ability of miRNA-15a-containing exosomes to inhibit MM cell proliferation, exosomes were collected from primary BM-MSCs transfected with either pre- or anti-miRNA-15a. Transfection efficiency was tested by qRT-PCR. A lower proliferation rate of MM.1S cells exposed to exosomes isolated from pre-miRNA-15a-transfected BM-MSCs was demonstrated (FIG. 18F). Similar results were obtained using RPMI.8226 cells.

Together, these studies confirm that miRNA-15a acts as a tumor suppressor miRNA that is present in normal BM-MSCs but absent in MM BM-MSCs, and the lack of exosomes-mediated miRNA15a-transfer to malignant plasma cells is permissive for the growth and dissemination of clonogenic MM cells.

Figure 19:
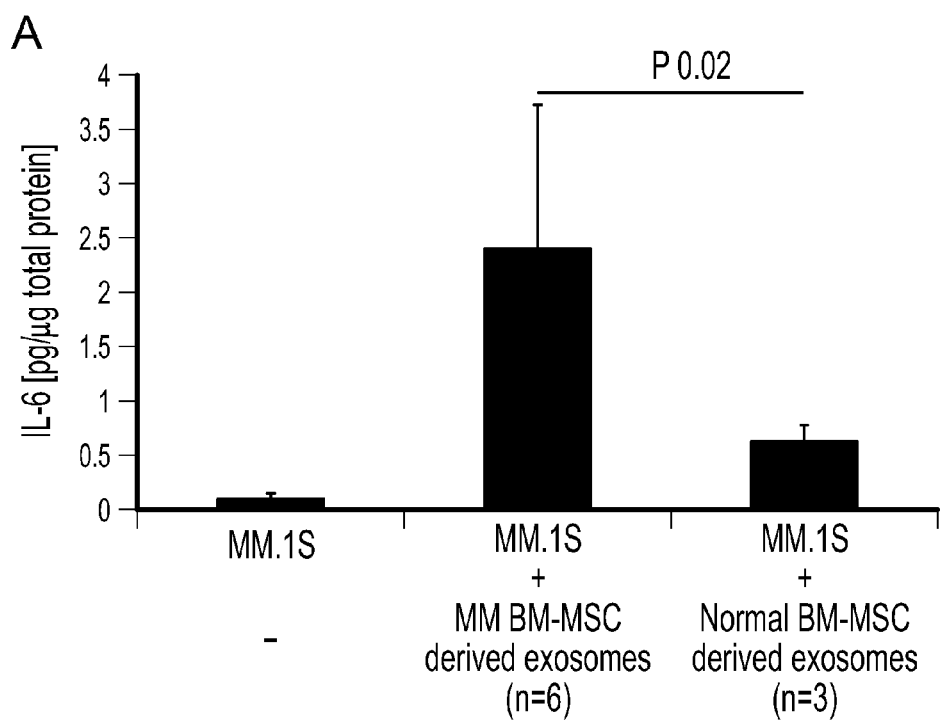
FIG. 19A is a bar graph showing IL-6 concentration (calculated as pg/μg of total protein) in MM.1S cells exposed to exosomes isolated from either MM BM-MSCs (n=6) or normal BM-MSCs (n=3), for 24 hours. IL-6 was measured on conditioned media, using a human IL-6 ELISA. Bars indicate s.d.
FIG. 19B is a bar graph showing IL-6 concentration (calculated as pg/μg of total protein) in MM.1S cells exposed to exosomes isolated from either MM BM-MSCs or normal BM-MSCs, for 24 hours. IL-6 was measured on conditioned media, in presence or absence of IL-6 blocking antibody (0.2 μg/mL) using human IL-6 ELISA. IL-6 concentration was calculated as pg/μg of total protein. Mouse IgG2B isotype control was used. Bars indicate s.d.
FIG. 19C is a photograph of Western blots using anti-fibronectin, -junction plakoglobin, -CCL2 and -actin antibodies on MM-(n=6) and normal-(n=3) BM-MSCs-exosome-derived proteins.
FIG. 19D is a bar graph showing the percentage of adherent MM cells (MM.1; RPMI8266) after adhesion for 2 hours to BSA-(negative control), poly-D-Lysine-(positive control), and fibronectin-coated wells, exposed or not to MM (n=4)- or normal (n=3)-BM-MSC-derived exosomes (200 μg/mL; 6h). All data represent mean (±sd) of triplicate experiments. Control indicates non-containing cell conditioned media processed as in all the samples tested.
FIG. 19E is a scatter plot showing exosomal and cellular protein content of MM- and normal-BM-MSC-derived samples. Logarithm base 2 fold changes of the proteins with a logarithm fold change greater than 0.1, based on the exosomal content.
Figure 19:
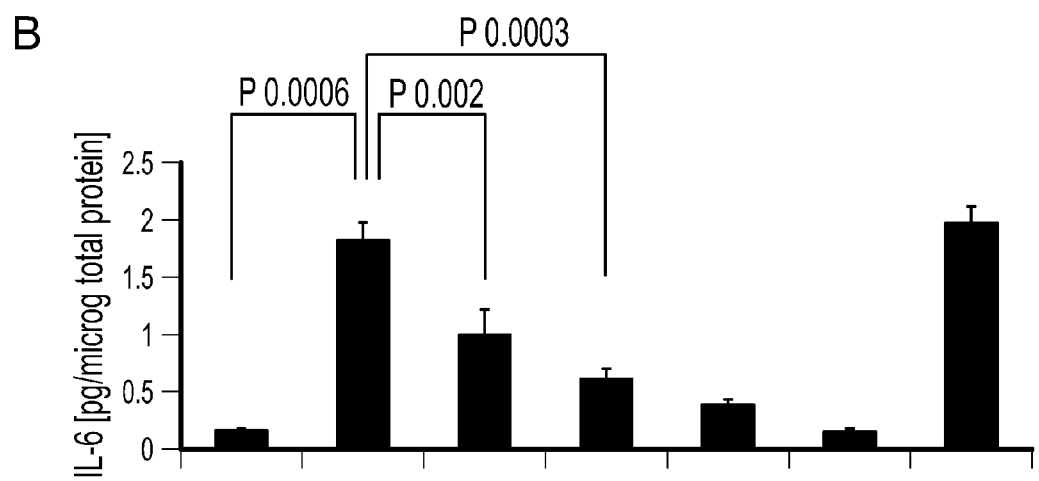
Figure 19:
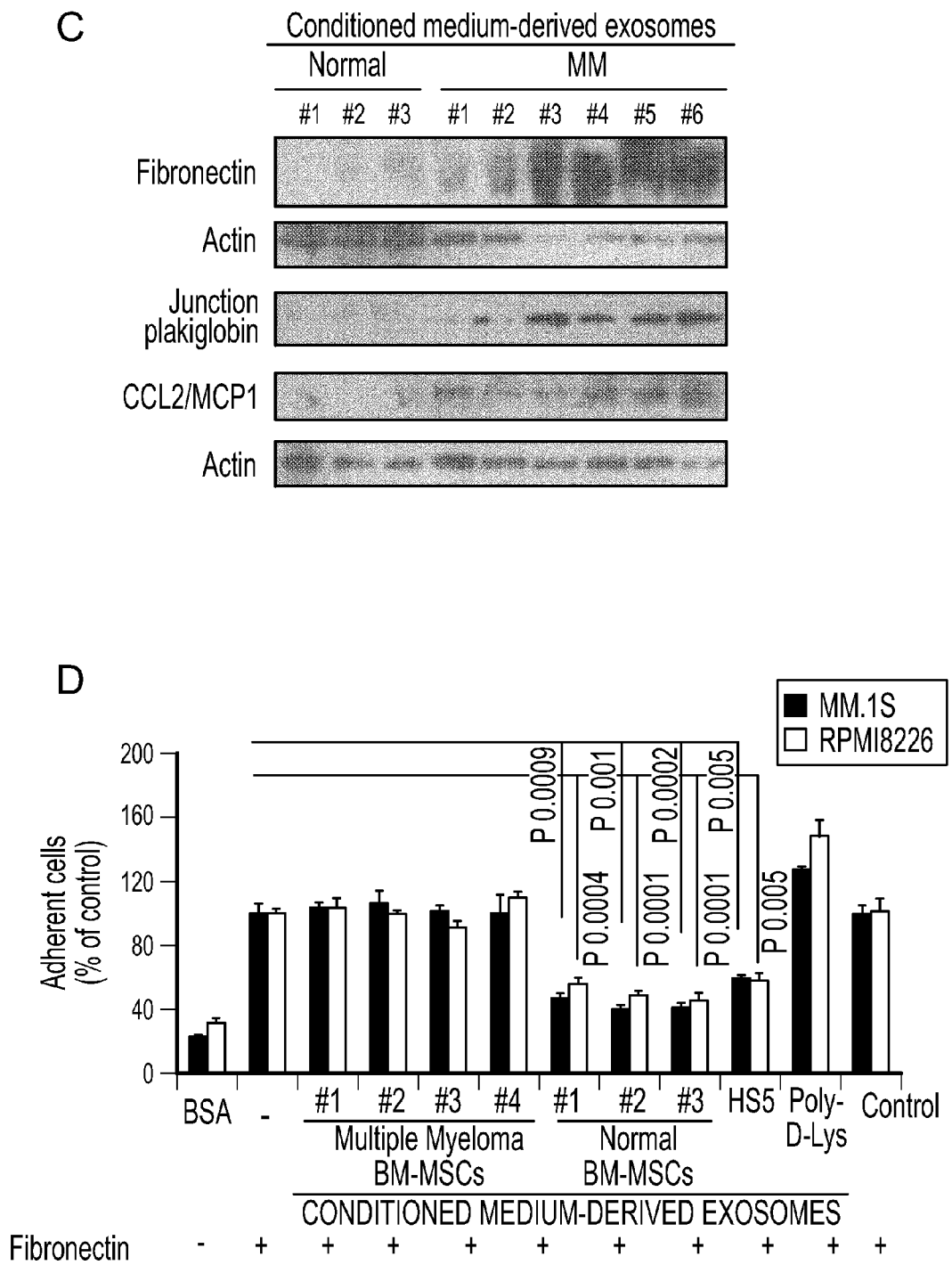
Figure 19:
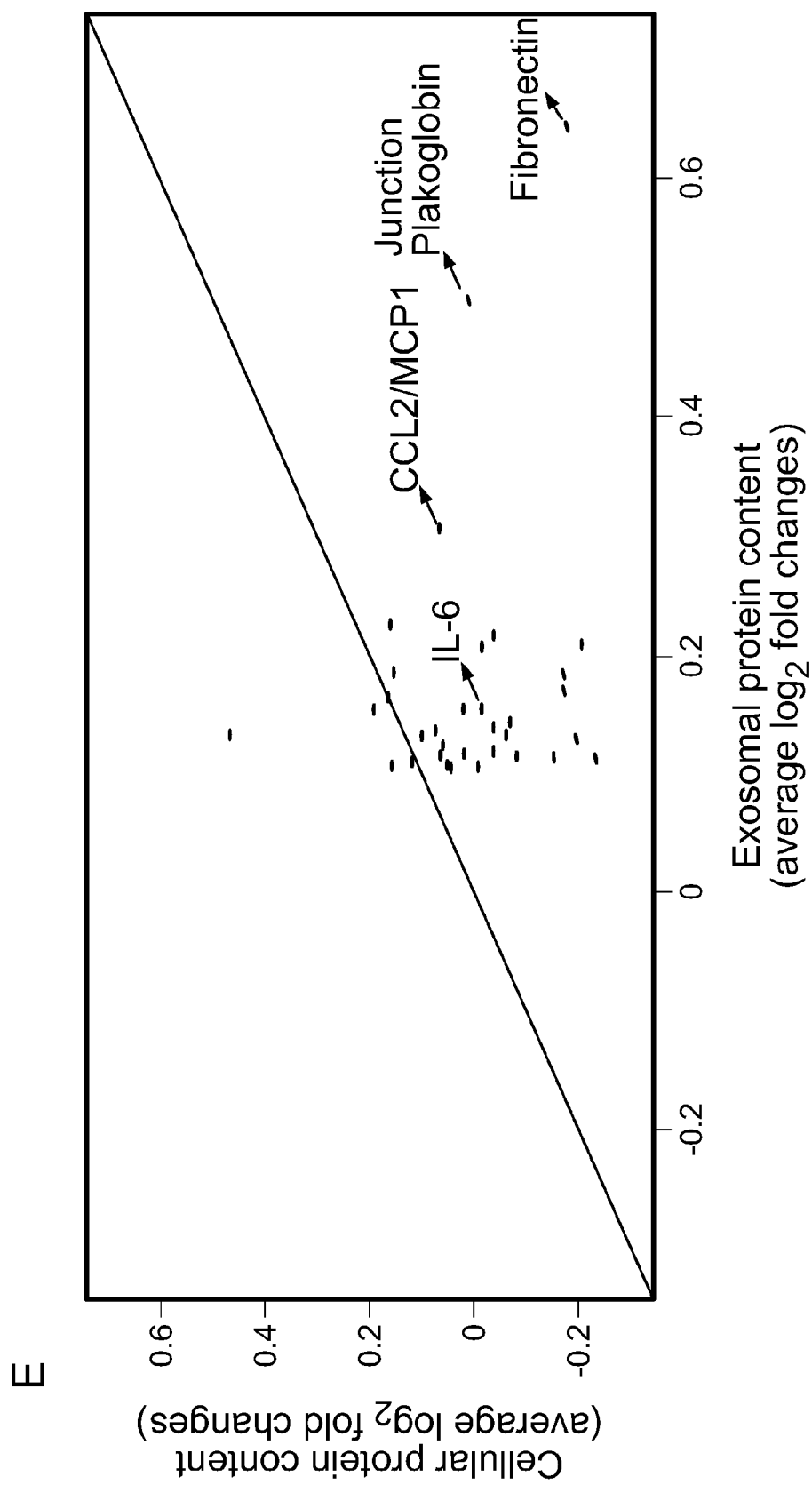
Figure 20:
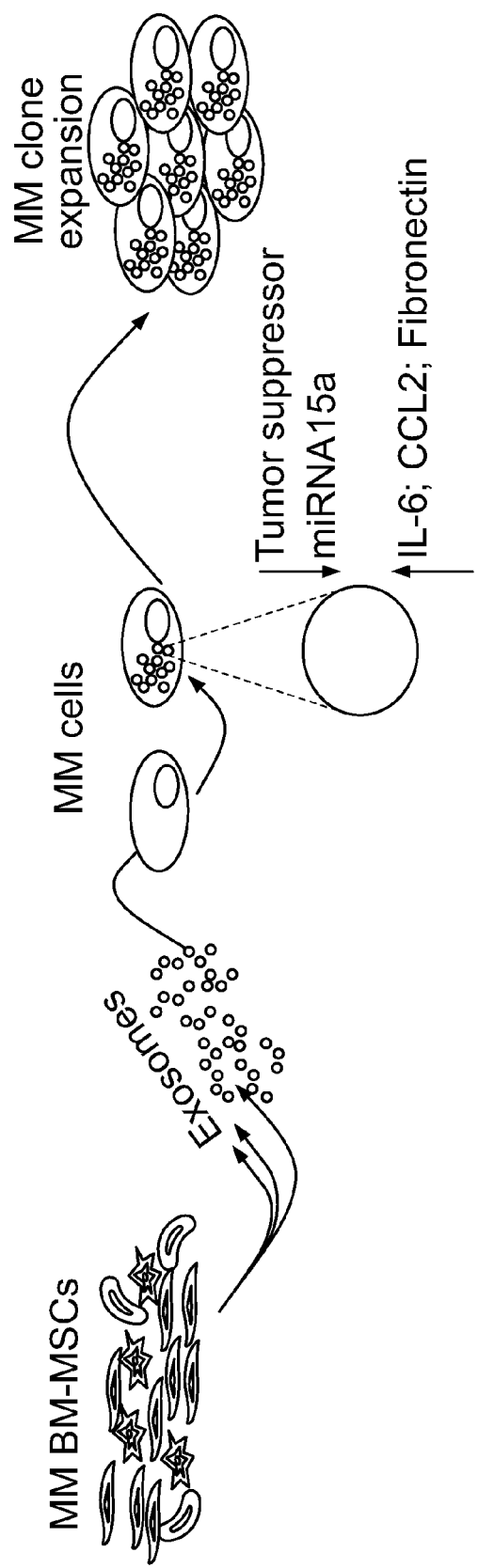
FIG. 20 is a schematic representation of a model for how bone marrow mesenchymal stromal cells (BM MSC)-derived exosomes support multiple myeloma (MM) clone expansion.
Figure 21:
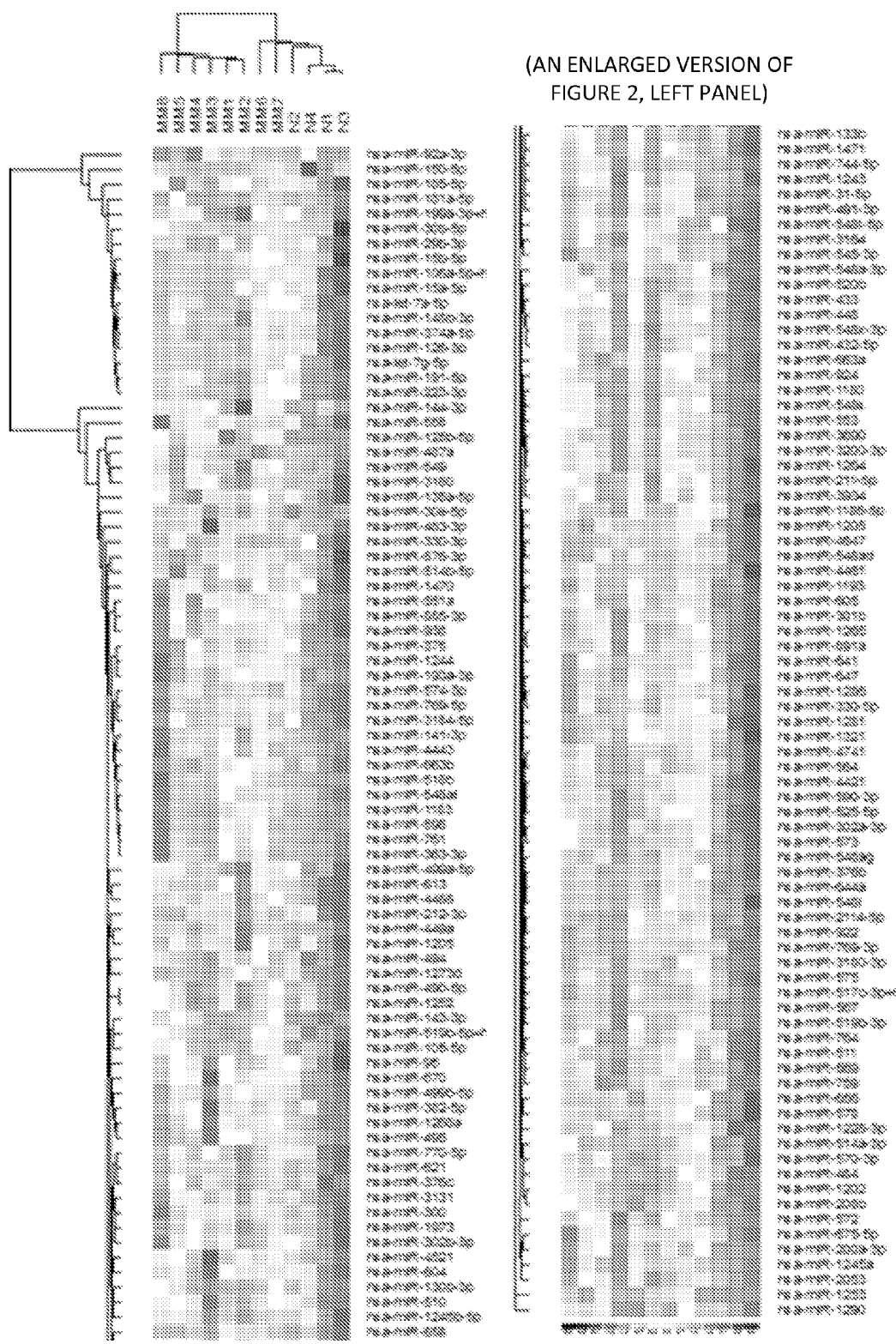

However, the lack of transfer of tumor suppressor miRNAs could not explain all of the changes that occurred in MM cells in responses to exosomes isolated from MM-MSCs. Therefore, it was next sought to determine whether exosomes may selectively transfer certain proteins from the BM-MSCs to the recipient tumor plasma cells. High-throughput antibody-based protein array was performed on exosomes isolated from primary normal- and MM-BM-MSCs, as well as on the whole population of normal- and MM-BM-MSCs. Results indicated that BM-MSC-derived exosomal proteins differ from BM-MSC-derived cellular proteins, suggesting that MM BM-MSC-derived exosomes present with a specifically higher fold change of IL-6-, CCL2/MCP1-, junction plakoglobin- or fibronectin-content, that does not reflect the protein content of the cells of origin, where indeed IL-6, fibronectin, CCL2/MCP1 and junction plakoglobin presented with minimal changes between normal and MM BM-MSCs. These findings suggest that exosomes may selectively transfer certain proteins to the recipients cells, thus behaving as vesicles that selectively transport specific proteins to cells they interact with (FIG. 19E). It has been reported that CCL2/MCP1 plays a crucial role in MM pathogenesis and disease progression, as demonstrated both in vitro and in vivo: our findings indicate also that MM-BM-MSC-derived exosomes present with higher expression of CCL2/MCP1, compared to the related normal counterpart, thus confirming the role of this protein in supporting MM biology.

To determine whether the differentially expressed exosomal protein content between MM- and normal-BM-MSCs, could functionally affect MM cells, MM cells were exposed to exosomes isolated from either MM BM-MSCs or normal BM-MSCs, and it was found that IL-6 levels were increased in the conditioned media of MM cells exposed to MM BM-MSC-derived exosomes, compared to normal BM-MSC-derived exosomes (FIG. 19A). A recent study on the proteomic content of exosomes and their function indicates that the proteins are not restricted to the interior of the exosome (Khan S. et al., *Apoptosis*, 16(1):1-12 (2011)). Exosomal proteins may therefore be released from the intra-exosomal space and interact with extracellular proteins via undefined mechanisms. These data are similar in showing that MM BM-MSC-derived exosomes leads to increased IL-6 amount in the conditioned medium. It was next demonstrated that MM BM-MSC-derived exosomes-dependent induction of IL-6 release from MM cells was significantly abolished when cells were exposed to IL-6 blocking antibody, thus indicating that IL-6 released by exosomes is functionally important in the growth of MM cells (FIG. 19B).

Moreover, detection of fibronectin, CCL2/MCP1, junction plakoglobin was further confirmed by western blot (FIG. 19C). Since it was observed that exosomes from MM BM-MSCs presented with higher fibronectin content, and based on accelerated cell dissemination of MM cells to distant BM niches, it was next examined whether exosomes regulate adhesion properties of MM cells to the surrounding BM milieu, and found reduced adhesion of MM cells to fibronectin when cultured in the presence of primary normal BM-MSCs-derived exosomes, whereas MM BM-MSC-derived exosomes did not affect their ability to adhere to fibronectin (FIG. 19D). Moreover, down-modulation of phosphorylation of adhesion protein cofilin was documented when MM cells were treated with normal MSCs-derived exosomes compared to MM-MSCs-derived exosomes, where a modest up-regulation of p-cofilin was observed.

Example 19. miR-155 Levels in Peripheral Blood Samples of CLL and WM Patients

A total of 105 CLL and 85 WM peripheral blood samples were collected from patients and the miR-155 levels in these samples were compared to 22 normal peripheral blood samples. RT-PCR was performed for miR-155 to determine the level of this miRNA in these samples. The relative ratio of expression of miR-155 was 120 times higher in the CLL samples compared to the normal controls; whereas, it was 16 times higher in the WM samples compared to normal controls. Detectable levels of miR-155 were observed in 85% of CLL samples, 75% of WM samples but only detectable in 14% of normal control samples.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
administering to a human subject a treatment that ameliorates a hematological malignancy, wherein the hematological malignancy is not chronic lymphocytic leukemia, and the human subject has been determined to have in a biological sample obtained from the human subject
a) an increased expression relative to a control level of at least one of miR-450a, miR-30e, miR-125a, miR-300, miR-30d, miR-144, miR-451a, miR-107, miR-125b, miR-143, miR-720, and miR-155;
b) a decreased expression relative to a control level of at least one of miR-185, miR-150, miR-98, miR-374b, miR-28, miR-92a, miR-32, miR-548a, miR-939, miR-99a, miR-345, miR-125a, miR-587, miR-323b, miR-let-7g, miR-223, miR-15a, miR-19b, miR-21, miR-let-7b, and miR-let-7c;
c) an increased expression relative to a control level of at least one of miR-450a, miR-30e, miR-125a, miR-300, miR-30d, miR-144, miR-451a, miR-107, miR-125b, miR-143, and miR-720; or
d) an increased expression of miR-155 relative to a control level.

2. A method comprising:
a) identifying a human subject who has a hematological malignancy, wherein the hematological malignancy is not chronic lymphocytic leukemia;
b) obtaining a biological sample from the human subject;
c) detecting in the biological sample that the human subject has an altered level of one or more micro RNAs (miRs) compared to the level in a control subject having an identified stage of the hematological malignancy,
wherein the one or more miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-587, miR-323b, miR-let-7g, miR-223, miR-15a, miR-19b, miR-21, miR-let-7b, and miR-let-7c; and d) administering to the human subject a treatment that ameliorates the hematological malignancy.

3. The method of claim 2, wherein:
a) if the human subject has an increased level compared to the control subject of one or more of miR-450a, miR-30e, miR-125a, and miR-300, or a decreased level compared to the control subject of one or more of miR-185, miR-150, and miR-98, the human subject is administered a treatment that is effective for the monoclonal gammopathy of undetermined significance (MGUS) stage of multiple myeloma (MM);
b) if the human subject has an increased level compared to the control subject of miR-107, or a decreased level compared to the control subject of one or more of miR-92a, miR-28, miR-32, miR-548a, miR-939, miR-99a, miR-345, miR-125a, miR-587, and miR-323b, the human subject is administered a treatment that is effective for the smoldering multiple myeloma (SMM) stage of MM;
c) if the human subject has an increased level compared to the control subject of one or more of miR-125b, miR-143, or miR-720, or a decreased level compared to the control subject of one or more of miR-let-7g, miR-223, miR-150, miR-15a, miR-19b, miR-21, miR-let-7b, or miR-let-7c, the human subject is administered a treatment that is effective for symptomatic MM; or
d) if the human subject has an increased level compared to the control subject of miR-155, the human subject is administered a treatment that is effective for Waldenstrom's macroglobulinemia (WM), small lymphocytic lymphoma (SLL), or follicular lymphoma.

4. A method for treating a human subject who is suspected of having, or who has, a hematological malignancy or a stage of a hematological malignancy, the method comprising:
a) identifying the human subject as being suspected of having, or having, a hematological malignancy or a stage of a hematological malignancy;
b) obtaining a biological sample from the human subject;
c) determining from the biological sample that the human subject has an altered level of one or more miRs compared to the level in a control subject who does not have the hematological malignancy, wherein the one or more miRs are selected from the group consisting of miR-450a, miR-30e, miR-125a, miR-300, miR-30d, miR-144, miR-451a, miR-107, miR-125b, miR-143, miR-720, miR-155, miR-185, miR-150, miR-98, miR-374b, miR-28, miR-92a, miR-32, miR-548a, miR-939, miR-99a, miR-345, miR-587, miR-323b, miR-let-7g, miR-223, miR-15a, miR-19b, miR-21, miR-let-7b, and miR-let-7c; and d) administering a treatment regimen comprising everolimus and an anti-CD20 antibody to the human subject with an increased level of miR-155 compared to the control subject;

administering a treatment regimen comprising anti-miR-155 to the human subject with an increased level of miR-155 compared to the control subject; or administering a treatment regimen comprising an miR-Let-7b or miR-Let-7c pre-miR to the human subject with a decreased level of miR-Let-7b or miR-Let-7c compared to the control subject, thereby treating the human subject who is suspected of having, or who has, the hematological malignancy or the stage of the hematological malignancy.

5. The method of claim 4, comprising determining the level of an miR selected from the group consisting of miR-155, miR-let-7b, and miR-let-7c after completion of the treatment regimen, wherein if the subject continues to have the altered level of the miR as determined before the treatment, the treatment is discontinued, and if the subject does not have the altered level of the miR as determined before the treatment, the treatment is continued.

6. The method of claim 4, wherein the biological sample is plasma or exosome-enriched plasma.

7. The method of claim 4, wherein the hematological malignancy is a low grade B cell malignancy selected from the group consisting of multiple myeloma, Waldenstrom's macroglobulinemia (WM), Chronic lymphocytic leukemia (CLL), small lymphocytic lymphoma (SLL), follicular lymphoma, marginal zone lymphoma, mantle cell lymphoma, and MALT lymphoma.

8. The method of claim 4, wherein the determining step is performed by quantitative RT-PCR.

9. The method of claim 1, wherein the biological sample is plasma or exosome-enriched plasma.

10. The method of claim 2, wherein the biological sample is plasma or exosome-enriched plasma.

* * * * *

UNITED STATES PATENT AND TRADEMARK OFFICE
CERTIFICATE OF CORRECTION

PATENT NO. : 9,944,991 B2  
APPLICATION NO. : 14/438715  
DATED : April 17, 2018  
INVENTOR(S) : Irene M. Ghobrial, Aldo M. Roccaro and Salomon Manier Page 1 of 1

It is certified that error appears in the above-identified patent and that said Letters Patent is hereby corrected as shown below:

In Column 65, Line 19, in Claim 4:  
Delete "Let-7b" and insert -- let-7b --, therefor.

In Column 65, Line 19, in Claim 4:  
Delete "miR-Let-7c" and insert -- miR-let-7c --, therefor.

In Column 65, Line 20, in Claim 4:  
Delete "miR-Let-7b" and insert -- miR-let-7b --, therefor.

In Column 65, Line 20, in Claim 4:  
Delete "miR-Let-7c" and insert -- miR-let-7c --, therefor.

Signed and Sealed this  
Tenth Day of July, 2018

Andrei Iancu  
*Director of the United States Patent and Trademark Office*